US012702697B2

(12) United States Patent
Cao et al.

(10) Patent No.: US 12,702,697 B2
(45) Date of Patent: Aug. 11, 2026

(54) COMPOSITIONS AND METHODS FOR TREATMENT OF HEADACHE DISORDERS AND NEUROPATHIC PAIN

(71) Applicant: Washington University, St. Louis, MO (US)

(72) Inventors: Yu-Qing Cao, St. Louis, MO (US); Zhiyu Zhang, St. Louis, MO (US); Rong Hu, St. Louis, MO (US); Jintao Zhang, St. Louis, MO (US); Megan E. Cloud, St. Louis, MO (US)

(73) Assignee: Washington University, St. Louis, MO (US)

( * ) Notice: Subject to any disclaimer, the term of this patent is extended or adjusted under 35 U.S.C. 154(b) by 1050 days.

(21) Appl. No.: 17/787,026

(22) PCT Filed: Dec. 18, 2020

(86) PCT No.: PCT/US2020/066202
§ 371 (c)(1),
(2) Date: Jun. 17, 2022

(87) PCT Pub. No.: WO2021/127557
PCT Pub. Date: Jun. 24, 2021

(65) Prior Publication Data

US 2023/0256015 A1 Aug. 17, 2023

Related U.S. Application Data

(60) Provisional application No. 62/949,870, filed on Dec. 18, 2019.

(51) Int. Cl.
*A61K 35/17* (2025.01)
*A61K 38/20* (2006.01)
(Continued)

(52) U.S. Cl.
CPC .......... *A61K 38/2013* (2013.01); *A61K 40/11* (2025.01); *A61K 40/22* (2025.01);
(Continued)

(58) Field of Classification Search
CPC .... A61K 38/2013; A61K 40/11; A61K 40/22; A61K 40/414; A61K 2239/31;
(Continued)

(56) References Cited

U.S. PATENT DOCUMENTS

2014/0004080 A1* 1/2014 Klatzmann ............ A61P 25/00 424/85.2

FOREIGN PATENT DOCUMENTS

JP 2011229437 * 11/2011

OTHER PUBLICATIONS

Stirpargo et al. “Impaired Natural Killer Activity in PBLs from Cluster Headache Patients is restored by Interleukin 2” Int J. Immunotherapy V1 (3) 181-186 (1990) (Year: 1990).*
Hartemann et al. “Low-dose interleukin 2 in patients with type 1 diabetes: a phase 1/2 randomised, double-blind, placebo-controlled trial” Lancet/Diabetes—endocrinology, vol. 1, Dec. 2013 (Year: 2013).*

(Continued)

*Primary Examiner* — Tracy Vivlemore
*Assistant Examiner* — Lauren K Van Buren
(74) *Attorney, Agent, or Firm* — Polsinelli PC

(57) ABSTRACT

Among the various aspects of the present disclosure is the provision of compositions and methods of treating or preventing various headache disorders or neuropathic pain by increasing the number of Treg cells in a subject. In particular, low dose IL-2, rapamycin, statin or Treg cell administration are shown to be useful in treating or preventing headache or neuropathic pain.

9 Claims, 25 Drawing Sheets
(21 of 25 Drawing Sheet(s) Filed in Color)
Specification includes a Sequence Listing.

(51) Int. Cl.
*A61K 40/11* (2025.01)
*A61K 40/22* (2025.01)
*A61K 40/41* (2025.01)
*A61P 25/00* (2006.01)

(52) U.S. Cl.
CPC ............ *A61K 40/414* (2025.01); *A61P 25/00* (2018.01); *A61K 2239/31* (2023.05); *A61K 2239/38* (2023.05)

(58) Field of Classification Search
CPC ...... A61K 2239/38; A61P 25/00; A61P 25/06; C07K 14/55
See application file for complete search history.

(56) References Cited

OTHER PUBLICATIONS

Meloni et al. “Interleukin-2 May Induce Prolonged Remissions in Advanced Acute Myelogenous Leukemia” Blood, vol. 84, No. 7 Oct. 1, 1994; pp. 2158-2163 (Year: 1994).*

St Judes Internet Document on IL-2 (Year: 2025).*

International Preliminary Report on Patentability for International Application No. PCT/US2020/066202, mailed Jun. 30, 2022, 07 Pages.

International Search Report and Written Opinion for International Application No. PCT/US2020/066202, mailed Apr. 30, 2021, 11 Pages.

Laumet G., et al., “T Cells as an Emerging Target for Chronic Pain Therapy,” Frontiers in Molecular Neuroscience, Sep. 11, 2019, vol. 12, Article No. 216, pp. 1-17, doi: 10.3389/fnmol.2019.00216, ISSN 1662-5099, XP055837409.

* cited by examiner

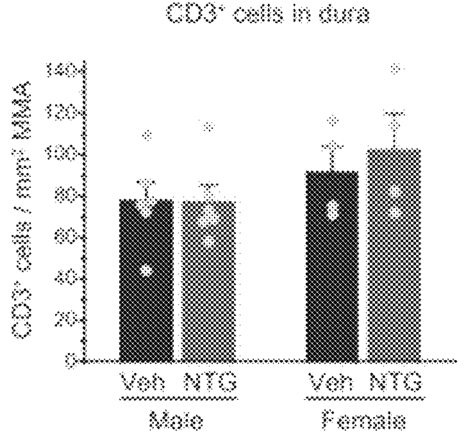
FIG. 1C
CD3+ cells in female TG and DRG
**
35
30
25
20
15
10
5
0
CD3+ cells / mm²
Veh NTG
TG
Veh NTG
L4 DRG
FIG. 1D
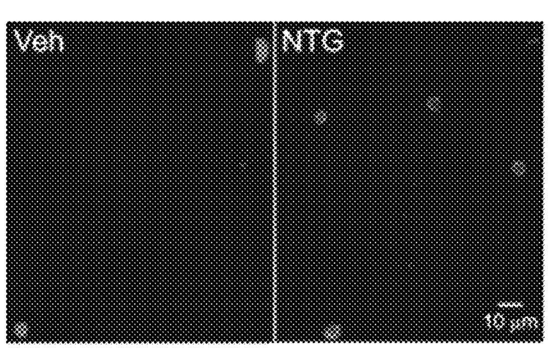
FIG. 1E
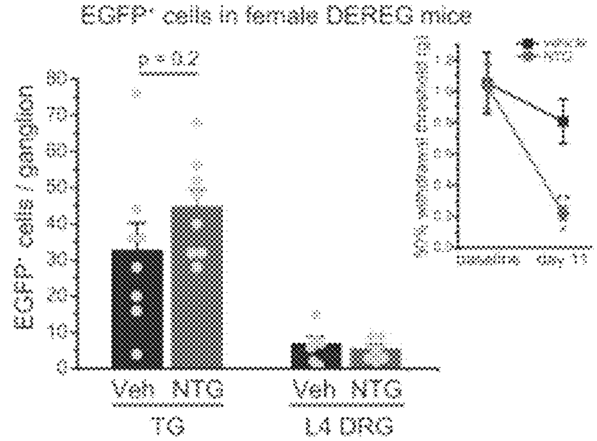
FIG. 1F

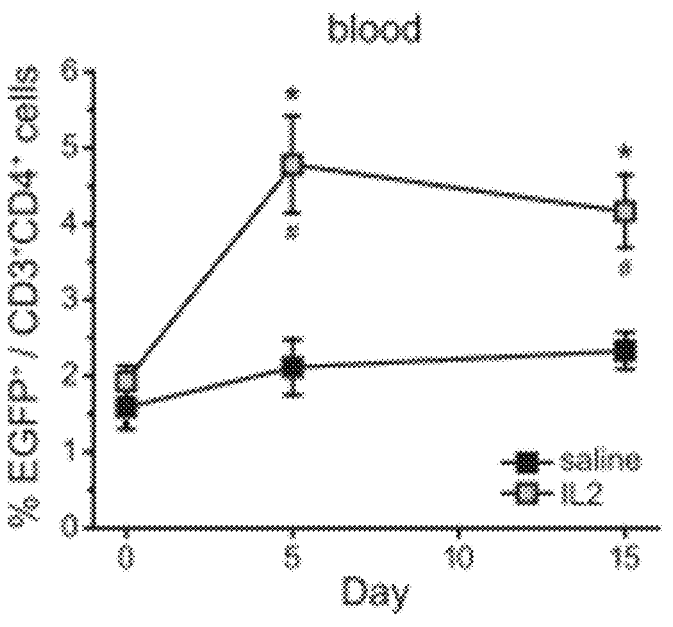
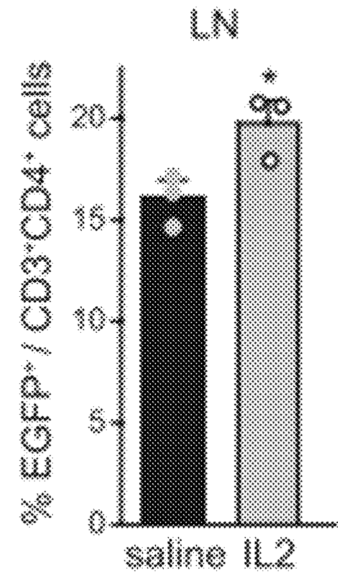
FIG. 2A
FIG. 2B
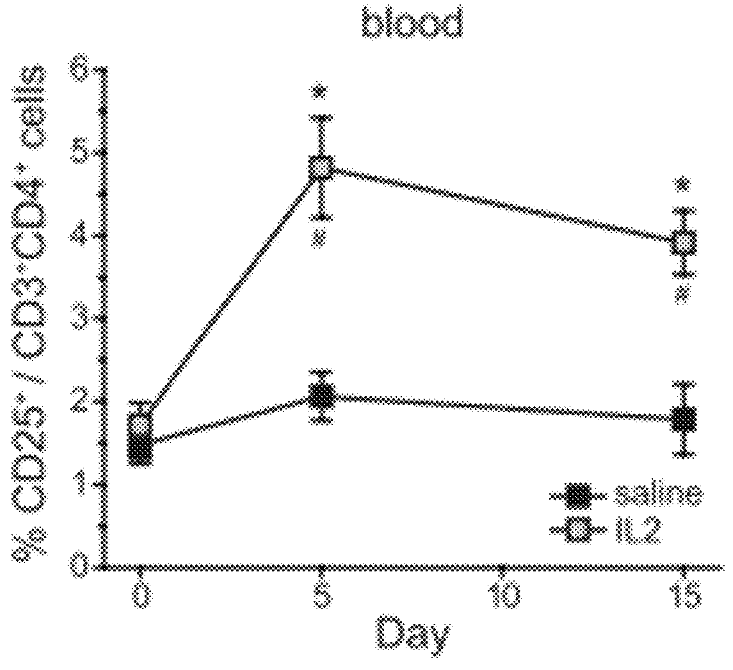
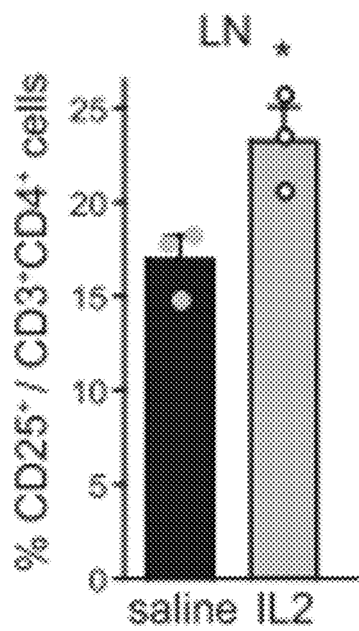
FIG. 2C
FIG. 2D 60
50
40
30
20
10
0
% CD3+ / live cells
saline
IL2
Day
0
5
15
15
Blood
LN

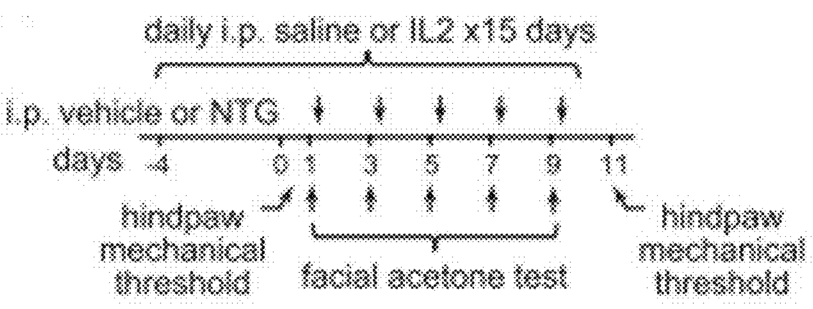
FIG. 4A
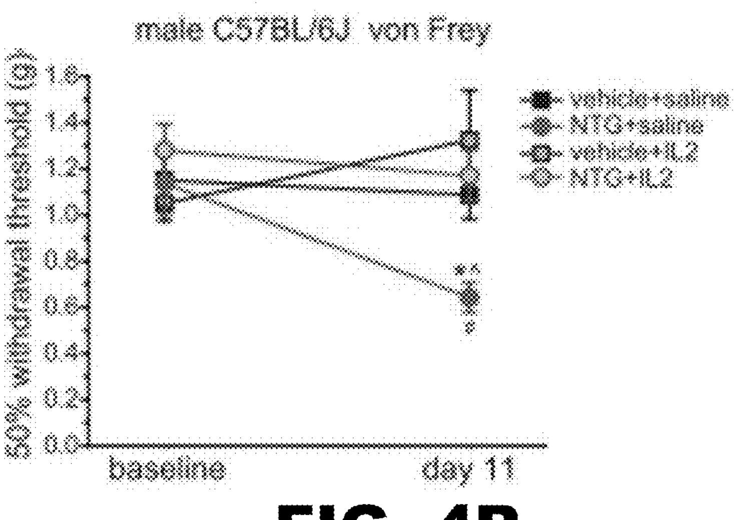
FIG. 4B
female C57BL/6J acetone
% of baseline behavior
Day
vehicle+saline
NTG+saline
vehicle+IL2
NTG+IL2
FIG. 4C
female Swiss Webster acetone
% of baseline behavior
Day
NTG+saline
NTG+IL2
FIG. 4D

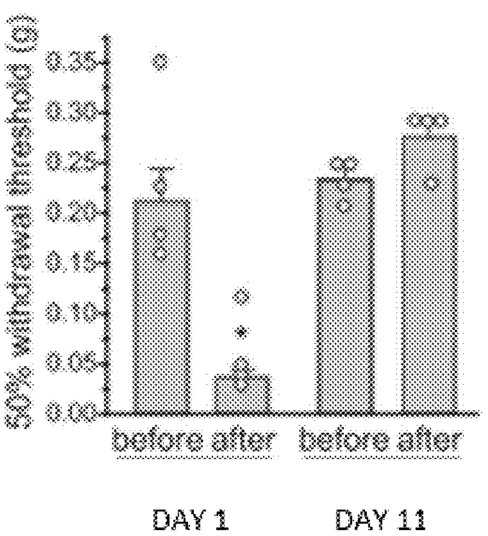
FIG. 6C
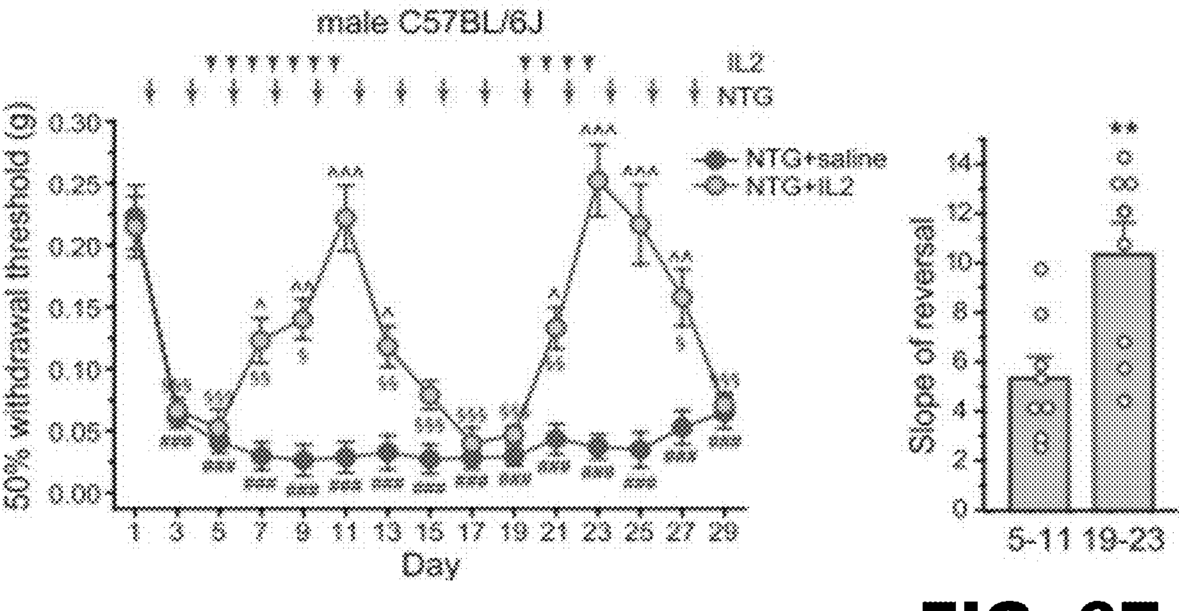
FIG. 6D
FIG. 6E male C57BL/6J day 4, adoptive transfer

NTG

50% withdrawal threshold (g)

NTG+CD25−CD4+

NTG+Treg

Day

50% withdrawal threshold (g)

before after NTG

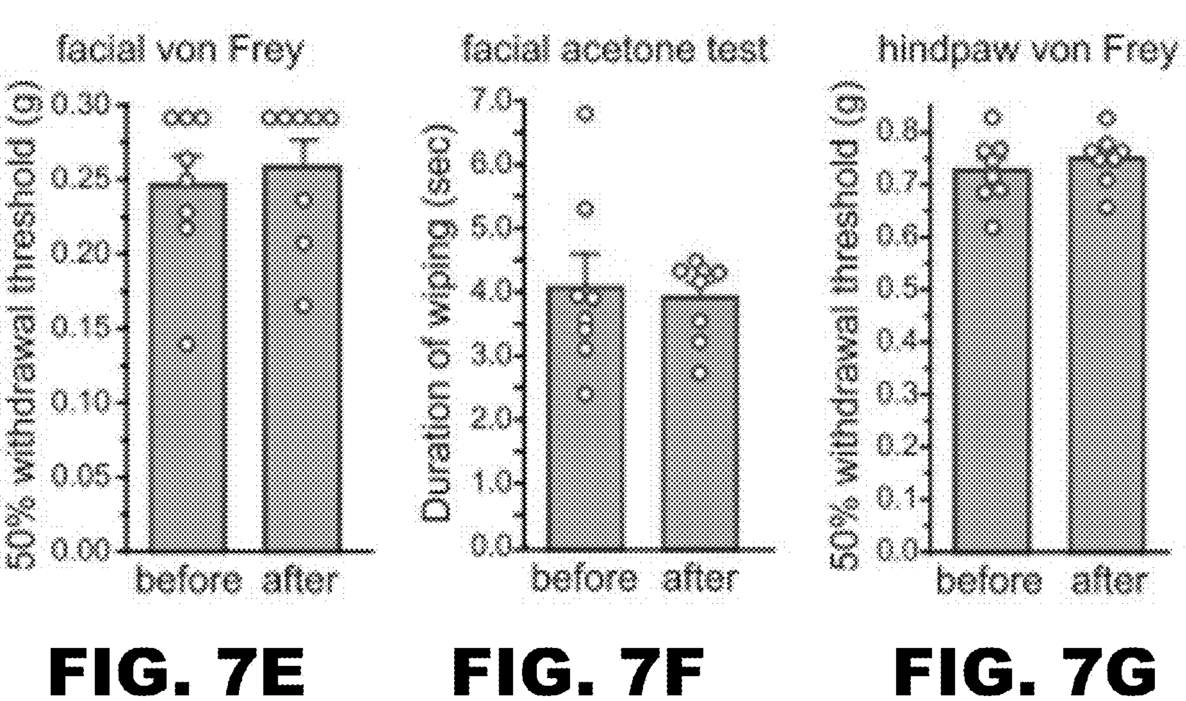
FIG. 7E
FIG. 7F
FIG. 7G
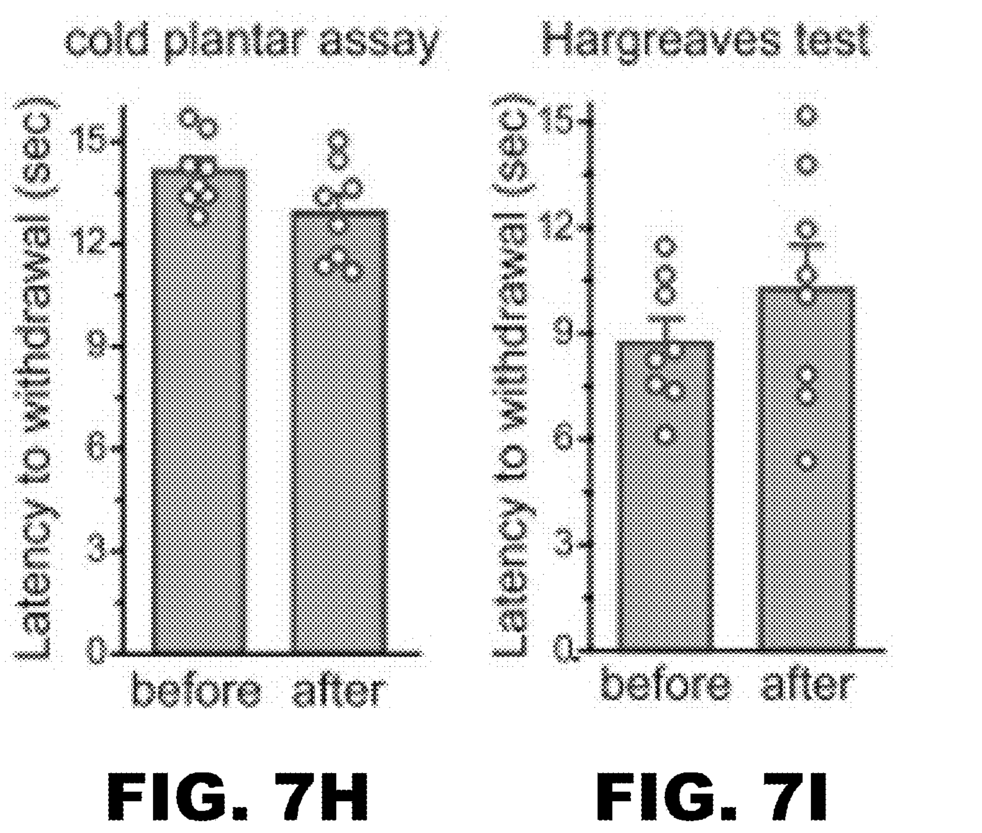
FIG. 7H
FIG. 7I

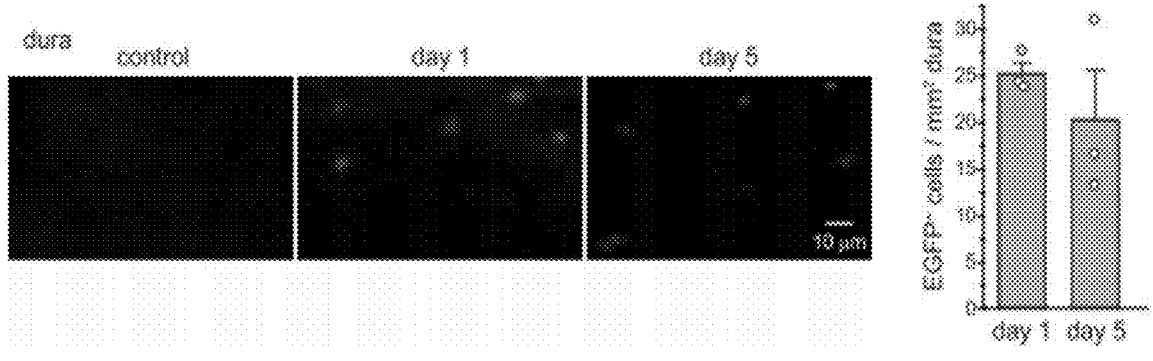
FIG. 8A
FIG. 8B
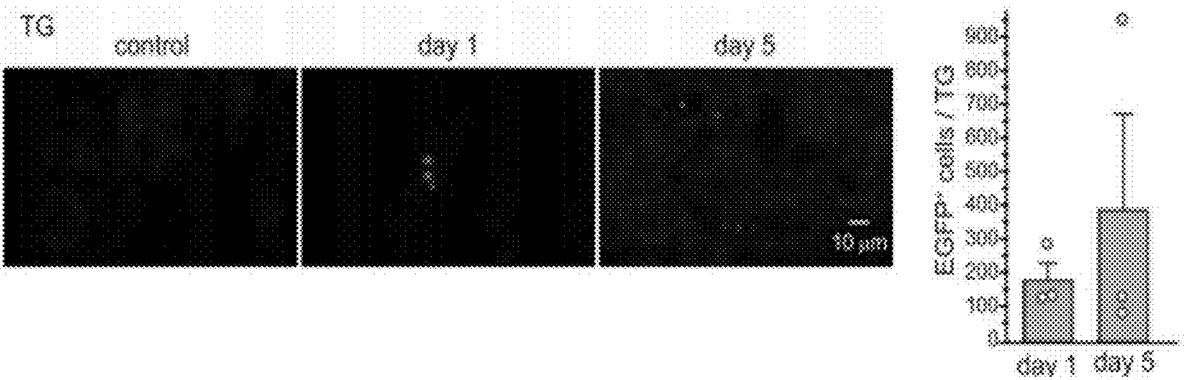
FIG. 8C
FIG. 8D

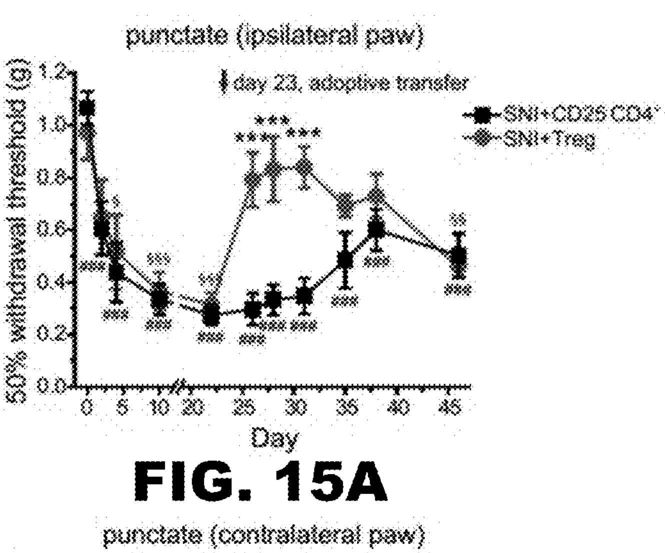
FIG. 15A
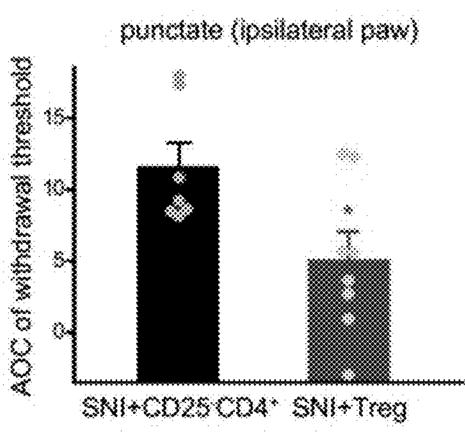
FIG. 15B
punctate (contralateral paw)
day 23, adoptive transfer
SNI+CD25⁻CD4⁺
SNI+Treg
50% withdrawal threshold (g)
Day
FIG. 15C
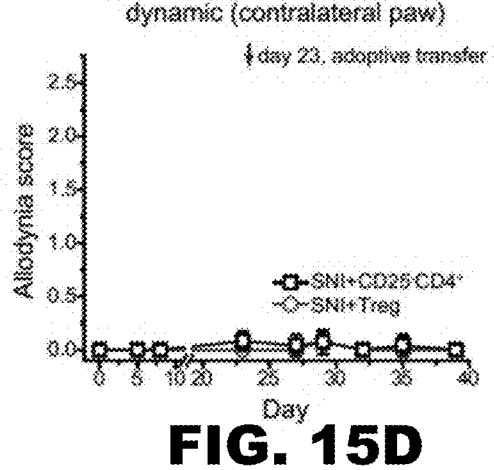
FIG. 15D
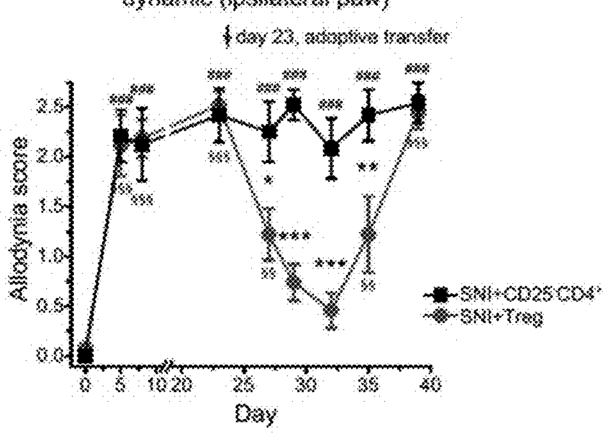
FIG. 15E
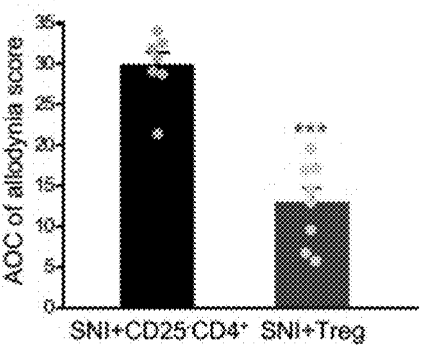
FIG. 15F

SEQUENCE LISTING

```
<160> NUMBER OF SEQ ID NOS: 2

<210> SEQ ID NO 1
<211> LENGTH: 26
<212> TYPE: DNA
<213> ORGANISM: Artificial Sequence
<220> FEATURE:
<223> OTHER INFORMATION: Synthesized

<400> SEQUENCE: 1

cctacggcgt gcagtgcttc agccgc                                          26


<210> SEQ ID NO 2
<211> LENGTH: 25
<212> TYPE: DNA
<213> ORGANISM: Artificial Sequence
<220> FEATURE:
<223> OTHER INFORMATION: Synthesized

<400> SEQUENCE: 2

cggcgagctg cacgctgccg tcctc                                           25
```

COMPOSITIONS AND METHODS FOR TREATMENT OF HEADACHE DISORDERS AND NEUROPATHIC PAIN

CROSS-REFERENCE TO RELATED APPLICATIONS

This application claims benefit of International Application No. PCT/US2020/066202, filed Dec. 18, 2020, which claims benefit from U.S. Provisional Application Ser. No. 62/949,870 filed on Dec. 18, 2019, the disclosures of which are is-incorporated herein by reference in their its-entirety.

GOVERNMENTAL RIGHTS

This invention was made with government support under NS083698 and NS103550 awarded by the National Institutes of Health and W81XWH-18-1-0627 awarded by the Army Medical Research and Materiel Command (ARMY/MRMC). The government has certain rights in the invention.

FIELD OF THE TECHNOLOGY

Disclosed herein are compositions and methods for treating or preventing various headache or nerve injury disorders in a subject. In particular, the disclosure relates to the administration of low dose IL-2 and/or adoptive transfer of Treg cells.

REFERENCE TO SEQUENCE LISTING

This application contains a Sequence Listing that has been submitted in ASCII format via EFS-Web and is hereby incorporated by reference in its entirety. The ASCII copy, created on Dec. 16, 2020, is named 670061_ST25, and is 726 bytes in size.

BACKGROUND

Headache disorders are among the most common disorders of the nervous system. It has been estimated that almost half of the adult population have had a headache at least once within the last year. Headache disorders, which are characterized by recurrent headache, are associated with personal and societal burdens of pain, disability, damaged quality of life, and financial cost. Headache itself is a painful and disabling feature of a small number of primary headache disorders, namely migraine, tension-type headache, and cluster headache. Headache can also be caused by or occur secondarily to a long list of other conditions, the most common of which are medication-overuse headache and post-traumatic headache. Worldwide, a minority of people with headache disorders are diagnosed appropriately by a healthcare provider. Headache has been underestimated, under-recognized and under-treated throughout the world.

Globally, it has been estimated that prevalence among adults of current headache disorder (symptomatic at least once within the last year) is about 50%. Half to three quarters of adults aged 18-65 years in the world have had headache in the last year and, among those individuals, 30% or more have reported migraine. Headache on 15 or more days every month affects 1.7-4% of the world's adult population. Despite regional variations, headache disorders are a worldwide problem, affecting people of all ages, races, income levels and geographical areas.

Not only is headache painful, but it is also disabling. In the Global Burden of Disease Study, updated in 2013, migraine on its own was found to be the sixth highest cause worldwide of years lost due to disability (YLD). Headache disorders collectively were third highest.

Headache disorders impose a recognizable burden on sufferers including sometimes substantial personal suffering, impaired quality of life and financial cost. Repeated headache attacks, and often the constant fear of the next one, damage family life, social life and employment. The long-term effort of coping with a chronic headache disorder may also predispose the individual to other illnesses. For example, anxiety and depression are significantly more common in people with migraine than in healthy individuals.

Headache disorders are a public-health concern given the associated disability and financial costs to society. As headache disorders are most troublesome in the productive years (late teens to 50s), estimates of their financial cost to society—principally from lost working hours and reduced productivity—are massive. In the United Kingdom, for example, some 25 million working- or school-days are lost every year because of migraine alone; this financial cost may be matched by TTH and MOH combined. Headache is high among causes of consulting medical practitioners: one-third of all neurological consultations were for headache, in one survey.

Yet, many of those troubled by headache do not receive effective care. For example, in the United States of America and the United Kingdom, only half of those identified with migraine had seen a doctor for headache-related reasons in the previous 12 months, and only two-thirds had been correctly diagnosed. Most were solely reliant on over-the-counter medications.

Appropriate treatment of headache disorders requires training of health professionals, accurate diagnosis and recognition of the conditions, appropriate treatment with cost-effective medications, simple lifestyle modifications, and patient education. However, many headache disorders lack effective therapeutics and some can even lead to medication-overuse headache.

Therefore, a need in the art exists for compositions and methods for treating various headache disorders and post-traumatic neuropathic pain.

The disclosure encompasses a method of treating or preventing a headache in a subject in need thereof. The method may comprise administering a composition comprising an active agent which increases the amount of Treg cells in the subject, wherein at least one symptom of the headache or neuropathic pain is reduced, eliminated or prevented. The active agent may be selected from Interleukin-2 (IL-2), rapamycin, a statin, TGFβ1, sulfadoxine, tobramycin, spectinomycin, lomefloxacin, norfloxacin, lincomycin, clinafloxacin, novobiocin, clindamycin, imipenem, tetracycline, tinidazole, terbinafine, meloxicam, tenoxicam, piroxicam, mefenamic acid, ketoprofen, ibuprofen, prednisone, prednisolone, methylprednisolone, dexamethasone, hydrocortisone, triamcinolone, medroxyprogesterone 17-acetate, terfenadine, temozolomide, toremifene, gefitinib, ribavirin, troglitazone, clomiphene, aminophylline, chloroquine, retinoic acid and combinations thereof. In a specific instance, the active agent is IL-2.

The headache may be a migraine, tension-type headache, cluster headache, medication-overuse headache, or trauma induced acute or chronic headache. The subject may be administered IL-2 at a dose of about 0.05 to about 2 MIU/m2/day, or preferably about 0.2 to about IMUI/m2/day. In a specific instance, the IL-2 may be administered at a dose of less than about 3.5 MIU/day. In a further instance, the IL-2 may be administered at a dose of less than about 2 MIU/day. The administration may be performed repeatedly. The treatment may comprise at least a first course wherein the active agent may be administered once per day during at least 3 consecutive days. The active agent may be administered once per day for 3 to 7 days or once per day for 4 to 5 consecutive days. The active agent may also be administered as a maintenance dose following the initial administration after 1 to 4 weeks. The active agent may be administered by injection or by oral, nasal, or topical administration. In a specific instance, the IL-2 may be administered by subcutaneous route.

The disclosure further encompasses a method of treating or preventing a headache or neuropathic pain in a subject in need thereof. The method may comprise administering a composition comprising a population of T regulatory cells to the subject in an amount that increases the amount Treg cells in the dura, the inured nerve, the dorsal root ganglion or trigeminal ganglion of the subject, wherein at least one symptom of the headache or neuropathic pain is reduced, eliminated, or prevented. The T regulatory cells administered to the subject may be allogeneic or autologous. The T regulatory cells may be derived from peripheral blood mononuclear cells and in a specific instance derived from mobilized peripheral blood mononuclear cells. In another instance, T regulatory cells may be derived cord blood or from adipose stromal vascular fraction cells.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1A-1F show repeated NTG treatment increases the number of $CD3^+$ cells but not Treg cells in mouse TG. FIG. 1A is a time line of experiments. Note that NTG was always injected after the completion of behavioral tests on the same day. FIG. 1B shows repetitive NTG treatment (10 mg/kg, i.p.) induces progressive and sustained hindpaw mechanical hypersensitivity in both male (left, n=6/group) and female C57BL/6J mice (right, n=8/group). Kruskal-Wallis ANOVA on ranks with post hoc Student-Newman-Keuls test: *P<0.05, P<0.01, *P<0.001, between the corresponding vehicle and NTG groups. Friedman test: P<0.05 and P<0.001 within the male and female NTG groups, respectively, ##P<0.01, ###P<0.001, compared with the baseline threshold (day 1). FIG. 1C is the density of $CD3^+$ cells in the dura surrounding the MMA in male (n=6/group) and female C57BL/6J mice (n=4/group) that received repetitive vehicle and NTG injections, respectively. FIG. 1D is the density of $CD3^+$ cells in the TG (n=6/group) and L4 DRG (n=6/group) of female C57BL/6J mice receiving repetitive vehicle and NTG injections, respectively. P<0.01, 2-tailed t test between the corresponding vehicle and NTG groups. FIG. 1E is representative images of $CD3^+$ cells in TG sections from female C57BL/6J mice that received repetitive vehicle or NTG injections (same mice as in D). FIG. 1F shows the number of EGFP+ Treg cells per TG (n=8/group) and per L4 DRG (n=6/group) from female DEREG mice that received repetitive vehicle and NTG injections, respectively. Inset: The 50% withdrawal thresholds to von Frey filaments on the hindpaw of female DEREG mice (n=4/group) before and 2 days after the last NTG or vehicle injections as shown in A. Kruskal-Wallis ANOVA on ranks with post hoc Student-Newman-Keuls test: P<0.01, between the corresponding vehicle and NTG groups; #P<0.05, between the NTG-treated groups. ANOVA, analysis variance; DRG, dorsal root ganglia; EGFP, enhanced green fluorescent protein; MMA, middle meningeal artery; TG, trigeminal ganglia.

FIG. 2A-2F show the frequencies of $CD3^+$, $CD4^+$, and Treg cells in the peripheral blood and cervical LNs of DEREG mice treated with daily saline or ld-IL2. FIG. 2A shows the percentage of $EGFP^+$ Treg cells among $CD4^+$ $CD3^+$ T cells in the peripheral blood of male DEREG mice that received 15 daily injections of saline and Id-IL2, respectively (n=3/group). The injections started on day 0, after blood collection for baseline measurement. Two-way RM ANOVA with post hoc Bonferroni test: *P<0.05, between the corresponding saline and IL2 groups; #P<0.05, compared with the baseline value (day 0) in the IL2 group. FIG. 2B shows the frequency of $EGFP^+$ Treg cells among $CD4^+CD3^+$ T cells in the cervical LNs after 15 daily saline or ld-IL2 injections (same mice as in A). *P<0.05, 2-tailed t test. FIG. 2C shows the percentage of $CD25^+$ Treg cells among $CD4^+CD3^+$ T cells in the peripheral blood of saline- and IL2-treated DEREG mice (same as in A). Two-way RM ANOVA with post hoc Bonferroni test: *P<0.05, between the corresponding saline and IL2 groups; #P<0.05, compared with the baseline value (day 0) in the IL2 group. FIG. 2D shows the frequency of $CD25^+$ Treg among $CD4^+CD3^+$ cells in the cervical LNs after 15 daily saline or ld-IL2 injections (same mice as in A). *P<0.05, 2-tailed t test. (E and F) The abundance of $CD4^+$ cells among $CD3^+$ cells. FIG. 2E are $CD3^+$ cells among live lymphocytes. FIG. 2F shows saline- and IL2-treated mice (same as in A). ANOVA, analysis of variance; EGFP, enhanced green fluorescent protein; LN, lymph node; RM, repeated measures.

FIG. 3A shows the number of lymphocytes in total splenocytes of male C57BL/6J mice that received 15 daily injections of saline and ld-IL2. FIG. 3B shows the number of $CD25^+CD4^+$ Treg cells in total splenocytes of male C57BL/6J mice that received 15 daily injections of saline and ld-IL2, respectively (n=5 mice/group). *P<0.001, 2-tailed t test. FIG. 3C shows the frequency of CD25+ Treg cells among CD3+ CD4+ splenocytes from saline- and IL2-treated mice (same as in A). *P<0.001, 2-tailed t test. (D and E) FIG. 3D shows the number of $CD3^+CD4^+$ cells in splenocytes from saline- and IL2-treated mice (same as in A). FIG. 3E shows the number of $CD3^+CD8^+$ cells shows in splenocytes from saline- and IL2-treated mice (same as in A). *P<0.05, 2-tailed t test. FIG. 3F shows the secretion of IFNγ in response to CD3/CD28 stimulation in ELISA assay (n=5/group, same as in A). P<0.01, 2-tailed t test. FIG. 3**G shows the number of INFγ-secreting ($IFN\gamma^+$) cells.

FIG. 4A-4D shows pretreatment with ld-IL2 prevents the development of NTG-induced skin hypersensitivity. FIG. 4A is a time line of experiments in B and C. Note that IL2 and/or NTG were always injected after the completion of behavioral tests on the same day. FIG. 4B. shows Hindpaw mechanical thresholds of male C57BL/6J mice at baseline and 2 days after the last NTG or vehicle injections as shown in A (n=6, 7, 6, and 5 mice in vehicle+saline, NTG+saline, vehicle+IL2, and NTG+IL2 groups, respectively). Kruskal-Wallis ANOVA on ranks with Student-Newman-Keuls post hoc test. *P<0.05, between the vehicle+saline and NTG+saline groups on day 11; ^P<0.05, between the NTG 1 saline and NTG 1 IL2 groups on day 11; #P<0.05, between the baseline and day 11 NTG+saline groups. FIG. 4C shows the effects of repetitive NTG and/or ld-IL2 on the duration of acetone-induced cheek wiping in female C57BL/6J mice (n=14, 20, 9, and 12 in vehicle+saline, NTG+saline, vehicle+IL2, and NTG+IL2 groups, respectively). The duration of wiping was normalized to the baseline values (day 1) in individual mice. Two-way RM ANOVA: P<0.01; post hoc t test with Bonferroni correction: *P<0.05, P<0.01, between the corresponding vehicle and NTG groups; ^ P<0.05, between the corresponding NTG+saline and NTG+IL2 groups; one-way RM ANOVA: P<0.05 within the NTG+saline group, post hoc one-sample t test with Bonferroni correction: #P<0.05, ##P<0.01, compared with the baseline. FIG. 4**D shows the effects of repetitive NTG and/or ld-IL2 on the duration of acetone-induced cheek wiping in female Swiss Webster mice (n=8 and 11 in NTG+saline and NTG+IL2 groups, respectively). The duration of wiping was normalized to the baseline values (day 1) in individual mice. Arrows and arrowheads indicate the injections of NTG and IL2, respectively. Two-way RM ANOVA: P<0.05; post hoc t test with Bonferroni correction: ^^P<0.01, between the corresponding NTG+saline and NTG+IL2 groups; one-way RM ANOVA: P<0.001 within the NTG+saline group, post hoc one-sample t test with Bonferroni correction: #P<0.05, ##P<0.01, compared with the baseline. ANOVA, analysis of variance; RM, repeated measures.

FIG. 5A shows representative images of $EGFP^+$ Treg cells and $CD3^+$ cells in the dura of DEREG mice that received repeated NTG and/or ld-IL2 administrations. Arrowheads indicate double-labeled $CD3^+$ $EGFP^+$ Treg cells. (B and C) FIG. 5B shows daily ld-IL2 treatment (×15 days) significantly increases the number of $EGFP^+$ Treg cells. FIG. 5C shows daily ld-IL2 treatment (×15 days) significantly increases the frequency of $EGFP^+$ Treg among $CD3^+$ T cells in the dura surrounding the MMA of male DEREG mice (n=3/group). P<0.01, *P<0.001, two-way ANOVA with post hoc Bonferroni test. FIG. 5D shows representative images of $EGFP^+$ Treg cells in the TG of DEREG mice that received repeated NTG and/or ld-IL2 administrations. FIG. 5E shows daily ld-IL2 treatment (×15 days) significantly increases the number of EGFP+ Treg cells in the TG of female DEREG mice (n=5 and 4 mice in vehicle+IL2 and NTG+IL2 groups; vehicle+saline and NTG+saline groups: same mice as in FIG. 1F). P<0.01, *P<0.001, two-way ANOVA with post hoc Bonferroni test. FIG. 5F shows daily ld-IL2 treatment (×15 days) significantly increases the number of EGFP+ Treg cells in the DRG of male DEREG mice (n=6/group). **P<0.01, 2-tailed t test. ANOVA, analysis of variance; DRG, dorsal root ganglia; EGFP, enhanced green fluorescent protein; MMA, middle meningeal artery; TG, trigeminal ganglia.

FIG. 6A-6E show NTG-induced persistent skin hypersensitivity is reversed by ld-IL2 treatment. FIG. 6A shows the effects of repetitive NTG and/or ld-IL2 on the 50% withdrawal thresholds to von Frey filaments at the periorbital region of female Swiss Webster mice (n=6, 6, 5, and 9 in vehicle+saline, NTG+saline, vehicle+IL2, and NTG+IL2 groups, respectively). Arrows and arrowheads indicate the injections of NTG and IL2, respectively. Note that IL2 and NTG were always injected after the completion of behavioral tests on the same day. Kruskal-Wallis ANOVA on ranks: P<0.05; post hoc Student-Newman-Keuls test: *P<0.001, between the corresponding vehicle+saline and NTG+saline groups; ^^P+0.01, ^^^P<0.001, between the corresponding NTG+saline and NTG+IL2 groups; † P<0.05, †††P<0.001, between the corresponding NTG+IL2 and vehicle+IL2 groups; Friedman test: P<0.05 within the NTG+saline group, ###P<0.001, compared with the baseline threshold (day 1); P<0.001 within the NTG 1 IL2 group, §§§ P<0.001, compared with the baseline threshold (day 1). FIG. 6B shows the effects of repeated NTG and/or Id-IL2 on the facial mechanical thresholds of female C57BL/6J mice (n=5 and 6 in NTG+saline and NTG+IL2 groups, respectively). Kruskal-Wallis ANOVA on ranks: P<0.05; post hoc Student-Newman-Keuls test: ^^^P<0.001, between the corresponding NTG+saline and NTG+IL2 groups; Friedman test: P<0.05 within the NTG+saline group, ###P<0.001, compared with the baseline threshold (day 1); P<0.001 within the NTG 1 IL2 group, §§§ P<0.001, compared with the baseline threshold (day 1). FIG. 6**C shows in 4 mice (of the 6 mice in B, NTG+IL2 group), facial mechanical thresholds before and 3 hours after NTG injections were measured on day 1 (before ld-IL2) and day 11 (after 7 ld-IL2 injections). *P<0.05, Mann-Whitney U test comparing naïve mice before and after NTG treatment. FIG. 6D shows the effects of repeated NTG and/or Id-IL2 on the facial mechanical thresholds of male C57BL/6J mice (n=6 and 9 in NTG+saline and NTG+IL2 groups, respectively). NTG was injected every 2 days throughout the experiment. Mice in the NTG+IL2 group received 2 sessions of daily IL2 treatments (day 4-10 and day 19-22, respectively). Kruskal-Wallis ANOVA on ranks: P<0.01; post hoc Student-Newman-Keuls test: ^ P<0.05, ^^P<0.01, ^^^P<0.001, between the corresponding NTG+saline and NTG+IL2 groups; Friedman test: P<0.001 within the NTG+saline group, ###P<0.001, compared with the baseline threshold (day 1); P<0.001 within the NTG+IL2 group, § P<0.05, §§ P<0.01, §§§ P<0.001, compared with the baseline threshold (day 1). FIG. 6E shows the slope of ld-IL2-induced reversal of mechanical threshold (same mice as in D). **P<0.01, 2-tailed t test. The thresholds between day 5 to 11 and day 19 to 23 in individual mice were fitted by linear regression to calculate the slope, respectively. ANOVA, analysis of variance.

FIG. 7A-7I show Treg cells mediate the therapeutic effect of ld-IL2. FIG. 7A shows the frequency of $CD25^+$ Treg cells among $CD4^+CD3^+$ T cells in the peripheral blood of mice that received CD25 antibody on day 0 as indicated by the arrow (n=4). One-way RM ANOVA with post hoc Bonferroni test: *P<0.001, compared with the baseline value (day 0). Inset: Depletion of Treg cells did not alter baseline facial mechanical thresholds. FIG. 7B shows depletion of Treg cells abolished the effect of ld-IL2. Male C57BL/6J mice received 1 i.p. injection of anti-CD25 antibody (Ab) or control IgG (n=5 and 7, respectively). Three days later, mice were treated with NTG and IL2 injections as indicated by the arrows. Kruskal-Wallis ANOVA on ranks: P<0.01; post hoc Student-Newman-Keuls test: *P<0.001, between the corresponding NTG+IL2+control IgG and NTG+IL21 anti-CD25 Ab groups; Friedman test: P<0.01 within the NTG+IL2+anti-CD25 Ab group, ###P<0.001, compared with the baseline threshold (day 3); P<0.001 within the NTG+IL2+control IgG group, §§ P<0.01, §§§ P<0.001, compared with the baseline threshold. FIG. 7C shows NTG-induced persistent facial skin hypersensitivity was reversed by the adoptive transfer of Treg cells. Male C57BL/6J mice received NTG injections every 2 days as indicated by the red arrows. On day 4, mice received adoptive transfer of Treg cells or $CD25^+CD4^+$ cells as indicated by the blue arrow (n=6 per group). Kruskal-Wallis ANOVA on ranks: P<0.01; post hoc Student-Newman-Keuls test: P<0.01, *P<0.001, between the corresponding NTG+ Treg and NTG+$CD25^+CD4^+$ groups; Friedman test: P<0.05 within the NTG<$CD25^+CD4^+$ group, ###P<0.001, compared with the baseline threshold (day 1); P<0.05 within the NTG+ Treg group, §§ P<0.01, §§§ P<0.001, compared with the baseline threshold. FIG. 7D shows In 4 mice (of the 6 mice in C NTG+ Treg group), facial mechanical thresholds before and 3 hours after NTG injections were measured 1 week after the Treg adoptive transfer (day 11). (E-1) Baseline nociception is not altered by Treg adoptive transfer. Baseline nociceptive responses were measured before and 6 to 10 days after the adoptive transfer of $1\times10^6$ Treg cells (n=8 male C57BL/6J mice). FIG. 7E shows the 50% withdrawal thresholds to von Frey filaments on facial skin. FIG. 7F shows the time spent wiping the treated area after application of 12-mL acetone to the shaved cheek. FIG. 7G shows the 50% withdrawal threshold to von Frey filaments on the hindpaw. FIG. 7H shows the withdrawal latency to cold stimuli on the hindpaw. FIG. 7I shows the withdrawal latency to radiant heat stimuli on the hindpaw. ANOVA, analysis of variance; RM, repeated measures.

FIG. 8A-8D show adoptively transferred Treg cells traffic to the dura and TG. FIG. 8A shows representative images of $EGFP^+$ Treg cells in the dura of a C57BL/6J mouse that received adoptive transfer of Treg cells from DEREG mice. The control image was from the dura of a naïve mouse. FIG. 8B shows the number of $EGFP^+$ Treg cells in the dura 1 and 5 days after adoptive transfer of Treg cells from DEREG mice to male C57BL/6J mice (n 5 3). FIG. 8C shows representative images of $EGFP^+$ Treg cells in TG sections from a C57BL6/J mouse that received adoptive transfer of Treg cells from DEREG mice. The control image was from the TG section of a naïve mouse. FIG. 8D shows the number of $EGFP^+$ Treg cells per TG 1 and 5 days after adoptive transfer (same mice as in B). EGFP, enhanced green fluorescent protein; TG, trigeminal ganglia.

FIG. 9A shows the time line of experiments. Note that IL2 and NTG were always injected after the completion of behavioral tests on the same day. FIG. 9B shows mild traumatic brain injury-induced facial skin hypersensitivity in female Swiss Webster mice was prevented by ld-IL2 treatment between post-mTBI day 1 to 9 (n 5 10-12 mice/group). The facial mechanical thresholds were normalized to the mean baseline values of individual groups on day 0 (before sham/mTBI). The arrow and the horizontal bar indicate the sham/mTBI procedure and the daily Id-12 treatment, respectively. Kruskal-Wallis ANOVA on ranks: P<0.01; post hoc Student-Newman-Keuls test: *P<0.05, P<0.01, between the corresponding sham+saline and mTBI+saline groups; ^ P<0.05, ^^P<0.01 ^^^P<0.001, between the corresponding mTBI+saline and mTBI+IL2 groups; Friedman test: P<0.05 within the mTBI+saline group, #P<0.05, ##P<0.01, compared with the baseline threshold (day 0). FIG. 9**C shows normalized facial mechanical thresholds on day 39. Female Swiss Webster mice received 4 daily low-dose NTG injections (day 35-38) after the resolution of mTBI-induced facial skin hypersensitivity (same mice as in B). The facial mechanical thresholds were normalized to the mean values of individual groups on day 35 (before NTG injections). Kruskal-Wallis ANOVA on ranks: P<0.01; post hoc Student-Newman-Keuls test: *P<0.05 between sham+saline and mTBI+saline groups; ^ P<0.05 between mTBI+saline and mTBI+IL2 groups. FIG. 9D shows delayed ld-IL2 treatment reversed mTBI-induced facial skin hypersensitivity in male Swiss Webster mice (n=10-12 mice/group). The arrow and the horizontal bar indicate the sham/mTBI procedure and the daily Id-12 treatment, respectively. Kruskal-Wallis ANOVA on ranks: P<0.05; post hoc Student-Newman-Keuls test: *P<0.05, P<0.01, between the corresponding sham+saline and mTBI+saline groups; ^ P<0.05, between the corresponding mTBI+saline and mTBI+IL2 groups; † P<0.05, ††P<0.01, between the corresponding sham+saline/IL2 and mTBI+IL2 groups; !P<0.05, !!P<0.01, between the corresponding sham+IL2 and mTBI+saline groups; Friedman test: P<0.001 within the mTBI+saline group, #P<0.05, ##P<0.01, ###P<0.001, compared with the baseline threshold (day 0); Friedman test: P<0.001 within the mTBI+IL2 group, §§ P<0.01, §§§ P<0.001, compared with the baseline threshold (day 0). FIG. 9**E shows after the resolution of mTBI-induced facial skin hypersensitivity, daily low-dose NTG injections produced persistent facial skin sensitization in mice that received mTBI but not in mice that received ld-IL2 treatment after mTBI (same mice as in D). Arrows indicate NTG injections. Kruskal-Wallis ANOVA on ranks: P<0.001; post hoc Student-Newman-Keuls test: *P<0.05, P<0.01, between the corresponding sham+saline and mTBI+saline groups; ^^P<0.01, between the corresponding mTBI+saline and mTBI+IL2 groups; Friedman test: P<0.001 within the mTBI 1 saline group, ###P<0.01, ###P<0.001, compared with the pre-NTG threshold (day 35). ANOVA, analysis of variance; EGFP, enhanced green fluorescent protein; mTBI, mild traumatic brain injury; PTH, post-traumatic headache; TG, trigeminal ganglia. FIG. 9F shows adoptive transfer of $CD25^+CD4^+$ Treg cells ($1\times10^6$/mouse, i.v.) reverses mTBI-induced acute facial mechanical hyper-sensitivity) in male C57BL/6J mice (n=10). FIG. 9G shows adoptive transfer of CD25+CD4+ Treg cells (1×106/mouse, i.v.) reverses mTBI-induced latent sensitization in male C57BL/6J mice (n=10). Control mice received $1\times10^6$ $CD25^-CD4^+$ T cells. *p<0.001, mTBI+ Treg vs mTBI+ control; ###p<0.001, § p<0.05, §§§ p<0.001, relative to the baseline thresholds within individual groups.

FIG. 10A shows the time line of experiments. FIG. 10B shows latency to fall from the accelerating rotarod in 3 consecutive trials (n=7 male Swiss Webster mice/group). FIG. 10C shows the latency to fall from the accelerating rotarod was averaged from the 3 trials in individual mice (same mice as in B). FIG. 10D shows the average time to remove adhesive tape strips was comparable between sham and mTBI mice (same mice as in B). FIG. 10E shows the total time spent moving in the open-field test (n=8 and 7 male Swiss Webster mice in sham and mTBI groups, respectively). FIG. 10F shows the distance traveled in the open field in 10-minute bins (same mice as in E). FIG. 10G shows the total distance traveled. FIG. 10H shows the number of horizontal beam breaks. FIG. 10I shows the number of vertical beam breaks. FIG. 10J shows total number of entries into the center square. FIG. 10K shows total time spent in the center square during the 1-hour testing period (same mice as in E). The results in E to K were confirmed with a second cohort of male Swiss Webster mice. mTBI, mild traumatic brain injury.

FIG. 11A shows ld-IL2 treatment reverses the facial skin hypersensitivity induced by repeated administration of sumatriptan (SUMA) in male C57BL/6J mice (n=6 and 7 mice in SUMA+saline and SUMA+IL2 groups, respectively). Arrows and arrowheads indicate the injections of SUMA and IL2, respectively. Note that IL2 and SUMA were always injected after the completion of behavioral tests on the same day. Kruskal-Wallis ANOVA on ranks: P<0.01; post hoc Student-Newman-Keuls test: ^^^P<0.001, between the corresponding SUMA+saline and SUMA+IL2 groups; Friedman test: P<0.05 within the SUMA+saline group, ###P<0.001, compared with the baseline threshold (day 1); P<0.001 within the SUMA+IL2 group, §§§ P<0.001, compared with the baseline threshold (day 1). FIG. 11B shows repeated SUMA-induced hindpaw mechanical hypersensitivity is also reversed by ld-IL2 treatment (same mice as in A). Kruskal-Wallis ANOVA on ranks: P<0.01; post hoc Student-Newman-Keuls test: ^^^P<0.001, between the corresponding SUMA+saline and SUMA+IL2 groups; Friedman test: P<0.001 within the SUMA+saline group, ###P<0.001, compared with the baseline threshold (day 1); P<0.001 within the SUMA+IL2 group, §§§ P<0.001, compared with the baseline threshold (day 1). FIG. 11C shows ld-IL2 reverses SUMA-induced facial skin hypersensitivity in female C57BL/6J mice (n=5 and 8 mice in SUMA+saline and SUMA+IL2 groups, respectively). Kruskal-Wallis ANOVA on ranks: P<0.01; post hoc Student-Newman-Keuls test: ^^^P<0.001, between the corresponding SUMA+saline and SUMA+IL2 groups; Friedman test: P<0.05 within the SUMA+saline group, ###P<0.001, compared with the baseline threshold (day 1); P<0.001 within the SUMA+IL2 group, §§§ P+0.001, compared with the baseline threshold (day 1). FIG. 11D shows repeated SUMA-induced hindpaw mechanical hypersensitivity is also reversed by ld-IL2 treatment in female mice (same mice as in C). Kruskal-Wallis ANOVA on ranks: P<0.05; post hoc Student-Newman-Keuls test: ^ P<0.05, ^^^P<0.001, between the corresponding SUMA+saline and SUMA+IL2 groups; Friedman test: P<0.01 within the SUMA+saline group, ###P<0.001, compared with the baseline threshold (day 1); P<0.001 within the SUMA+IL2 group, §§§ P<0.001, compared with the baseline threshold (day 1). ANOVA, analysis of variance; MOH, medication overuse headache.

FIG. 13A shows the changes of the 50% withdrawal thresholds to punctate stimuli (von Frey filaments) on the right hindpaws of female Swiss Webster mice. SNI was performed on the right sciatic nerve on day 0, after the baseline measurement. Daily ld-IL2 or saline treatment started 5 days before SNI and lasted till 21 days post-SNI (n=9 and 8 mice, respectively). Note that IL2 were always injected after the completion of behavioral tests on the same day. Two-way RM ANOVA: p<0.05 between treatment groups; post hoc Student-Newman-Keuls test:  p<0.01, between the corresponding SNI+saline and SNI+IL2 groups. One-way RM ANOVA: p<0.001 and p<0.01 within the SNI+saline and SNI+IL2 groups, respectively, post hoc Dunnett's test: ###p<0.001, compared with the baseline threshold (day 0) in the SNI+saline group; § p<0.05, §§ p<0.01, §§§ P<0.001, compared with the baseline threshold (day 0) in SNI+IL2 group. FIG. 13B shows the integrated area over the time-effect curves (AOCs) of withdrawal threshold calculated from day 0 baseline to day 22 post-SNI (same mice as in A). * p<0.001, two-tailed t-test. FIG. 13C shows the effects of SNI and ld-IL2 on the dynamic allodynia scores of female Swiss Webster mice. SNI was performed on the right sciatic nerve on day 0, after the baseline measurement. Daily ld-IL2 or saline treatment started 5 days before SNI and lasted till 29 days post-SNI (n=5 mice/group). Two-way RM ANOVA: p<0.05 between groups; post hoc t-test with Bonferroni correction: * p<0.05, * p<0.001, between the corresponding SNI+saline and SNI+IL2 groups. One-way RM ANOVA: p=0.43 within the SNI+IL2 group; p<0.001 within the SNI+saline group; post hoc Dunnett's test: #p<0.05, ##p<0.01, ###p<0.001, compared with the baseline score on day 0. FIG. 13D shows The AOCs of dynamic allodynia score calculated from day 0 baseline to day 31 post-SNI (same mice as in C).  p<0.01, two-tailed t-test.

FIG. 14A shows the changes of the 50% withdrawal thresholds to von Frey filaments on the ipsilateral (right) hindpaws of female Swiss Webster mice (n=6-7 mice/group). SNI or sham surgery was performed on the right sciatic nerve on day 0, after the baseline measurement. The horizontal bar indicates the duration of daily Id-12 treatment. Two-way RM ANOVA: p<0.05 between groups; post hoc Student-Newman-Keuls test:  p<0.01, between the corresponding SNI+saline and SNI+IL2 groups; ^^ p<0.01, ^^^ p<0.001, between the corresponding sham+saline and SNI+saline groups; † p<0.05, †\ p<0.01, ††\ p<0.001, between the corresponding sham+IL2 and SNI+IL2 groups. One-way RM ANOVA: p<0.001 within the SNI+saline and SNI+IL2 groups; post hoc Dunnett's test: ##p<0.01, ###p<0.001, compared with the baseline threshold (day 0) in the SNI+saline group; § p<0.05, §§ p<0.01, §§§ p<0.001, compared with the baseline threshold (day 0) in the SNI+IL2 group. FIG. 14B shows The integrated AOCs of withdrawal threshold calculated from day 10 to day 28 post-SNI (same mice as in A). One-way ANOVA: p<0.001; post hoc t-test with Bonferroni correction:  p<0.01, * p<0.001. FIG. 14C shows the 50% withdrawal thresholds to von Frey filaments on the contralateral (left) hindpaws (same mice as in A). Two-way RM ANOVA: p=0.31 between groups. FIG. 14D shows the responses to brush stimuli on the contralateral (left) hindpaws (same mice as in A). Two-way RM ANOVA: p=0.32 between groups. FIG. 14**E shows SNI- and ld-IL2-induced changes of the dynamic allodynia scores of the ipsilateral (right) hindpaws of female Swiss Webster mice (same mice as in A). Two-way RM ANOVA: p<0.001 between groups; post hoc Student-Newman-Keuls test: * p<0.05,  p<0.01, between the corresponding SNI+saline and SNI+IL2 groups; ^^ p<0.01, ^^^ p<0.001, between the corresponding sham+saline and SNI+saline groups; †\ p<0.01, ††\ p<0.001, between the corresponding sham+IL2 and SNI+IL2 groups; One-way RM ANOVA: p<0.001 within SNI+saline and SNI+IL2 groups; post hoc Dunnett's test: ###p<0.001, compared with the baseline score on day 0 in the SNI+saline group; §§§ p<0.001, compared with the baseline score in the SNI+IL2 group. FIG. 14**F shows The AOCs of dynamic allodynia score calculated from day 8 to day 29 post-SNI (same mice as in A). One-way ANOVA: p<0.001; post hoc t-test with Bonferroni correction: * p<0.05, ** P<0.01.

FIG. 15A-15F show adoptive transfer of Treg cells reverses the morphine-resistant punctate and dynamic mechanical allodynia. FIG. 15A shows Changes of the 50% withdrawal thresholds to von Frey filaments on the ipsilateral (right) hindpaws of male C57BL/6J mice (n=7-8 mice/group). SNI was performed on the right sciatic nerve on day 0, after the baseline measurement. On day 23, mice received adoptive transfer of Treg cells or CD25− CD4+ cells as indicated by the arrow. Two-way RM ANOVA: p<0.05 between groups; post hoc Student-Newman-Keuls test: * p<0.001, between the corresponding SNI+CD25− CD4+ and SNI+ Treg groups; One-way RM ANOVA: p<0.001 within the SNI+CD25− CD4+ and SNI+ Treg groups; post hoc Dunnett's test: ###p<0.001, compared with the baseline threshold (day 0) in the SNI+CD251 CD4+ group; § $p<0.05$, §§ $p<0.01$, §§§ $p<0.001$, compared with the baseline threshold (day 0) in the SNI+ Treg group. FIG. 15**B shows the integrated AOCs of withdrawal threshold calculated from day 26 to day 45 post-SNI (same mice as in A). * $p<0.05$, two-tailed t-test. FIG. 15C shows the 50% withdrawal thresholds to von Frey filaments on the contralateral (left) hindpaws (same mice as in A). Two-way RM ANOVA: $p=0.32$ between groups. FIG. 15D shows the responses to brush stimuli on the contralateral (left) hindpaws (same mice as in A). Two-way RM ANOVA: $p=1.00$ between groups. FIG. 15E shows SNI- and Treg transfer-induced changes of the dynamic allodynia scores of the ipsilateral (right) hindpaws of male C57BL/6J mice (same mice as in A). Two-way RM ANOVA: $p<0.001$ between groups; post hoc Student-Newman-Keuls test: * $p<0.05$,  $p<0.01$, * $p<0.001$, between the corresponding SNI+CD25− CD4+ and SNI+ Treg groups; One-way RM ANOVA: $p<0.001$ within SNI+CD25− CD4+ and SNI+ Treg groups; post hoc Dunnett's test: ###$p<0.001$, compared with the baseline score on day 0 in the SNI+CD25− CD4+ group; §§ $p<0.01$, §§§ $p<0.001$, compared with the baseline score in the SNI+ Treg group. FIG. 15F shows The AOCs of dynamic allodynia score calculated from day 27 to day 39 post-SNI (same mice as in A). *** $p<0.001$, two-tailed t-test.

DETAILED DESCRIPTION

Figure 1A:
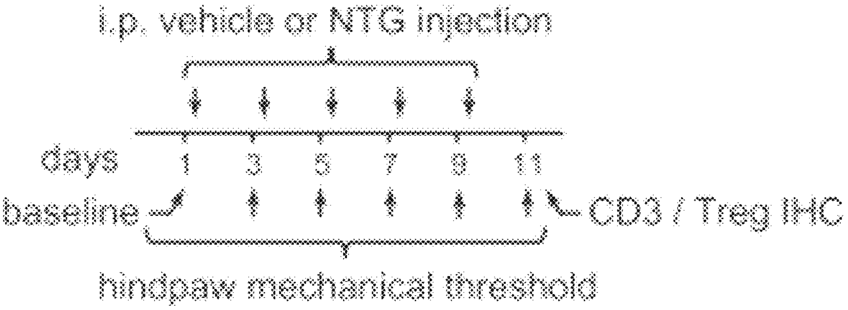

The present disclosure is based, at least in part, on the discovery that there is a deficiency in Treg-mediated homeostasis in the nervous system of subjects suffering from headache disorders and subjects with post traumatic neuropathic pain. As shown herein, there is a significant reduction in the ratio of Treg cells among total T cells in the trigeminal ganglion and dorsal root ganglion in various animal models of headache and neuropathic pain. The therapeutic agents which are capable of increasing the number of Tregs are useful for treating or preventing headache and neuropathic pain. For example, the use of low-dose interleukin-2 (ld-IL2) completely reversed the established behavioral readouts of hypersensitivity in models of chronic migraine, PTH, and MOH. Moreover, continuous ld-IL2 treatment prevented the development of NTG- and sumatriptan-induced mechanical hypersensitivity related to chronic migraine and MOH, respectively. The present disclosure thus provides compositions and methods for treating or preventing various headache disorders or neuropathic pain. The therapeutic strategy as described herein includes administering a and active agent capable of increasing Treg numbers in the subject, such as low dose of IL-2, rapamycin, statins, or the adoptive transfer of Tregs.

A composition of the disclosure may optionally comprise one or more additional drugs or therapeutically active agent in addition to the active agents described herein or Tregs. A composition of the disclosure may further comprise a pharmaceutically acceptable excipient, carrier, or diluent. Further, a composition of the disclosure may contain preserving agents, solubilizing agents, stabilizing agents, wetting agents, emulsifiers, salts (substances of the present invention may themselves be provided in the form of a pharmaceutically acceptable salt), buffers, coating agents, or antioxidants.

Other aspects and iterations of the invention are described more thoroughly below.

I. Compositions

For the first time, as described herein, compositions which effectively increase Treg numbers in a subject (e.g., ld-IL2, rapamycin, statin, administration or adoptive transfer of Tregs) constitutes an innovative therapeutic strategy for the prevention or treatment of chronic migraine, post-traumatic headache (PTH), medication overuse headache (MOH) and neuropathic pain.

Headache disorders, including chronic migraine, PTH, and MOH, are highly prevalent and debilitating. A substantial proportion of patients remains either unresponsive to current treatment options or intolerant to their side effects. There is an urgent need to understand the disease mechanisms and to develop safer and more effective therapies with mechanisms of action distinct from the existing approaches.

Activation of many proinflammatory immune cells, including meningeal mast cells, macrophages, dendritic cells, and T cells, has been implicated in the pathophysiology of migraine and PTH. On the contrary, little is known about the involvement of immunosuppressive regulatory T (Treg) cells in headache disorders, let alone their potential as a therapeutic target. Tregs are a specialized subpopulation of $CD4^{+}$ T cells that express high-level of transcription factor Foxp3 and the high-affinity interleukin-2 (IL2) receptor CD25. They possess far-ranging suppressive activity affecting the function of all types of immune cells with multiple mechanisms, therefore are widely implicated in the maintenance of immune homeostasis. Many clinical trials use repeated ld-IL2 treatment to selectively expand and activate Treg cells in vivo without activating effector T cells regardless of the disease background. Ld-IL2 is well tolerated in patients and shows indications of clinical efficacy. Chronic pain-associated Treg changes have been studied in mouse models of nerve injury and experimental autoimmune encephalomyelitis. Nerve injury reduces Treg cells in mouse spleen but increases Treg cell number in the injured nerve as well as the ipsilateral draining lymph node (LN), dorsal root ganglia (DRG), and dorsal horn of the spinal cord. Experimental autoimmune encephalomyelitis also results in Treg increases in the brain, spinal cord, LN, and spleen. In both disease models, cutaneous mechanical allodynia is exacerbated by the depletion of Treg cells and is attenuated by the increase in Treg cell number.

The present disclosure provides compositions useful for the treatment or prevention of headache disorders and neuropathic pain by increasing the number of T regulatory cells (Treg) in a subject. For example, as described herein, Id-IL2 treatment not only completely reversed NTG-induced facial skin hypersensitivity but also blocked the effects of subsequent NTG administrations through endogenous Treg cells. Importantly, ld-IL2 did not alter basal nociceptive responses or induce the development of tolerance. Ld-IL2 also effectively reversed the behavioral sensitization related to MOH and prevented the development of both acute and persistent PTH-related behaviors in a mouse model of mild traumatic brain injury (mTBI). Collectively, the present disclosure provides increasing Treg number as a promising therapeutic strategy for treating and preventing headache disorders and neuropathic pain with a mechanism of action distinct from the existing treatment approaches.

(a) Agent for increasing Treg numbers (i) IL-2

In some embodiments, the present disclosure provides a composition comprising IL-2 as an active agent for increasing Treg numbers in a subject. IL-2 is utilized exclusively for cancer immunotherapy, and has not been investigated in the treatment or prevention of headache disorders or neuropathic pain. Indeed, the capacity of IL-2 to stimulate Teffs carries the risk of activating the very effector T cells that mediate auto-immunity. The present disclosure provides evidence that IL-2 can be used under conditions that induce Tregs without altering the frequencies of $CD4^+$ and $CD3^+$ T cells.

As used herein, the term "IL-2" designates any source of IL-2, including mammalian sources such as e.g., human, mouse, rat, primate, and pig, and may be native or obtained by recombinant or synthetic techniques, including recombinant IL-2 polypeptides produced by microbial hosts. IL-2 may be or comprise the native polypeptide sequence, or can be an active variant of the native IL-2 polypeptide. Preferably the IL-2 polypeptide or active variant is derived from a human source, and includes recombinant human IL-2, particularly recombinant human IL-2 produced by microbial hosts. The nucleic acid and peptide sequence of IL-2 is known in the art and can be found in publically available databases including, e.g., UniProt accession number P60568, Entrez gene accession number 3558 or Genbank reference P60568. Active variants of IL-2 have been previously described. Variants of the native IL-2 can be fragments, analogues, and derivatives thereof. By "fragment" is intended a polypeptide comprising only a part of the intact polypeptide sequence. An "analogue" designates a polypeptide comprising the native polypeptide sequence with one or more amino acid substitutions, insertions, or deletions. Muteins and pseudopeptides are specific examples of analogues. "Derivatives" include any modified native IL-2 polypeptide or fragment or analogue thereof, such as glycosylated, phosphorylated, fused to another polypeptide or molecule, polymerized, etc., or through chemical or enzymatic modification or addition to improve the properties of IL-2 (e.g., stability, specificity, etc.). Active variants of a reference IL-2 polypeptide generally have at least 75%, preferably at least 85%, more preferably at least 90% amino acid sequence identity to the amino acid sequence of the reference IL-2 polypeptide. Methods for determining whether a variant IL-2 polypeptide is active are available in the art and are specifically described in the present disclosure with regards to Treg activation in the nervous system. An active variant is, most preferably, a variant that activates Tregs.

Examples of IL-2 variants are disclosed, for instance, in EP109748, EP136489, U.S. Pat. No. 4,752,585; EP200280, or EP118,617, included herein by reference in their entirety.

A recombinant IL-2 is an IL-2 that has been prepared by recombinant DNA techniques. The host organism used to express a recombinant DNA encoding IL-2 may be prokaryotic (a bacterium such as *E. coli*) or eukaryotic (e.g., a yeast, fungus, plant or mammalian cell). Processes for producing IL-2 have been described e.g., in U.S. Pat. Nos. 4,656,132; 4,748,234; 4,530,787; or U.S. Pat. No. 4,748,234, incorporated herein by reference. In some embodiments, the disclosure provides an IL-2 of human origin, or an active variant thereof, produced recombinantly.

IL-2 for use in the present disclosure shall be in essentially pure form, e.g., at a purity of 95% or more, further preferably 96, 97, 98 or 99% pure.

In some embodiments, IL-2 may be used in monomeric or multimeric form.

IL-2 is commercially available, including for pharmaceutical uses, and it is authorized for use in human patients. Suitable commercial forms include, e.g., Proleukin®, a recombinant, human IL-2 composition; Aldesleukin®, an unglycosylated des-alanyl-1, serine-125 human interleukin-2 produced in *E. coli*; and Roncoleukin®, recombinant human IL-2 produced in yeast. Interleukin-2 may be used alone or in combination with any other therapeutically active agent.

Administration of IL-2 may be measured by an increase in Treg counts in the subject, typically by 10% at least, or by an increase in activation markers such as the intensity of CD25 expression.

For use in the present disclosure, IL-2 is administered at a dosage which effectively increases Tregs numbers. The effective dosage can be adjusted by the practitioner, based on information contained in the present disclosure. In particular, with the knowledge of the present disclosure that, in patients with various headache disorders or neuropathic pain, IL-2 may be administered under conditions which do activate Tregs and which essentially do not activate effector T cells, the skilled person may be able to adjust dosages to each patient and condition. Typically IL-2 is administered at a dose of about 0.05 to about 2 MIU/m2/day, preferably 0.2 to about IMIU/m2/day. The amount of IL-2 to administer thus preferably depends on the body surface area of the subject. The body surface area (BSA) is the measured or calculated surface of a human body.

The treatment is typically repeated, i.e., the above low doses IL-2 are administered several times to a subject, to progressively achieve the most substantial benefit. The dose and schedule of administration vary according to the preventive or therapeutic aim of the treatment, as well as to the disease to be treated/prevented. Treatment effect can be monitored by Treg measurements and dose and administration schedule adjusted accordingly. Exemplary dosages are between 0.1 to 3 MIU, preferably 0.1 to 1.5 MIU, still preferably 0.25 to 1 MUI.

These dosages may be combined, depending on the subject and evolution of the disease. Treatment may be provided as courses of several days, e.g., 1-7 days of daily administration, preferably between 3 to 5 days. Such treatment courses may be reproduced at different time periods, interrupted by periods with no treatment. In a preventive setting, IL-2 may be administered at the above dosage in single shots, at different time intervals, e.g., once a week over long periods of time. Different protocols may be adjusted depending on the patient and disease.

Maintenance dosage can be administered from two to eight weeks after the initiating cycle is completed. Preferably the maintenance dose is the same as the initiating dose.

Generally speaking, IL-2 may be administered at a dose of D/10 to 20×D, preferably D/5 to IOxD, wherein D is the minimal dose triggering induction of expression of CD25 in Treg, without inducing expansion of Treg.

This method for determining the appropriate low-dose of IL-2 is particularly useful when a route of administration different from the subcutaneous route is contemplated. Especially such dosage may be useful in oral, nasal or rectal delivery. Determination of CD25 levels can be accomplished using anti-CD25 antibodies in flow cytometry.

In this regard, lymphocyte-containing samples may be fixed with a suitable fixing agent (e.g. paraformaldehyde, which may be used at 1% in phosphate-buffered saline (PBS)) to permit the subsequent quantification or qualitative determination of the cell surface marker (e.g. by the use of flow cytometry) as convenient (e.g. following transport from the site of collection and culture of the lymphocyte-containing sample, to a flow cytometry laboratory). Commercially available Anti-CD25 monoclonal antibodies (mAbs) labeled to different fluorochrome such as Alexa488 (Molecular Probes, Oregon, USA) and FITC (Sigma) are available.

(ii) Rapamycin

In some embodiments, the present disclosure provides a composition comprising rapamycin as an active agent for increasing Treg numbers in a subject. Irrespective of the state of art in the present field, for some applications far outside the scope and field of the present invention, rapamycin (also known as sirolimus) is a well-known pharmaceutical agent. Most notably, rapamycin has long been successfully used to minimize organ transplant rejection in humans, while seemingly countless other potential applications have also been postulated from time to time.

Rapamycin and its numerous analogs and derivatives (collectively known as "rapalogs") famously act to inhibit its namesake metabolic pathway in mammals—the mammalian target of rapamycin ("mTOR"). The critical metabolic roles of the mTOR pathway have long led to broad speculation about possible medical uses for rapamycin and rapalogs, in addition to rapamycin's well-known efficacy in reducing human organ transplant rejection. However, despite the success with prevention of transplant rejection, and despite the many long-felt needs and corresponding tremendous efforts in developing rapamycins for other indications, effective use of rapamycin or other rapalogs for treating or preventing other disorders has not been widely successful and has been very limited at best.

Rapamycin administration has been shown to selectively expand regulatory T cells, see, e.g., Battagalia, M et al. Methods in molecular biology (2011) 821:279-93 and R. Mao et al., Biochem Pharmacol, 85 (2013) 1513 1524, 10.1016/j.bcp.2013.03.013, both of which are herein incorporated by reference in their entirety. As described herein, preferentially increase Treg cells are effective in treating headache disorders and neuropathic pain, thus rapamycin and its functional analogs are useful in the methods described herein.

Rapamycin binds to a member of the FK binding protein (FKBP) family, FKBP 12. The rapamycin/FKBP 12 complex binds to the protein kinase mTOR to block the activity of signal transduction pathways. Because the mTOR signaling network includes multiple tumor suppressor genes, including PTEN, LKB1, TSC1, and TSC2, and multiple proto-oncogenes including P13K, Akt, and eEF4E, mTOR signaling plays a central role in cell survival and proliferation. Binding of the rapamycin/FKBP complex to mTOR causes arrest of the cell cycle in the G1 phase (Janus 2005).

Inhibitors of mTOR also include rapamycin analogs. Many rapamycin analogs are known in the art. Non-limiting examples of analogs of rapamycin include, but are not limited to, everolimus, tacrolimus, CC1-779, ABT-578, AP-23675, AP-23573, AP-23841, 7-epi-rapamycin, 7-thiomethyl-rapamycin, 7-epi-trimethoxyphenyl-rapamycin, 7-epi-thiomethyl-rapamycin, 7-demethoxy-rapamycin, 32-emethoxy-rapamycin, 2-desmethyl-rapamycin, and 42-O-(2-hydroxy)ethyl rapamycin.

For purposes of these descriptions, absent clear limitation otherwise, other analogs of rapamycin include: rapamycin oximes (U.S. Pat. No. 5,446,048); rapamycin aminoesters (U.S. Pat. No. 5,130,307); rapamycin dialdehydes (U.S. Pat. No. 6,680,330); rapamycin 29-enols (U.S. Pat. No. 6,677,357); O-alkylated rapamycin derivatives (U.S. Pat. No. 6,440,990); water soluble rapamycin esters (U.S. Pat. No. 5,955,457); alkylated rapamycin derivatives (U.S. Pat. No. 5,922,730); rapamycin amidino carbamates (U.S. Pat. No. 5,637,590); biotin esters of rapamycin (U.S. Pat. No. 5,504,091); carbamates of rapamycin (U.S. Pat. No. 5,567,709); rapamycin hydroxyesters (U.S. Pat. No. 5,362,718); rapamycin 42-sulfonates and 42-(N-carboalkoxy) sulfamates (U.S. Pat. No. 5,346,893); rapamycin oxepane isomers (U.S. Pat. No. 5,344,833); imidazolidyl rapamycin derivatives (U.S. Pat. No. 5,310,903); rapamycin alkoxyesters (U.S. Pat. No. 5,233,036); rapamycin pyrazoles (U.S. Pat. No. 5,164,399); acyl derivatives of rapamycin (U.S. Pat. No. 4,316,885); reduction products of rapamycin (U.S. Pat. Nos. 5,102,876 and 5,138,051); rapamycin amide esters (U.S. Pat. No. 5,118,677); rapamycin fluorinated esters (U.S. Pat. No. 5,100,883); rapamycin acetals (U.S. Pat. No. 5,151,413); oxorapamycins (U.S. Pat. No. 6,399,625); and rapamycin silyl ethers (U.S. Pat. No. 5,120,842).

For use in the present disclosure, rapamycin is administered at a dosage which effectively increases Tregs numbers. The effective dosage can be adjusted by the practitioner, based on information contained in the present disclosure. In particular, with the knowledge of the present disclosure that, in patients with various headache disorders or neuropathic pain, rapamycin may be administered under conditions which do activate Tregs, the skilled person may be able to adjust dosages to each patient and condition. Typically rapamycin is administered at a dose of about 1-5 mg/day.

The treatment is typically repeated, i.e., the above rapamycin doses are administered several times to a subject, to progressively achieve the most substantial benefit. The dose and schedule of administration vary according to the preventive or therapeutic aim of the treatment, as well as to the disease to be treated/prevented. Treatment effect can be monitored by Treg measurements and dose and administration schedule adjusted accordingly.

Treatment may be provided as courses of several days, e.g., 1-7 days of daily administration, preferably between 3 to 5 days. Such treatment courses may be reproduced at different time periods, interrupted by periods with no treatment. In a preventive setting, rapamycin may be administered at the above dosage in single shots, at different time intervals, e.g., once a week over long periods of time. Different protocols may be adjusted depending on the patient and disease.

Maintenance dosage can be administered from two to eight weeks after the initiating cycle is completed. Preferably the maintenance dose is the same as the initiating dose.

This method for determining the appropriate rapamycin is particularly useful when a route of administration different from the subcutaneous route is contemplated. Especially such dosage may be useful in oral, nasal or rectal delivery. Determination of CD25 levels can be accomplished using anti-CD25 antibodies in flow cytometry.

(iii) Statins

In some embodiments, the present disclosure provides a composition comprising a statin as an active agent for increasing Treg numbers in a subject. Statins are drugs that have been widely used to treat hypercholesterolemia in patients at high risk of developing atherosclerosis and have episodes of cardiovascular disease. Statins are potent cholesterol lowering agents that inhibit cholesterol biosynthesis in the liver and consequently have proved beneficial effects in the primary and secondary prevention of ischemic heart disease. These drugs inhibit the enzyme 3-hydroxy-3-methylglutaryl Coenzyme A reductase (HMG CoA reductase) (Essig, M et al., Circ. Res. 1998; 83:683-690), responsible for the conversion in the liver of HMG-CoA to mevalonic acid, the precursor of cholesterol, which results in a reduced levels of low density cholesterol (LDL) and other changes in lipid profile (Essig, M et al. 3-hydroxi-3-methylglutaryl coenzyme A reductase inhibitors increase fibrinolytic activity in rat aortic endothelial cells. Circ. Res. 1998; 83:683-690).

HMG CoA reductase responds to a negative feedback regulation given by the steroidal and nonsteroidal products of mevalonate metabolism, by decreasing the expression of the reductase gene. Statins reduce the cholesterol content of hepatocytes and increase the expression of LDL receptors by inhibiting HMG CoA reductase (Vaughan, C J. et al. The evolving role of statins in the management of atherosclerosis. J. Am. Coll. Cardiol. 2000; 35:1-10). These receptors are responsible for receptor-mediated endocytosis of LDL cholesterol, thus, decreasing the plasma level of circulating LDL.

The different types of statins such as atorvastatin, simvastatin, lovastatin, fluvastatin, pravastatin, among others, differ among themselves in absorption, plasma protein binding, excretion and solubility, exhibiting a wide dose-dependent efficacy in reducing LDL.

Statin administration has been shown to selectively expand regulatory T cells, see, e.g., R. Mao et al., Biochem Pharmacol, 85 (2013) 1513 1524,10.1016/j.bcp.2013.03.013. As described herein, preferentially increase Treg cells are effective in treating headache disorders and neuropathic pain, thus statins and their functional analogs are useful in the methods described herein.

For use in the present disclosure, a statin is administered at a dosage which effectively increases Tregs numbers. The effective dosage can be adjusted by the practitioner, based on information contained in the present disclosure. In particular, with the knowledge of the present disclosure that, in patients with various headache disorders or neuropathic pain, a statin may be administered under conditions which activate Tregs, the skilled person may be able to adjust dosages to each patient and condition. Typically the type of statin will influence the amount to be administered. For example simvastatin can be administered at a dose of about 10-40 mg/day, whereas lovastatin can be administered at a dose of about 5-80 mg/day.

The treatment is typically repeated, i.e., the above statin doses are administered several times to a subject, to progressively achieve the most substantial benefit. The dose and schedule of administration vary according to the preventive or therapeutic aim of the treatment, as well as to the disease to be treated/prevented. Treatment effect can be monitored by Treg measurements and dose and administration schedule adjusted accordingly.

Treatment may be provided as courses of several days, e.g., 1-7 days of daily administration, preferably between 3 to 5 days. Such treatment courses may be reproduced at different time periods, interrupted by periods with no treatment. In a preventive setting, a statin may be administered at the above dosage in single shots, at different time intervals, e.g., once a week over long periods of time. Different protocols may be adjusted depending on the patient and disease.

Maintenance dosage can be administered from two to eight weeks after the initiating cycle is completed. Preferably the maintenance dose is the same as the initiating dose.

This method for determining the appropriate statin dose is particularly useful when a route of administration different from the subcutaneous route is contemplated. Especially such dosage may be useful in oral, nasal or rectal delivery. Determination of CD25 levels can be accomplished using anti-CD25 antibodies in flow cytometry.

(iv) Other Active Agents for Increasing Treg Numbers

The present disclosure is not particularly limited to a specific active agent. Indeed, any active agent which is capable of increasing Treg numbers are useful in accordance with the present disclosure. In some embodiments, the composition of the disclosure comprises an active agent which increases the number of Treg cells in a subject. Stimulation in Tregs may be measured by an increase in Treg counts in the subject, typically by at least 10%, at least 20%, at least 30%, at least 40%, at least 50% at least 60%, or by an increase in activation markers such as the intensity of CD25 expression. A systematic evaluation of 640 FDA-approved drugs has identified more than 70 drugs that increases the number of Treg cells with suppression function in in vitro assays (R. Mao et al., Biochem Pharmacol, 85 (2013) 1513 1524,10.1016/j.bcp.2013.03.013). Thus, the active agents and doses thereof as described in R. Mao et al., Biochem Pharmacol, 85 (2013) 1513 1524,10.1016/j.bcp.2013.03.013 is incorporated herein, including the Treg-promoting drugs and doses which are useful according to the present disclosure. For example, TGFb1, sulfadoxine, tobramycin, spectinomycin, lomefloxacin, norflxacin, lincomycin, clinafloxacin, novobiocin, clindamycin, imipenem, tetracycline, tinidazole, terbinafine, meloxicam, tenoxicam, piroxicam, mefenamic acid, ketoprofen, ibuprofen, prednisone, prednisolone, methylprednisolone, dexamethasone, hydrocortisone, triamcinolone, medroxyprogesterone 17-acetate, terfenadine, temozolomide, toremifene, gefitinib, ribavirin, troglitazone, clomiphene, aminophylline, chloroquine, and retinoic acid were shown to be useful in increasing Treg numbers.

For use in the present disclosure, each composition comprising an active agent as noted above is administered at a dosage which effectively increases Tregs numbers. The effective dosage can be adjusted by the practitioner, based on information contained in the present disclosure. Moreover, the effective dosage can be the dosage commonly used for said active agent. In particular, with the knowledge of the present disclosure that, in patients with various headache disorders or neuropathic pain, a statin may be administered under conditions which increase Tregs numbers, the skilled person may be able to adjust dosages to each patient and condition.

(v) Treg Cells

In some embodiments, the present disclosure provides a composition comprising a population of Treg cells for increasing Treg numbers in a subject. Regulatory T cells are T lymphocytes having immunosuppressive activity. Natural Tregs are characterized as $CD4^{+}CD25^{+}$ $Foxp3^{+}$ cells. Humans and mice presenting a genetic deficit in Tregs develop multiple T-cell mediated organ-specific autoimmune diseases. A Treg quantitative or qualitative defect has been described in many human autoimmune diseases, including systemic lupus erythematosis (SLE), Type 1 Diabetes, Multiple Sclerosis, uveitis and myositis. Conversely, addition/restoration of Treg induces clinical improvements in most animal models of these diseases.

Tregs also play a major role in the control of inflammatory diseases, although their mode of action in such disease is not well understood. In fact, in most inflammatory diseases, Treg depletion exacerbates disease while Treg addition decreases it. This is for example shown in the context of atherosclerosis. Although this disease is not primarily an inflammatory disease, its development involves an inflammatory component/loop. In apolipoprotein E (ApoE) deficient mice that spontaneously develop atherosclerosis, Treg depletion significantly aggravated the plaque formation, while injection of polyclonal Tregs significantly improved the disease.

The present disclosure provides means of utilizing T regulatory cells for treatment or prevention of various headache disorders or neuropathic pain. In some embodiments, the disclosure provides the use of non-matched cord blood derived T regulatory cells for treatment or prevention of various headache disorders or neuropathic pain. The present invention includes compositions of expanded T regulatory cells (Tregs), according to the disclosure. The expanded cells retain a Treg phenotype following expansion and administration into a subject.

The invention provides compositions and methods for expanding Tregs. Accordingly, such an expansion methodology allows for the establishment of a cell population useful for treatment or prevention of various headache disorders or neuropathic pain. In one aspect, the present disclosure provides Treg expansion by isolating Tregs from a desired cell source and subsequently culture expanding the cells in the presence of a primary signal and a co-stimulatory signal. Agents useful for stimulating a primary signal and an a co-stimulatory signal on Tregs may be used in soluble form, attached to the surface of a cell, or immobilized on a surface as described herein. In some embodiments, both primary and co-stimulatory agents are co-immobilized on a surface, for example a bead or an engineered cell. In one embodiment, the molecule providing the primary activation signal, such as a CD3 ligand, and the co-stimulatory molecule, such as a CD28 ligand are coupled to or loaded on the same surface, for example, a particle or an engineered cell.

In another embodiment, the disclosure provides a method of expanding Tregs, to clinically useful numbers using a repetitive stimulation procedure. In one embodiment, the method of expanding Tregs comprises re-stimulating Tregs based upon cell size. Preferably, Tregs exhibiting a cell size about the size of a resting Treg are chosen for re-stimulation. In some instances, the size of a resting Treg is about 8.5 .mu.m. In another embodiment, the method of expanding Tregs comprises re-stimulating Tregs in the presence of Rapamycin. In some embodiments, Tregs isolated from peripheral blood of a subject are re-stimulated in the presence of Rapamycin. In some embodiments, the expanded cells of the invention maintain Foxp3 profile indicative of Tregs. In one embodiment, the population of expanded Tregs expresses specific natural Treg markers such as Foxp3 and Latency Associated Peptide (LAP), displayed Treg specific demethylation in the Foxp3 gene, and contain very few IL-2, IFNγ, IL-17 secreting cells. In other embodiments, at least a portion of the active cell population is stored for later implantation/infusion. The population may be divided into more than one aliquot or unit such that part of the population of Tregs is retained for later application while part is applied immediately to the subject. Moderate to long-term storage of all or part of the cells in a cell bank is also within the scope of this disclosure.

Generation of Treg cells for use within the context of the disclosure may be performed by numerous means known in the art, which are incorporated by reference. For example, U.S. Patent Application No. 20100310588 discloses methods for producing autoantigen-specific regulatory T cells and methods for use of same. According to the teachings of 20100310588, T cells are derived from a subject or from a donor, $CD25^{+}CD4^{+}$ T regulatory (Treg) cells are selected by immuno-selection and cell sorting, the Treg cells are expanded ex vivo by the use of a TCR/CD3 activator (e.g. anti-CD3 antibody), a TCR costimulator activator (e.g. anti-CD28 antibody) and IL-2 and the expanded population of Treg cells are adoptively transferred to a subject for treatment of autoimmune responses (e.g. diabetes, GVHD, Lupus, etc.). U.S. Patent Application No. 20100260781 provides methods and compositions for expanding T regulatory cells ex vivo or in vivo using one or more serum amyloid P (SAP) agonists (e.g. SAP polypeptide). According to their teachings, the use of SAP agonists enriches for regulatory T cells and thus promotes regulatory T cell-mediated suppression of autoimmune disorders or conditions (e.g. diabetes, graft rejection, GVHD, etc.). U.S. Patent Application No. 20100092488 provides methods for increasing the number of regulatory T cells by inhibiting midkine (MK). 20100092488 further provides methods for treatment or prevention of diseases (e.g. autoimmune diseases such as diabetes, lupus etc.) associated with the functional disorder of regulatory T cells comprising the administration of a midkine inhibitor. U.S. Patent Application No. 20090142308 provides methods for treating autoimmune diseases (e.g. diabetes) by inducing autoantigen-specific regulatory $CD4^{+}$ T cells. According to the teachings of 20090142308, treating an autoimmune disease is effected by first administering to the subject a composition comprising an autoantigen (e.g. insulin) and an oil-and-water adjuvant. Next, a blood sample comprising PBMCs is obtained from the subject and autoantigen-specific regulatory T cells are isolated therefrom. The autoantigen-specific regulatory T cells may then be expanded ex vivo to obtain an adequate amount of cells for treatment and the autoantigen-specific regulatory T cells are then administered back to a subject. PCT Publication No. 2010/017220 discloses methods of expanding and enriching a regulatory T-cell population by contacting a leukocytes population having antigen-presenting cells with a granulocyte-macrophage colony stimulating factor (GMCSF), interleukin-3 (IL-3) and/or interleukin-5 (IL-5). The regulatory T cells disclosed therein may be used for suppressing naive T-cells in a subject and subsequently for the treatment of autoimmune diseases.

In one embodiment, Treg cells are generated by means that are known in various laboratories and routinely used. Any method of cell isolation may be used according to the present teachings. One exemplary method of isolation of regulatory cells from peripheral blood comprises centrifugation, with or without a gradient (e.g. Percoll gradient). This technique separates cells based upon density. Another exemplary method which may be used comprises panning and immunomagnetic isolation, using molecules immobilized to surface or magnetic beads, respectively, as for example, antibodies that recognize and bind molecules on the cell surface (e.g. CD4, CD8, CD20, etc.). Molecules immobilized to a surface or conjugated to magnetic beads recognize and bind to one or more of the cell specific surface markers of a particular cell type. Cells that possess one or more cell surface markers are bound by the immobilized molecules or exposure of the bead-conjugated cells to a magnetic field, allowing any other cell to be washed away. In positive selection procedures the cell type of interest is retained, and in negative selection procedures cell type of interest is purged. Another isolation procedure which are used according to the present teachings includes fluorescence activated cell sorting (FACS). Antibodies with fluorescent tags may be used to bind to the cells of interest. The antibodies bind to the cell surface molecules (e.g. CD4, CD8, CD20, etc.), and a FACS sorter may then sort and collect the cells based upon the fluorescence observed. The cells that display certain fluorescence may then be isolated. Following isolation of the immune regulatory cells, the cells may be further cultured, expanded and/or stimulated. Ex vivo expansion of isolated immune regulatory cells include, for example, the protocol for T regulatory cells: cells are cultured with CD3/CD28 stimulation (e.g. anti-CD3 antibody and anti-CD28 antibody) in the presence of high IL-2 concentrations, IL-10 and stimulation/education with dendritic cells. Ex vivo expansion of the cells as described herein (i.e. with an antigen presenting cell) may also selectively enrich for antigen-specific immune regulatory cells. It will be appreciated that the immune regulatory cells may also be expanded in vivo in order to increase the number of these cells prior to isolation and ex vivo manipulation.

In some embodiments, Treg cells are expanded from cord blood. Protocols are known in the art for generation of clinically relevant numbers of cord blood derived Treg cells. Several examples are given below. "Fresh" CB (fresh is defined as processed within 48 hr of cord blood draw) can be collected as cord blood units (CBUs) containing 35 mL of citrate phosphate dextrose (CPD) anticoagulant. CBUs (n=11) which are processed for isolation of cord blood mononuclear cells (CBMCs) by density gradient centrifugation (Ficoll-Paque PLUS, GE Healthcare). CBUs are thawed and resuspended in 60 mL of dextran-HSA wash solution (divided into two 50-mL conical tubes), allowed to warm to room temperature, and underlaid with 15 mL Ficoll-Paque PLUS per conical tube for density gradient centrifugation and CBMC isolation. One protocol for Treg expansion is performed using FACS-isolated cells that are plated according. Antigen presenting cells (APC) were prepared from KT64/86, a K562-derived cell line constitutively expressing high-affinity Fc receptor, CD64, and CD86 for co-stimulation. Fc-binding receptors on KT64/86 were precleared of serum immunoglobulins by culture in serum-free medium (SFM) overnight and then irradiated at 10,000 rad. Anti-CD3 (clone OKT-3, Miltenyi Biotec) monoclonal antibody (mAb) was loaded on KT64/86 at 1 μg/$10^6$ cells at 4° C. for 30 min, washed twice with SFM, and cryopreserved in CryoStor CS10 (BioLife Solutions). After Treg FACS purification (described above), KT64/86 APCs are added to culture at a 1:1 aAPC-to-Treg cell ratio. CB Tregs and cryoCB Tregs can be expanded in complete RPMI 1640 (cRPMI)-consisting of RPMI 1640 (Life Technologies) supplemented with 10% FBS (Atlanta Biologicals), 1 M HEPES, 1 mM sodium pyruvate, 100× minimum essential medium (MEM) non-essential amino acid solution, 50 mM 2-mercaptoethanol (2-ME), and 100 U penicillin/streptomycin (Gibco)-plus 600 IU/mL Proleukin (human recombinant IL-2 [hrIL-2], Prometheus Laboratories). Tregs can then be expanded in cRPMI plus 300 IU/mL Proleukin (hrIL-2, Prometheus Laboratories). On day 2, the culture volume is doubled, and IL-2 is added (at the aforementioned concentrations, assuming consumption). Cells are resuspended, and fresh medium and IL-2 were added on days 4, 6, 8, 11, and 13. On day 9, cells are restimulated with Dynabeads (human T-activator CD3/CD28 for T cell expansion and activation, Dynal Invitrogen) at a 1:1 ratio. Another protocol involves FACS-isolated cells that are plated evenly at 2.5×10 4 to 5.0×10 4 Tregs/well in a 96-well flat-bottom plate (Costar) and activated with anti-CD3/anti-CD28-coated microbeads (MACS GMP ExpAct Treg kit for research use, Miltenyi Biotec) at a 4:1 bead-to-cell ratio. CB Tregs and cryoCB Tregs are expanded in cRPMI plus 600 IU/mL Proleukin (hrIL-2, Prometheus Laboratories). APB Tregs are expanded in cRPMI plus 300 IU/mL Proleukin (hrIL-2, Prometheus Laboratories). On day 2, the culture volume is doubled, and fresh IL-2 is added (at the aforementioned concentrations, assuming consumption). Cells are resuspended, and fresh medium and IL-2 is added on days 4, 6, 8, 11, 13, 15, 17, 20, 22, 24, and 26, assuming consumption. On days 9 and 18, cells are restimulated with fresh anti-CD3/anti-CD28-coated beads at a 1:1 ratio.

Another protocol involves use of FACS-isolated cells that are plated and activated with Dynabeads at a 4:1 bead-to-cell ratio. Cells are cultured either in X-VIVO 15 or in X-VIVO 15 customized by Lonza by substituting 100% of the glucose in the base medium with D-glucose (6,6-2H2, 99%) (Cambridge Isotope Laboratories, catalog no. DLM-349-MPT) supplemented with 10% human heat-inactivated pooled APB serum. On day 2, the culture volume was doubled, and IL-2 was added (300 IU/mL, Proleukin). Cells were resuspended, and fresh medium and IL-2 were added (600 IU/mL, Proleukin) on days 5, 7, 12, and 14, assuming consumption. On day 9, cells were restimulated with additional Dynabeads at a 1:1 ratio.

For all generation of Treg it is important that final release criteria is followed. In one example, final release criteria involves cells being assessed for purity (≤5% CD8+ cells, <100 beads/3×10 6 cells, and endotoxin ≤3.5 endotoxin units [EU]/mL), phenotype (≥95% CD4+ cells and ≥60% FOXP3+), sterility (negative for *Mycoplasma*, anaerobic and aerobic bacteria, gram stain, fungal culture, potassium hydroxide [KOH] exam), and viability (≥85%).

Previous studies have demonstrated that mesenchymal stem cells (MSC) are capable of producing growth factors associated with cellular proliferation such as FGF, VEGF, IGF-1 and HGF. In fact MSC feeder layers have previously been used to expand hematopoietic, and pluripotent, stem cells while maintaining these cells in an undifferentiated state. Furthermore, MSC have been demonstrated to promote generation of Treg cells in vitro, and in vivo. In one embodiment of the disclosure Treg are expanded by culture with MSC in vitro. In one embodiment, MSC are generated according to protocols previously utilized for treatment of patients utilizing bone marrow derived MSC. Specifically, bone marrow is aspirated (10-30 ml) under local anesthesia (with or without sedation) from the posterior iliac crest, collected into sodium heparin containing tubes and transferred to a Good Manufacturing Practices (GMP) clean room. Bone marrow cells are washed with a washing solution such as Dulbecco's phosphate-buffered saline (DPBS), RPMI, or PBS supplemented with autologous patient plasma and layered on to 25 ml of Percoll (1.073 g/ml) at a concentration of approximately 1-2×$10^7$ cells/ml. Subsequently the cells are centrifuged at 900 g for approximately 30 min or a time period sufficient to achieve separation of mononuclear cells from debris and erythrocytes. Said cells are then washed with PBS and plated at a density of approximately 1×$10^6$ cells per ml in 175 cm 2 tissue culture flasks in DMEM with 10% FCS with flasks subsequently being loaded with a minimum of 30 million bone marrow mononuclear cells. The MSCs are allowed to adhere for 72 h followed by media changes every 3-4 days. Adherent cells are removed with 0.05% trypsin-EDTA and replated at a density of 1×$10^6$ per 175 $cm^2$. Said bone marrow MSC may be administered intravenously, or in a preferred embodiment, intrathecally in a patient suffering radiation associated neurodegenerative manifestations. Although doses may be determined by one of skill in the art, and are dependent on various patient characteristics, intravenous administration may be performed at concentrations ranging from 1-10 million MSC per kilogram, with a preferred dose of approximately 2-5 million cells per kilogram.

The present disclosure also provides pharmaceutical compositions. The pharmaceutical composition comprises a plurality of Tregs, as an active component, and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

Compositions comprising the presently disclosed Tregs can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the Tregs in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin. According to the presently disclosed subject matter, however, any vehicle, diluent, or additive used would have to be compatible with the Tregs.

The compositions can be isotonic, i.e., they can have the same osmotic pressure as blood and lacrimal fluid. The desired isotonicity of the compositions may be accomplished using sodium chloride, or other pharmaceutically acceptable agents such as dextrose, boric acid, sodium tartrate, propylene glycol or other inorganic or organic solutes. Sodium chloride can be particularly for buffers containing sodium ions.

Viscosity of the compositions, if desired, can be maintained at the selected level using a pharmaceutically acceptable thickening agent. For example, methylcellulose is readily and economically available and is easy to work with. Other suitable thickening agents include, for example, xanthan gum, carboxymethyl cellulose, hydroxypropyl cellulose, carbomer, and the like. The concentration of the thickener can depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

The quantity of cells to be administered will vary for the subject being treated. In a one embodiment, between about $10^4$ and about $10^{10}$, between about $10^5$ and about $10^9$, or between about $10^6$ and about 108 of the presently disclosed Tregs are administered to a human subject. More effective cells may be administered in even smaller numbers. In certain embodiments, at least about $1\times10^8$, about $2\times10^8$, about $3\times10^8$, about $4\times10^8$, or about $5\times10^8$ of the presently disclosed Tregs are administered to a human subject. In certain embodiments, between about $1\times10^7$ and $5\times10^8$ of the presently disclosed Tregs are administered to a human subject. The precise determination of what would be considered an effective dose may be based on factors individual to each subject, including their size, age, sex, weight, and condition of the particular subject. Dosages can be readily ascertained by those skilled in the art from this disclosure and the knowledge in the art.

The skilled artisan can readily determine the amount of cells and optional additives, vehicles, and/or carrier in compositions and to be administered in methods. Typically, any additives (in addition to the active cell(s) and/or agent(s)) are present in an amount of 0.001 to 50% (weight) solution in phosphate buffered saline, and the active ingredient is present in the order of micrograms to milligrams, such as about 0.0001 to about 5 wt %, about 0.0001 to about 1 wt %, about 0.0001 to about 0.05 wt % or about 0.001 to about 20 wt %, about 0.01 to about 10 wt %, or about 0.05 to about 5 wt %. For any composition to be administered to an animal or human, the followings can be determined: toxicity such as by determining the lethal dose (LD) and $LD_{50}$ in a suitable animal model e.g., rodent such as mouse; the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

Compositions comprising the presently disclosed Tregs can be provided systemically or directly to a subject for treating or preventing a headache disorder or neuropathic pain. In certain embodiments, the presently disclosed Tregs or compositions comprising thereof are directly injected into an organ of interest. Alternatively, the presently disclosed Tregs or compositions comprising thereof are provided indirectly to the organ of interest, for example, by administration into the circulatory system. Expansion and differentiation agents can be provided prior to, during or after administration of the cells or compositions to increase Treg cell activation, or proliferation, in vitro or in vivo.

The presently disclosed Tregs can be administered in any physiologically acceptable vehicle, normally intravascularly. Usually, at least a population of about $1\times10^5$ cells will be administered, eventually reaching about $1\times10^{10}$ or more. The presently disclosed Tregs can comprise a purified population of cells. Those skilled in the art can readily determine the percentage of the presently Tregs in a population using various well-known methods, such as fluorescence activated cell sorting (FACS). Suitable ranges of purity in populations comprising the presently disclosed CAR-DCs are about 50% to about 55%, about 5% to about 60%, and about 65% to about 70%. In certain embodiments, the purity is about 70% to about 75%, about 75% to about 80%, or about 80% to about 85%. In certain embodiments, the purity is about 85% to about 90%, about 90% to about 95%, and about 95% to about 100%. Dosages can be readily adjusted by those skilled in the art (e.g., a decrease in purity may require an increase in dosage). The cells can be introduced by injection, catheter, or the like.

The presently disclosed compositions can be pharmaceutical compositions comprising the presently disclosed Tregs and a pharmaceutically acceptable carrier. Administration can be autologous or heterologous. For example, CAR-DCs, or progenitors can be obtained from one subject, and administered to the same subject or a different, compatible subject. Peripheral blood derived Tregs (e.g., in vivo, ex vivo or in vitro derived) can be administered via localized injection, including catheter administration, systemic injection, localized injection, intravenous injection, or parenteral administration. When administering a therapeutic composition of the presently disclosed subject matter (e.g., a pharmaceutical composition comprising a presently disclosed Tregs), it can be formulated in a unit dosage injectable form (solution, suspension, emulsion).

(b) Components of the Composition

The present disclosure also provides pharmaceutical compositions. The pharmaceutical composition comprises an active agent as described herein or a population of Tregs, as an active ingredient, and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

(i) Diluent

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

(ii) Binder

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, oligopeptides, and combinations thereof.

(iii) Filler

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

(iv) Buffering Agent

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

(v) pH Modifier

In various embodiments, the excipient may be a pH modifier. By way of non-limiting example, the pH modifying agent may be sodium carbonate, sodium bicarbonate, sodium citrate, citric acid, or phosphoric acid.

(vi) Disintegrant

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

(vii) Dispersant

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

(viii) Excipient

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

(ix) Lubricant

In a further embodiment, the excipient may be a lubricant. Non-limiting examples of suitable lubricants include minerals such as talc or silica; and fats such as vegetable stearin, magnesium stearate, or stearic acid.

(x) Taste-Masking Agent

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

(xi) Flavoring Agent

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

(xii) Coloring Agent

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C). The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The composition can be formulated into various dosage forms and administered by a number of different means that will deliver a therapeutically effective amount of the active ingredient. Such compositions can be administered orally (e.g. inhalation), parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, intra-articular, or intrasternal injection, or infusion techniques. Formulation of drugs is discussed in, for example, Gennaro, A. R., Remington's Pharmaceutical Sciences, Mack Publishing Co., Easton, Pa. (18th ed, 1995), and Liberman, H. A. and Lachman, L., Eds., Pharmaceutical Dosage Forms, Marcel Dekker Inc., New York, N.Y. (1980). In a specific embodiment, a composition may be a food supplement or a composition may be a cosmetic.

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof. For administration by inhalation, the compounds are delivered in the form of an aerosol spray from pressured container or dispenser which contains a suitable propellant, e.g., a gas such as carbon dioxide, or a nebulizer.

For parenteral administration (including subcutaneous, intradermal, intravenous, intramuscular, intra-articular and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules, and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols, or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles, and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising a compound of Formula (I) is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers, and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of a compound of Formula (I) in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, the compound of Formula (I) may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying an active agent may be prepared by any known method of preparing liposomes for drug delivery, such as, for example, detailed in U.S. Pat. Nos. 4,241,046; 4,394,448; 4,529,561; 4,755,388; 4,828,837; 4,925,661; 4,954,345; 4,957,735; 5,043,164; 5,064,655; 5,077,211; and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar liposomes.

As would be apparent to one of ordinary skill, all of the parameters that govern liposome formation may be varied. These parameters include, but are not limited to, temperature, pH, concentration of the active agent, concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The active agents may be encapsulated in a microemulsion by any method generally known in the art.

In yet another embodiment, an active agent as described herein may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

II. Methods

As disclosed herein, the present disclosure provides methods of treating or preventing headache disorders or neuropathic pain. In an aspect, the present disclosure provides methods of treating a headache disorder or neuropathic pain, the method generally comprising, administering an active agent which increases Treg numbers in the subject. For example, as described herein, administration of a low dose of IL-2 increases the frequency of Treg cells in the subject and thereby reduces or prevents a symptom of the headache or neuropathic pain. In another aspect, the present disclosure provides methods of treating a headache disorder or neuropathic pain, the method generally comprising, administering and effective amount of Treg cells to the subject. Suitable compositions for use in the methods of the present disclosure are disclosed herein, for instance those described in Section I.

As described herein, active agents increasing Treg numbers (e.g., ld-IL2 treatment) prevent and/or treat the chronification of migraine and other headache disorders. Repeated injections of nitroglycerin (NTG, a nitric oxide [NO] donor and a reliable trigger of migraine in patients) resulted in a 50% reduction of the ratio of Treg cells among $CD3^+$ T cells in mouse trigeminal ganglia (TG), suggesting that chronic migraine is associated with a deficiency in Treg-mediated immune homeostasis. Ld-IL2 treatment not only completely reversed NTG-induced facial skin hypersensitivity but also blocked the effects of subsequent NTG administrations through endogenous Treg cells. Importantly, ld-IL2 did not alter basal nociceptive responses or induce the development of tolerance. Ld-IL2 also effectively reversed the behavioral sensitization related to MOH and prevented the development of both acute and persistent PTH-related behaviors in a mouse model of mild traumatic brain injury (mTBI). Thus, the present methods provide Treg cell as a promising target for treating chronic migraine and ld-IL2 as a safe and effective treatment for multiple headache disorders with a mechanism of action distinct from the existing treatment approaches.

As described herein, a headache disorder includes but is not limited to migraine, tension-type headache, cluster headache, medication-overuse headache, and trauma induced acute or chronic headaches. For example, presented herein are methods for treatment of headache, including migraine, e.g. acute treatment of migraine with or without aura, comprising administering the compositions presented herein.

In a particular aspect, provided herein are methods of treating headache, comprising administering low dose IL-2 or adoptively transferring Treg cells to a subject in need thereof.

In certain embodiments, the headache treated by the methods provided herein is a cluster headache, chronic daily headache, or migraine, including adult migraine or pediatric migraine. The migraine can be migraine with aura or migraine without aura. In particular embodiments, the methods presented herein are methods for treatment of a subject (e.g., a human subject) having a headache disorder. In other embodiments, the methods presented herein are methods for chronic treatment of a headache disorder.

"Treating," as used herein, refers to the amelioration of at least one symptom of the disorder being treated. Thus, the methods of treating headache or neuropathic pain, presented herein ameliorate at least one symptom of the headache or neuropathic pain. In certain embodiments, the methods of treating headache or neuropathic pain, presented herein reduce at least one symptom of the headache or neuropathic pain. In other embodiments, the methods of treating headache or neuropathic pain, presented herein eliminate at least one symptom of the headache or neuropathic pain. In some embodiments, the methods including preventing headache or neuropathic pain. As used herein, "preventing" refers to as preventing the occurrence of at least one symptom of the headache or neuropathic pain. An "effective dose" or "effective amount" as used herein, means an amount which provides a therapeutic or prophylactic benefit.

The term "therapeutic effect" as used herein, refers to a biological effect which can be manifested by a decrease ameliorate at least one symptom of the headache or neuropathic pain.

Symptoms of headache, e.g., cluster headache, chronic daily headache or migraine, include pain. Symptoms of migraine can also include, for example, nausea, vomiting, photophobia, phonophobia, osmophobia (aversion to, or hypersensitivity to, odors), vertigo, and/or allodynia. In certain embodiments, the methods of treating headache, for example migraine, presented herein ameliorate at least one such symptom of the headache, for example migraine. In particular embodiments, the methods of treating headache, for example migraine, presented herein reduce at least one such symptom of the headache, for example migraine. In other particular embodiments, the methods of treating headache, for example migraine, presented herein eliminate at least one such symptom of the headache, for example, migraine.

The term "neuropathic pain" as used herein has its conventional meaning and has been defined by the International Association for the Study of Pain (IASP, 2011) as 'Pain caused by a lesion or disease of the somatosensory nervous system'. The IASP further specifies: 'Neuropathic pain is a clinical description (and not a diagnosis) which requires a demonstrable lesion or a disease that satisfies established neurological diagnostic criteria. The presence of symptoms or signs (e.g., touch-evoked pain) alone does not justify the use of the term neuropathic. Some disease entities, such as trigeminal neuralgia, are currently defined by their clinical presentation rather than by diagnostic testing. Other diagnoses such as post-herpetic neuralgia are normally based upon the history.

Neuropathic pain can be divided according to the IASP in two different pain states:

1. Central neuropathic pain, defined by the IASP as 'pain caused by a lesion or disease of the central somatosensory nervous system'; and
2. Peripheral neuropathic pain, defined by the IASP as 'pain caused by a lesion or disease of the peripheral somatosensory nervous system'.

In specific embodiments, the methods of treating headache or neuropathic pain ameliorates at least one of pain, nausea, phonophobia or photophobia. In other specific embodiments, such methods ameliorate at least two, three or all four of said symptoms.

In some embodiments, the headache or neuropathic pain has a severity of more than about any of 1, 2, 3, 4, 5, 6, 7, 8, 9, or 10 on a scale of 0 to 10. In certain embodiments, the methods of treating a headache or neuropathic pain presented herein ameliorate at least one symptom of a headache or neuropathic pain having a severity of more than about any of 1, 2, 3, 4, 5, 6, 7, 8, 9, or 10 on a scale of 0 to 10. In certain embodiments, the methods of treating headache or neuropathic pain presented herein reduce the severity of a headache or neuropathic pain, for example a migraine, having a severity of more than about any of 1, 2, 3, 4, 5, 6, 7, 8, 9, or 10 on a scale of 0 to 10.

In certain embodiments, the intensity of headache pain or neuropathic pain, can be measured according to a 4-point severity scale (0=no pain, 1=mild, 2=moderate, 3=severe). In certain embodiments, the methods of treating headache or neuropathic pain, presented herein reduce the severity of headache pain, for example pain associated with migraine, by at least one point on such a 4-point severity scale.

In certain embodiments, the methods of treating migraine presented herein ameliorate at least one symptom of the migraine, e.g., ameliorate at least one of pain, nausea, phonophobia, or photophobia. The symptom or symptoms can, for example, be evaluated via a four point severity scale as follows: 0=none 1=mild symptom, not interfering with normal daily activities 2=moderate symptom, causing some restriction to normal activities 3=severe, leading to inability to perform normal daily activities. Alternatively, or additionally, a symptom or symptoms, including the four listed above, can be evaluated via a four-point functional disability scale that assesses the level of impairment a symptom has on a patient's ability to perform usual daily activities, as follows: 0=not at all impaired 1=slightly impaired 2=moderately impaired 3=severely or completely impaired.

In certain embodiments, the methods of treating headache or neuropathic pain presented herein ameliorate at least one symptom of the headache or neuropathic pain within 10, 15, 20, 25, 30 or 45 minutes, within 1, 2, 3, 4, 5, 6, 7, 8, 9, 10, 12, or 24 hours. In other embodiments, the methods of treating headache or neuropathic pain presented herein ameliorate at least one symptom of the headache or neuropathic pain within 1 or 2 days of administering a composition presented herein. In particular embodiments, methods of treating headache or neuropathic pain presented herein the amelioration of at least one symptom of the headache is sustained for about 3, 4, 5, 6, 8, 12, 18, 36, 48 hours, or 1, 2, 3, 4, 5, or 6 days.

Thus, aspects of the present disclosure is a method for treating a subject in need thereof. The terms "treat," "treating," or "treatment" as used herein, refers to the provision of medical care by a trained and licensed professional to a subject in need thereof. The medical care may be a diagnostic test, a therapeutic treatment, and/or a prophylactic or preventative measure. The object of therapeutic and prophylactic treatments is to prevent or slow down (lessen) an undesired physiological change or disease/disorder. Beneficial or desired clinical results of therapeutic or prophylactic treatments include, but are not limited to, alleviation of symptoms, diminishment of extent of disease, stabilized (i.e., not worsening) state of disease, a delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the disease, condition, or disorder as well as those prone to have the disease, condition or disorder or those in which the disease, condition or disorder is to be prevented.

Methods described herein are generally performed on a subject in need thereof. A subject in need of the therapeutic methods described herein can be a subject having, diagnosed with, suspected of having, or at risk for a headache disorder or neuropathic pain. A determination of the need for treatment will typically be assessed by a history, physical exam, or diagnostic tests consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and humans or chickens. For example, the subject can be a human subject.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; the activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4th ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of therapy disclosed herein can occur as a single event or over a time course of treatment. For example, the therapy can be administered daily, weekly, bi-weekly, or monthly. For more chronic conditions, treatment could extend from several weeks to several months or years.

Treatment in accord with the methods described herein can be performed prior to, concurrent with, or after conventional treatment modalities for headache or neuropathic pain.

A therapy as disclosed herein can be administered simultaneously or sequentially with another agent. Simultaneous administration can occur through the administration of separate compositions, each containing one or more of an IL-2/Treg therapy and another agent. Simultaneous administration can occur through the administration of one composition containing two or more of an IL-2/Treg therapy.

The administration of Tregs or a population of Tregs of the present disclosure of the present disclosure be carried out by aerosol inhalation, injection, ingestion, transfusion, implantation or transplantation. The Treg compositions described herein, may be administered to a patient subcutaneously, intradermally, intratumorally, intranodally, intramedullary, intramuscularly, by intravenous or intralymphatic injection, or intraperitoneally. In one embodiment, the cell compositions of the present disclosure are preferably administered by intravenous injection.

As noted above, the administration of Treg cells or a population of CAR-DCs can consist of the administration of $10^4$-$10^9$ cells per kg body weight, preferably $10^5$ to $10^6$ cells/kg body weight including all integer values of cell numbers within those ranges. The Tregs or a population of Tregs can be administrated in one or more doses. In another embodiment, the effective amount of Tregs or a population of Tregs are administrated as a single dose. In another embodiment, the effective amount of cells are administered as more than one dose over a period time. Timing of administration is within the judgment of a health care provider and depends on the clinical condition of the patient. The Tregs or a population of Tregs may be obtained from any source, such as a blood bank or a donor. While the needs of a patient vary, determination of optimal ranges of effective amounts of a given Tregs population(s) for a particular disease or conditions are within the skill of the art. An effective amount means an amount which provides a therapeutic or prophylactic benefit. The dosage administered will be dependent upon the age, health and weight of the patient recipient, type of concurrent treatment, if any, frequency of treatment, and the nature of the effect desired.

III. Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to the active agent as disclosed herein and delivery systems. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium or video. Detailed instructions may not be physically associated with the kit; instead, a user may be directed to an Internet web site specified by the manufacturer or distributor of the kit.

A control sample or a reference sample as described herein can be a sample from a healthy subject or from a randomized group of subjects. A reference value can be used in place of a control or reference sample, which was previously obtained from a healthy subject or a group of healthy subject. A control sample or a reference sample can also be a sample with a known amount of a detectable compound or a spiked sample.

The methods and algorithms of the invention may be enclosed in a controller or processor. Furthermore, methods and algorithms of the present invention, can be embodied as a computer implemented method or methods for performing such computer-implemented method or methods, and can also be embodied in the form of a tangible or non-transitory computer readable storage medium containing a computer program or other machine-readable instructions (herein "computer program"), wherein when the computer program is loaded into a computer or other processor (herein "computer") and/or is executed by the computer, the computer becomes an apparatus for practicing the method or methods. Storage media for containing such computer program include, for example, floppy disks and diskettes, compact disk (CD)-ROMs (whether or not writeable), DVD digital disks, RAM and ROM memories, computer hard drives and back-up drives, external hard drives, "thumb" drives, and any other storage medium readable by a computer. The method or methods can also be embodied in the form of a computer program, for example, whether stored in a storage medium or transmitted over a transmission medium such as electrical conductors, fiber optics or other light conductors, or by electromagnetic radiation, wherein when the computer program is loaded into a computer and/or is executed by the computer, the computer becomes an apparatus for practicing the method or methods. The method or methods may be implemented on a general purpose microprocessor or on a digital processor specifically configured to practice the process or processes. When a general-purpose microprocessor is employed, the computer program code configures the circuitry of the microprocessor to create specific logic circuit arrangements. Storage medium readable by a computer includes medium being readable by a computer per se or by another machine that reads the computer instructions for providing those instructions to a computer for controlling its operation. Such machines may include, for example, machines for reading the storage media mentioned above.

GENERAL TECHNIQUES

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as Molecular Cloning: A Laboratory Manual, second edition (Sambrook, et al., 1989) Cold Spring Harbor Press; Oligonucleotide Synthesis (M. J. Gait, ed. 1984); Methods in Molecular Biology, Humana Press; Cell Biology: A Laboratory Notebook (J. E. Cellis, ed., 1989) Academic Press; Animal Cell Culture (R. I. Freshney, ed. 1987); Introduction to Cell and Tissue Culture (J. P. Mather and P. E. Roberts, 1998) Plenum Press; Cell and Tissue Culture: Laboratory Procedures (A. Doyle, J. B.

Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); DNA Cloning: A practical Approach, Volumes I and II (D. N. Glover ed. 1985); Nucleic Acid Hybridization (B. D. Hames & S. J. Higgins eds. (1985; Transcription and Translation (B. D. Hames & S. J. Higgins, eds. (1984»; Animal Cell Culture (R. I. Freshney, ed. (1986; Immobilized Cells and Enzymes (IRL Press, (1986; and B. Perbal, A practical Guide To Molecular Cloning (1984); F. M. Ausubel et al. (eds.).

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term “about,” as used herein, refers to variation of in the numerical quantity that can occur, for example, through typical measuring techniques and equipment, with respect to any quantifiable variable, including, but not limited to, mass, volume, time, distance, and amount. Further, given solid and liquid handling procedures used in the real world, there is certain inadvertent error and variation that is likely through differences in the manufacture, source, or purity of the ingredients used to make the compositions or carry out the methods and the like. The term “about” also encompasses these variations, which can be up to ±5%, but can also be ±4%, 3%, 2%, 1%, etc. Whether or not modified by the term “about,” the claims include equivalents to the quantities.

When introducing elements of the present disclosure or the preferred aspects(s) thereof, the articles “a,” “an,” “the,” and “said” are intended to mean that there are one or more of the elements. The terms “comprising,” “including,” and “having” are intended to be inclusive and mean that there may be additional elements other than the listed elements.

The terms “patient,” “subject,” “individual,” and the like are used interchangeably herein, and refer to any animal or cells thereof whether in vitro or in situ, amenable to the methods described herein. In certain non-limiting embodiments, the patient, subject or individual is a human.

As used herein, the term “subject” refers to a mammal, preferably a human. The mammals include, but are not limited to, humans, primates, livestock, rodents, and pets. A subject may be waiting for medical care or treatment, may be under medical care or treatment, or may have received medical care or treatment.

The term “transformation” refers to the transfer of a nucleic acid fragment into the genome of a host cell, resulting in genetically stable inheritance. Host cells containing the transformed nucleic acid fragments are referred to as “transgenic” cells, and organisms comprising transgenic cells are referred to as “transgenic organisms”.

“Transformed,” “transgenic,” and “recombinant” refer to a host cell or organism such as a bacterium, cyanobacterium, animal, or a plant into which a heterologous nucleic acid molecule has been introduced. The nucleic acid molecule can be stably integrated into the genome as generally known in the art and disclosed (Sambrook 1989; Innis 1995; Gelfand 1995; Innis & Gelfand 1999). Known methods of PCR include, but are not limited to, methods using paired primers, nested primers, single specific primers, degenerate primers, gene-specific primers, vector-specific primers, partially mismatched primers, and the like. The term “untransformed” refers to normal cells that have not been through the transformation process.

“Wild-type” refers to a virus or organism found in nature without any known mutation.

Design, generation, and testing of the variant nucleotides, and their encoded polypeptides, having the above-required percent identities and retaining a required activity of the expressed protein is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. Thus, one skilled in the art could generate a large number of nucleotide and/or polypeptide variants having, for example, at least 50-99% identity to the reference sequence described herein and screen such for desired phenotypes according to methods routine in the art.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2, or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

Generally, conservative substitutions can be made at any position so long as the required activity is retained. So-called conservative exchanges can be carried out in which the amino acid which is replaced has a similar property as the original amino acid, for example, the exchange of Glu by Asp, Gln by Asn, Val by Ile, Leu by Ile, and Ser by Thr. For example, amino acids with similar properties can be Aliphatic amino acids (e.g., Glycine, Alanine, Valine, Leucine, Isoleucine); Hydroxyl or sulfur/selenium-containing amino acids (e.g., Serine, Cysteine, Selenocysteine, Threonine, Methionine); Cyclic amino acids (e.g., Proline); Aromatic amino acids (e.g., Phenylalanine, Tyrosine, Tryptophan); Basic amino acids (e.g., Histidine, Lysine, Arginine); or Acidic and their Amide (e.g., Aspartate, Glutamate, Asparagine, Glutamine). Deletion is the replacement of an amino acid by a direct bond. Positions for deletions include the termini of a polypeptide and linkages between individual protein domains. Insertions are introductions of amino acids into the polypeptide chain, a direct bond formally being replaced by one or more amino acids. An amino acid sequence can be modulated with the help of art-known computer simulation programs that can produce a polypeptide with, for example, improved activity or altered regulation. On the basis of this artificially generated polypeptide sequences, a corresponding nucleic acid molecule coding for such a modulated polypeptide can be synthesized in-vitro using the specific codon-usage of the desired host cell.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature (Tm) of a DNA duplex between the two sequences. If a particular duplex has a melting temperature lower than 65° C. in the salt conditions of a 6×SSC, then the two sequences will not hybridize. On the other hand, if the melting temperature is above 65 □C in the same salt conditions, then the sequences will hybridize. In general, the melting temperature for any hybridized DNA:DNA sequence can be determined using the following formula: Tm=81.5° C.+16.6(log 10[Na+])+0.41 (fraction G/C content)−0.63(% formamide)−(600/l). Furthermore, the Tm of a DNA:DNA hybrid is decreased by 1-1.5□C for every 1% decrease in nucleotide identity (see e.g., Sambrook and Russel, 2006).

Host cells can be transformed using a variety of standard techniques known to the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

Exemplary nucleic acids which may be introduced to a host cell include, for example, DNA sequences or genes from another species, or even genes or sequences which originate with or are present in the same species, but are incorporated into recipient cells by genetic engineering methods. The term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the cell, DNA from another individual of the same type of organism, DNA from a different organism, or a DNA generated externally, such as a DNA sequence containing an antisense message of a gene, or a DNA sequence encoding a synthetic or modified version of a gene.

Host strains developed according to the approaches described herein can be evaluated by a number of means known in the art (see e.g., Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

As various changes could be made in the above-described materials and methods without departing from the scope of the invention, it is intended that all matter contained in the above description and in the examples given below, shall be interpreted as illustrative and not in a limiting sense.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Low-Dose Interleukin-2 and Adoptive Treg Transfer Prevents and Treats Multiple Headache Disorder Models Headache disorders are highly prevalent and debilitating, with limited treatment options. Headache disorders are among the most common disorders of the nervous system. Many proinflammatory immune cells contribute to headache pathophysiology lending to the complexity of effectively treating these disorders.

The present Example shows that repeated nitroglycerin (NTG, a reliable trigger of migraine in patients) administration doubles the number of CD31 T cells in the trigeminal ganglia without altering the number of Treg cells, suggesting a deficiency in Treg-mediated immune homeostasis. Mice treated with low-dose interleukin-2 (ld-IL2) to preferentially expand and activate endogenous Treg cells. This not only prevented the development of NTG-induced persistent sensitization but also completely reversed the established facial skin hypersensitivity resulting from repeated NTG administration. The effect of ld-IL2 was independent of mouse sex and/or strain. Importantly, ld-IL2 treatment did not alter basal nociceptive responses, and repeated usage did not induce tolerance. The therapeutic effect of ld-IL2 was abolished by Treg depletion and was recapitulated by Treg adoptive transfer. Furthermore, treating mice with ld-IL2 1 to 7 days after mild traumatic brain injury effectively prevented as well as reversed the development of behaviors related to acute and chronic post-traumatic headache. In a model of medication overuse headache, ld-IL2 completely reversed the cutaneous hypersensitivity induced by repeated administration of sumatriptan.

Collectively, this study identifies ld-IL2 as a promising prophylactic for multiple headache disorders with a mechanism distinct from the existing treatment options.

Methods

All procedures were performed in strict accordance with the recommendations in the Guide for the Care and Use of Laboratory Animals of the National Institutes of Health and were approved by the Institutional Animal Care and Use Committee at Washington University in St. Louis. To avoid social isolation stress, all mice were group housed (2-5 per cage, same sex) in the animal facility of Washington University in St. Louis on a 12-hour light-dark cycle with constant temperature (23-24° C.), humidity (45%-50%), and food and water ad libitum. All experiments were performed during the light phase (9 AM-4 PM). Adult mice (8-14 weeks old, both male and female) were used in the experiments. Adult Swiss Webster mice were purchased from Charles River. Adult C57BL/6J mice and the breeders of DEREG (depletion of regulatory T cell, 32050 JAX) mice were purchased from the Jackson Laboratory. The DEREG mice contain a transgenic allele that expresses the diphtheria toxin receptor-enhanced green fluorescent protein (DTR-EGFP) fusion protein under the control of the genomic sequences that regulate the expression of endogenous foxp3. Heterozygous DEREG mice were generated by crossing the DEREG breeder with C57BL/6J mice. The genotype was determined by polymerase chain reaction of tail DNA. The DTR-EGFP transgenic allele was amplified with the forward primer (5'-CCTACGGCGTGCAGTGCTTCAGCCGC-3') (SEQ ID NO:1) and the reverse primer (5'-CGGCGAGCTGCACGCTGCCGTCCTC-3')(SEQ ID NO: 2), producing a 300-bp fragment. The polymerase chain reaction conditions were 96° C. for 30 seconds, 60° C. for 30 seconds, and 72° C. for 30 seconds for 33 cycles. Of note, DEREG mice were used as a reporter line for $Foxp3^+$ Treg cells, not for depletion of Treg cells in this study.

Mouse model of chronic migraine and drug treatments: After measuring baseline nociceptive responses, mice received repetitive intraperitoneal (i.p.) injections of NTG (10 mg/kg in saline with 1% propylene glycol) or vehicle (saline with 1% propylene glycol in saline, 10 mL/kg) every 2 days for 4 or more times as described previously (Pradhan A A, et al. PAIN 2014; 155:269-74). Nocifensive behaviors were measured 2 days after each injection (before the next treatment). NTG (SDM27; Copperhead Chemical, Tamaqua, PA) was freshly diluted from the stock (10% in propylene glycol, aliquoted in airtight glass vials and stored at 4° C.) with saline for every injection. Recombinant mouse IL2 (carrier-free; Biolegend, San Diego, CA) was freshly diluted from the stock (1 mg/mL aliquots at 280° C.) every day. Each mouse received daily i.p. injection of 1-mg IL2 in 100-mL saline. The control mice received daily i.p. injections of 100-mL saline. In Treg depletion experiment, mice received 1 i.p. injection of antibodies against CD25 (500 mg/mouse, BP0012; BioXcell, West Lebanon, NH11) or control IgG (BP0088; BioXcell). The antibody binds to CD25 on Treg cell membrane and depletes Treg cells through Fcg receptor III-mediated antibody-dependent cellular cytotoxicity and antibody-dependent cellular phagocytosis (Setiady Y Y, et al, Eur J Immunol 2010; 40:780-6). Note that on the days that the mouse behaviors were tested, NTG, IL2 and/or antibodies were always injected after completing the behavioral tests.

Mouse model of mild traumatic brain injury-induced post-traumatic headache. Adult Swiss Webster mice (30-35 g) were subjected to mTBI using a modified closed head weight-drop method. 43, 58 Briefly, mice were anesthetized with 3% isoflurane for 90 seconds and were placed chest down on a foam sponge (4-cm thickness and 0.062-g/cm3 density) directly underneath a hollow cylindrical tube (1.5-cm inner diameter) placed approximately 1 cm vertically over the mouse's head. To induce mTBI, a 30-g weight (1.3-cm diameter and 3.4-cm height) was dropped through the tube from a height of 80 cm, striking the center point between the ears once. All mice regained righting reflex within 2 minutes. No mortality, skull fracture, or motor deficit was observed in any mice. Sham mice were anesthetized with 3% isoflurane for 90 seconds but not subjected to the weight drop. Facial mechanical thresholds were measured before and at various time points after mTBI. Daily ldIL2 or saline were administered 1 or 7 days after the sham or mTBI procedure. To reveal mTBI-induced hyperalgesia priming, mice received daily i.p. injections of NTG (0.1 mg/kg, i.p.) for 4 to 6 days, starting at 35 days after mTBI. Facial mechanical thresholds were measured between day 35 and 43 days after mTBI. Note that on the days that the mouse behaviors were tested, NTG and/or IL2 were always injected after completing the behavioral tests.

Mouse model of medication overuse headache. After measuring baseline nociceptive responses, mice received daily i.p. injections of sumatriptan succinate (0.6 mg/kg; Fresenius Kabi, Lake Zurich, IL44). Daily ld-IL2 or saline were administered after mice received 2 sumatriptan injections. Facial and hindpaw mechanical thresholds were measured every 2 days. Note that on the days that the mouse behaviors were tested, sumatriptan and/or IL2 were always injected after completing the behavioral tests.

Behavioral tests. Mice were extensively handled by the experimenters for 2 weeks and were well-habituated to the test room and the test apparatus before each experiment. The experimenters were blinded to the treatments mice received during data collection and analysis.

Open-field test. Mice were habituated in the testing room for 1 hour in their home cages and then tested one at a time. Each mouse was placed in the center of the dimly illuminated, sound-attenuated VersaMax Open Field box (42 3 42 cm; AccuScan Instruments, Columbus, OH) for 1 hour while the experimenter left the room. Horizontal movement and center entries (14 3 14 cm) were recorded and analyzed by the VersaMax software.

Rotarod test. Motor coordination was assessed with the rotarod test 6 days after mTBI. Male mice were habituated in the testing room for 1 hour in their home cages and then underwent 5 training sessions on the Rotarod (Model 7650; Ugo Basile, Trappe, PA) at 4 revolutions/min (rpm) for 5 minutes. Mice that stayed on the rod for at least 2 minutes/session were tested on the accelerating rod (4-40 rpm over 5.5 minutes). The latency to fall from the rod was averaged over 3 trials in individual mice.

Adhesive removal test. The adhesive removal test was used to assess mTBI-induced sensory and motor deficits related to the paw and the mouth. The mouse was habituated in a testing box (28.5×17.5×12 cm) for 60 seconds. Two pieces of adhesive tape strips (0.3×0.4 cm; Topcare, Elk Grove Village, IL) were applied with equal pressure on each forepaw to cover the glabrous skin. Tape removal time was defined as the time between the mouse's first reaction to the presence of the tape, either by shaking its paw or bringing its paw to its mouth, and the complete removal of the adhesive strip from the forepaw. Male mice underwent 3 training sessions on post-mTBI day 11 and 2 test sessions the next day. The tape removal times of the left and right forepaws from the 2 test sessions were averaged in individual mice.

Responses to mechanical stimuli on the hindpaw. Mice were habituated in individual clear plexiglass boxes (11×11×15 cm) for 1 to 2 hours. A series of calibrated von Frey filaments was used to apply mechanical stimuli to the plantar surface of the hindpaws. The up-down paradigm was used to determine the 50% withdrawal threshold. The thresholds for both hindpaws were averaged to yield a single value for each mouse.

Cheek acetone test. The acute nocifensive response to acetone-evoked evaporative cooling on mouse cheek was measured as previously described (Constandil L, et al. J Pain 2012; 13:579-89). The day before testing, both cheeks were shaved (6.5×12 mm) under brief anesthesia (2% isoflurane in 100% oxygen). On the test day, mice were habituated in individual plexiglass cylinders (11-cm diameter, 15-cm height) situated in front of 3-way mirrors for 1 to 2 hours. Acetone (12 mL) was applied to the shaved cheeks and immediately returned mice to the cylinders. Time spent wiping the treated area was recorded by a video camera and quantified offline. For individual mice, acetone was applied alternatingly to both cheeks at 10-minute intervals, and the duration of behavior was averaged from 4 applications.

Withdrawal responses to facial mechanical stimuli. The hair on mouse forehead (above and between 2 eyes) was shaved the day before testing. On the test day, the experimenter gently held the mouse on the palm with minimal restraint and applied the calibrated von Frey filament perpendicularly to the shaved skin, causing the filament to bend for 5 seconds. A positive response was determined by the following criteria as previously described: mouse vigorously stroked its face with the forepaw, head withdrawal from the stimulus, or head shaking (Elliott M B et al., Headache 2012; 52:966-84). The up-down paradigm was used to determine the 50% withdrawal threshold.

Blood, spleen, and cervical lymph node cell preparation, antibody staining, flow cytometry, and enzyme-linked immunosorbent assay (ELISA). Adult male DEREG and C57BL/6J mice received 15 daily injections of saline or IL2. About 100-mL blood was collected from each mouse by submandibular bleeding. Mice used for blood collection were not used in the behavioral tests. Spleen and cervical LN tissues were ground and filtered through a sterile 70-mm cell strainer. After lysis of red blood cells (420301; Biolegend), cells were pelleted and resuspended for antibody staining, ELISA, and ELISPOT assay. Live cells were counted by the Vi-CELL Automated Cell Viability Analyzer (Beckman, Chaska, MN).

About $2\times10^6$ suspension cells were stained with the following antibodies from Biolegend that recognizes mouse CD3e (clone 145-2C11), CD4 (clone GK1.5 and RM4-5), CD8 (clone 53-6.7), and CD25 (clone PC61). The percentages of individual cell phenotypes were determined using flow cytometric analysis. Data were collected with FACScan (Becton Dickinson, Franklin Lakes, NJ) and analyzed with CellQuest Pro (Becton Dickinson) and Rainbow X Alias (Cytek) softwares. Table 1 summarizes the markers and assays used to define T-cell subsets in this study.

To quantify interferon g (IFNγ) secretion, splenocytes were plated in 24-well plates (5 3 106 per well) and stimulated with antiCD3 and anti-CD28 antibodies (1 and 5 mg/mL) in 1 mL complete RPMI1640 media overnight. IFNγ in the supernatants were quantified by ELISA (430901; Biolegend).

ELISPOT assay was performed to determine the number of INFg-secreting cells. Splenocytes were plated at $5\times10^4$ cells per well and incubated overnight with RPMI1640 media containing anti-CD3 and anti-CD28 antibodies (500 and 5 mg/mL) for stimulation. IFNg was detected using a colorimetric reagent kit (R&D SEL485 and SEL002). Following development, images were captured and analyzed on the ImmunoSpot7.0 plate reader (Cellular Technologies, Kennesaw, GA).

Isolation and adoptive transfer of Treg cells and $CD25^-$ $CD4^+$ T cells. Adult C57BL/6J mice (8 to 12 weeks old) received daily injections of IL2 for 12 days. $CD25^+CD4^+$ Treg cells and $CD25^-CD4^+$ cells were isolated from splenocytes through $CD4^+$ T-cell-negative selection followed by a $CD25^+$ T-cell-positive selection using EasySep mouse CD41 T-cell pre-enrichment and CD25-positive selection kits (18783; Stem Cell Technologies, Cambridge, MA). Adult male C57BL/6J mice (8-14 weeks old) received i.p. injections of 10-mg/kg NTG every 2 days. One day after the second NTG injection, mice were injected with $1\times10^6$ Treg or $CD25^-CD4^+$ cells through the tail vein. The 50% withdrawal threshold to facial mechanical stimuli was measured before the first NTG injection and 2 days after each NTG injections.

Tissue preparation, immunohistochemistry, and image analysis. Mice were euthanized with i.p. injection of barbiturate (200 mg/kg) and were transcardially perfused with warm 0.1 M phosphate buffered saline (pH 7.2) followed by cold 4% formaldehyde in 0.1 M phosphate buffer (pH 7.2) for fixation. Trigeminal ganglia, lumbar L4 DRG, and the tissues containing the cervical/medullary dorsal horn (from obex to C3 cervical spinal cord) were collected and sectioned at 15 mm in the transverse plane, collected on Superfrost Plus glass slides in sequence and stored at 220° C.

One in every 4 TG, DRG or cervical/medullary dorsal horn sections were processed for each immunohistochemistry experiment as described previously (Huang D, et al. PAIN 2016; 157:1744-60). The dura was carefully dissected from the skull using forceps and stained as whole mount. T cells were identified by the rat anti-CD3 antibody (clone 17A2, 1:200; eBioscience, San Diego, CA), and Treg cells were identified with the chicken anti-EGFP (1:1000; AVES Lab, Tigard, OR) antibody in tissues from DEREG mice. AlexaFluor 568- or 488-conjugated secondary antibodies (Invitrogen) were used at 1:1000 dilution. Immunofluorescence was observed through a 403 objective on a Nikon TE2000S-inverted epifluorescence microscope, and images were captured with a CoolSnapHQ2 camera (Photometrics, Tucson, AZ). To quantify CD31 T cells and Treg cells on the dura, we took random, nonoverlapping images (10 per mouse) in areas adjacent to the middle meningeal artery (MMA). To quantify T cells and Treg cells in TG, DRG, and cervical/medullary dorsal horn, all cells on individual sections were counted, and the number was multiplied by 4 to obtain the total number of cells per ganglion in each mouse. Images of individual sections were captured by an Olympus NanoZoomer WholeSlide Imaging System and measured with the SimplePCI software (Hamamatsu) to verify that the total areas of the sections quantified were comparable between individual mice. Representative images were adjusted for contrast and brightness using the same parameter within individual experiments. No other manipulations were made to the images. Image analysis was performed with experimenters blinded to the experimental groups.

Statistical analysis. For behavioral experiments, power analysis was conducted to estimate sample size with 0.80% power to reach a significance level of 0.05. The experimenters were blinded to the treatments mice received. For flow cytometry, ELISA and immunohistochemistry experiments, sample sizes were estimated based on our previous experience.

All data are reported as mean+/−SE of the mean. The Shapiro-Wilk test was used to check data normality. Statistical significance between experimental groups with normally distributed data was assessed by two-tailed t test, analysis of variance (1-way or 2-way, with or without repeated measures) with the post hoc Bonferroni test where appropriate, using Origin and Statistica softwares (from OriginLab and StatSoft, respectively). The nonparametric Mann-Whitney U test, Friedman test, or Kruskal-Wallis analysis of variance on ranks with multiple comparisons (Student-Newman-Keuls method) was used to analyze the differences in the withdrawal threshold to mechanical stimuli. Differences with $P<0.05$ were considered statistically significant. The statistical analysis for individual experiments was described in figure legends.

Figure 1B:
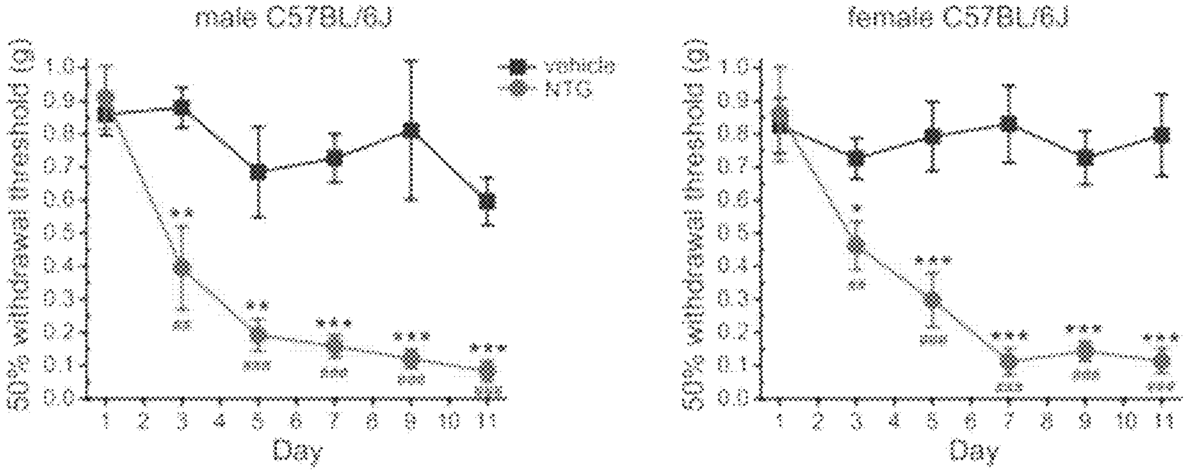

Results (ii) Repeated NTG Treatment Reduces the Ratio of Treg Cells to Total T Cells in Mouse Trigeminal Ganglia To mimic the high-frequency recurring headache in chronic migraine patients, male and female C57BL/6J inbred mice were treated with NTG (10 mg/kg, i.p.) or vehicle every 2 days for 5 times and measured the 50% withdrawal thresholds to von Frey filaments on the hindpaws 2 days after each injection (FIG. 1A). Compared with the baseline thresholds, repetitive NTG injections induced a progressive and sustained mechanical hypersensitivity on the hindpaw of both male and female mice (FIG. 1B), consistent with the previous study. Two days after the last NTG or vehicle injection, whole-mount dura was stained as well as the TG and L4 DRG sections with the CD3 antibody to label all T cells. The density of CD3+ T cells in the dura surrounding the MMA or in L4 DRG was not altered by the repeated NTG treatment (FIGS. 1C and 1D). By contrast, the abundance of CD31 cells was nearly doubled in the TG of NTG-treated mice (FIGS. 1D and 1E). There were on average 2176±288 and 4135±562 CD3+ cells per TG from vehicle- and NTG-treated mice (n=6/group, same mice as in FIG. 1D), indicating that repeated NTG administration preferentially increases the density of total T cells in mouse TG.

Next, it was examined whether repeated NTG treatment alters the number of Treg cells in mouse TG, using the DEREG transgenic mice, which specifically express the DTR-EGFP fusion protein in Treg cells. Flow cytometric analysis showed that EGFP signal was present in 85±2% CD4+CD25+ splenocytes from adult DEREG mice (n=4). It was verified that NTG-induced hindpaw mechanical hypersensitivity was not affected by the expression of DTR-EGFP in DEREG mice (FIG. 1F inset). The total number of EGFP+ Treg cells was very low in TG and DRG from vehicle treated mice (~30 and 6 per ganglion, respectively), and neither was significantly altered by the repetitive NTG injections (FIG. 1F). Because TG from NTG-treated mice contained twice as many CD3+ cells than those from vehicle-treated mice, the proportion of Treg cells among total T cells in TG was significantly reduced by the repeated NTG administration. Suggesting that chronic migraine is associated with a deficiency in Treg-mediated immune homeostasis.

(iii) Daily Ld-IL2 Prevents the Development of NTG-Induced Skin Hypersensitivity It has been documented that ld-IL2 treatment selectively expands and activates Treg cells in both mice and humans. Male DEREG mice were treated with daily ld-IL2 (1 □g/mouse, i.p.) or saline for 15 days. The frequency of EGFP+ Treg cells in the peripheral blood increased by more than 100% after 5 ld-IL2 injections (FIG. 2A), similar to the magnitude of ld-IL2-induced Treg expansion reported in human clinical trials (Hartemann A, et al., Lancet Diabetes Endocrinol 2013; 1:295-305; and Rosenzwajg M, et al., Ann Rheum Dis 2019; 78:209-17). The abundance of Treg cells in the blood was maintained by the subsequent IL2 injections (FIG. 2A). The percentage of EGFP+ Treg cells also increased significantly in the cervical LNs that receive all the lymph from the head and neck (FIG. 2B). CD25 was also used as the marker for Treg cells and saw similar ld-IL2-induced increase in the blood and LN (FIGS. 2C and 2D).

Figures 2E, 2F:
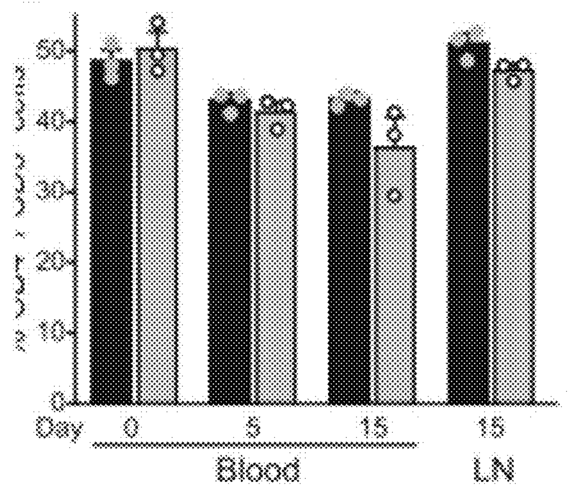
Figure 3A:
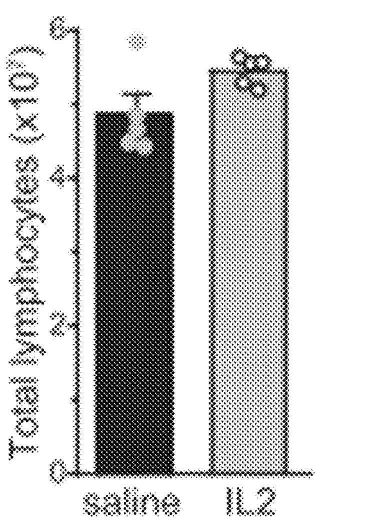
FIG. 3A-3G show analysis of splenocytes from mice treated with daily saline or ld-IL2.
Figure 3B:
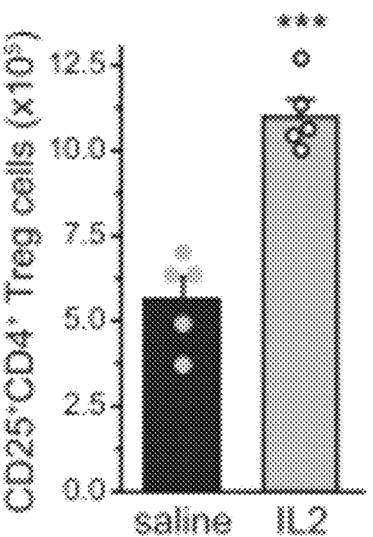
Figure 3C:
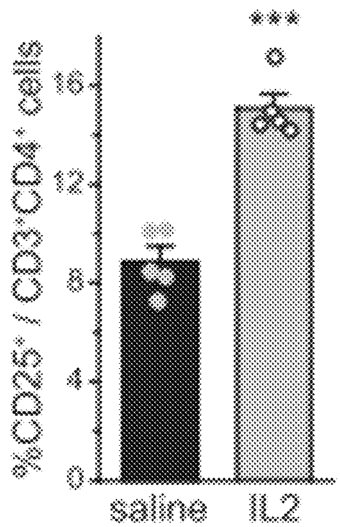
Figure 3D:
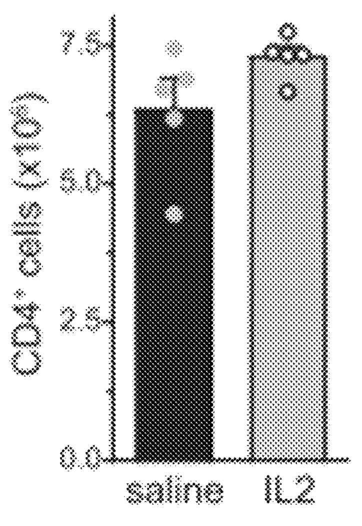
Figure 3E:
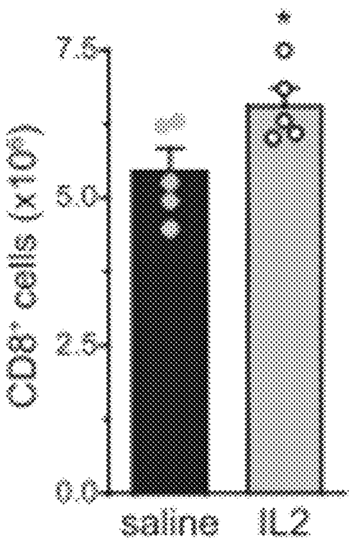
Figure 3F:
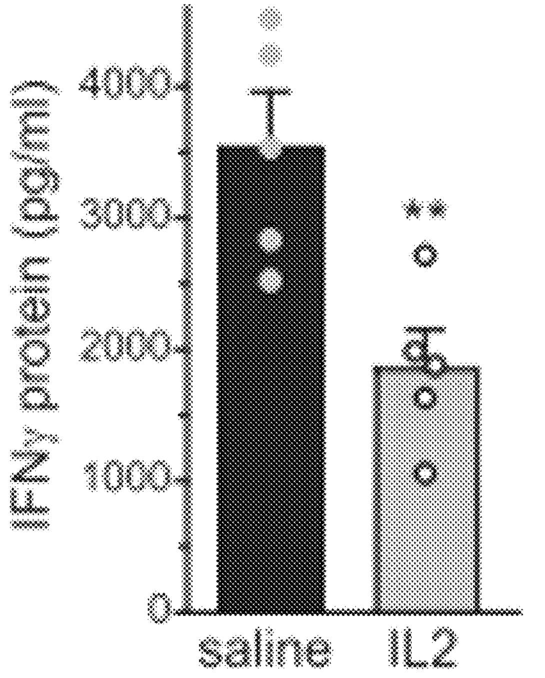
Figure 3G:
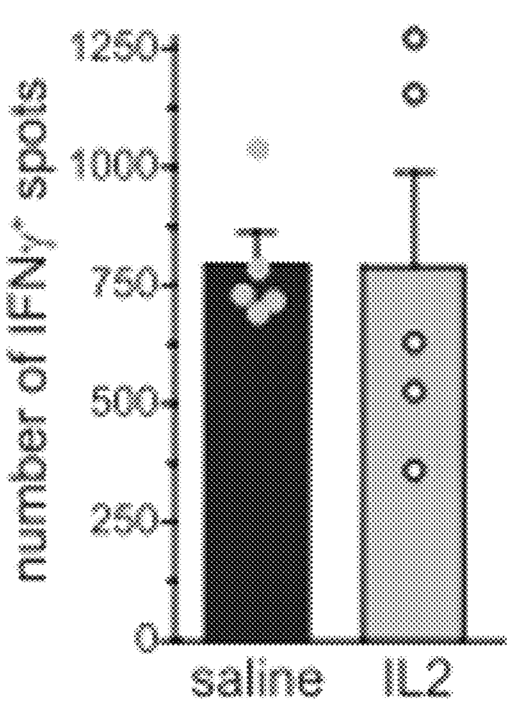

Conversely, the frequencies of CD4+ and CD3+ T cells in the blood or LNs were not altered by the ld-IL2 treatment (FIGS. 2E and 2F and Table 1). In wild-type C57BL/6J males, 15 days of ld-IL2 treatment doubled the number and the frequency of CD25+CD4+ Treg cells in the spleen (FIGS. 3A-3C), whereas the number of CD8+ cells increased only slightly (FIGS. 3D and 3E). The number of splenocytes secreting IFN□□was not altered but the amount of CD3/CD28 stimulation-induced IFN□ secretion was significantly reduced in cells from IL-2-treated mice (FIGS. 3F and 3G, Table 1). These data confirmed that daily ld-IL2 treatment preferentially increases Treg cells in the blood, LNs, and spleen, enhancing immunosuppression in mice.

Male C57BL/6J mice were treated with daily saline or ld-IL2, starting 5 days before the first NTG injection and continuing throughout the experiment (FIG. 4A). Basal hindpaw mechanical sensitivity was not altered by either 5 or 15 days of ld-IL2 injections (FIG. 4B, vehicle 1 saline vs vehicle 1 IL2). Conversely, NTG-induced hindpaw mechanical hypersensitivity was completely blocked by the ld-IL2 pretreatment (FIG. 4B, NTG+saline vs NTG+IL2).

In addition to increasing hindpaw mechanical sensitivity, repeated NTG administration also enhances the behavioral responses to acetone-induced cooling of facial skin in mice, and this can be blocked by the daily treatment with topiramate, a migraine preventive drug in humans. After measuring baseline responses to acetone-induced cooling, injected female C57BL/6J mice were repeatedly with NTG and measured the duration of acetone-induced face wiping 2 days after each injection (FIG. 4A). Compared with the vehicle group, there was a persistent increase in the duration of acetone-induced cheek wiping in NTG-treated mice (FIG. 4C, vehicle 1 saline vs NTG 1 saline). Pretreatment with ld-IL2 did not change the basal responses to acetone-induced cooling (FIG. 4C, vehicle 1 saline vs vehicle 1 IL2)

but prevented the development of NTG-induced facial cold hypersensitivity (FIG. 4C, NTG+saline vs NTG+IL2). Suggesting that ld-IL2 pretreatment can effectively prevent the development of repetitive NTG-induced skin hypersensitivity without compromising the baseline responses to mechanical or cold stimuli.

As in C57BL/6J females, repetitive NTG induced a gradual increase in the duration of acetone-induced cheek wiping in the outbred female Swiss Webster mice (FIG. 4D). Here, daily ld-IL2 treatment was started after mice received 2 NTG injections, but before the facial cold hypersensitivity was fully established (FIG. 4D). The delayed ld-IL2 treatment also blocked the development of facial cold hypersensitivity (FIG. 4D).

Figure 5A:
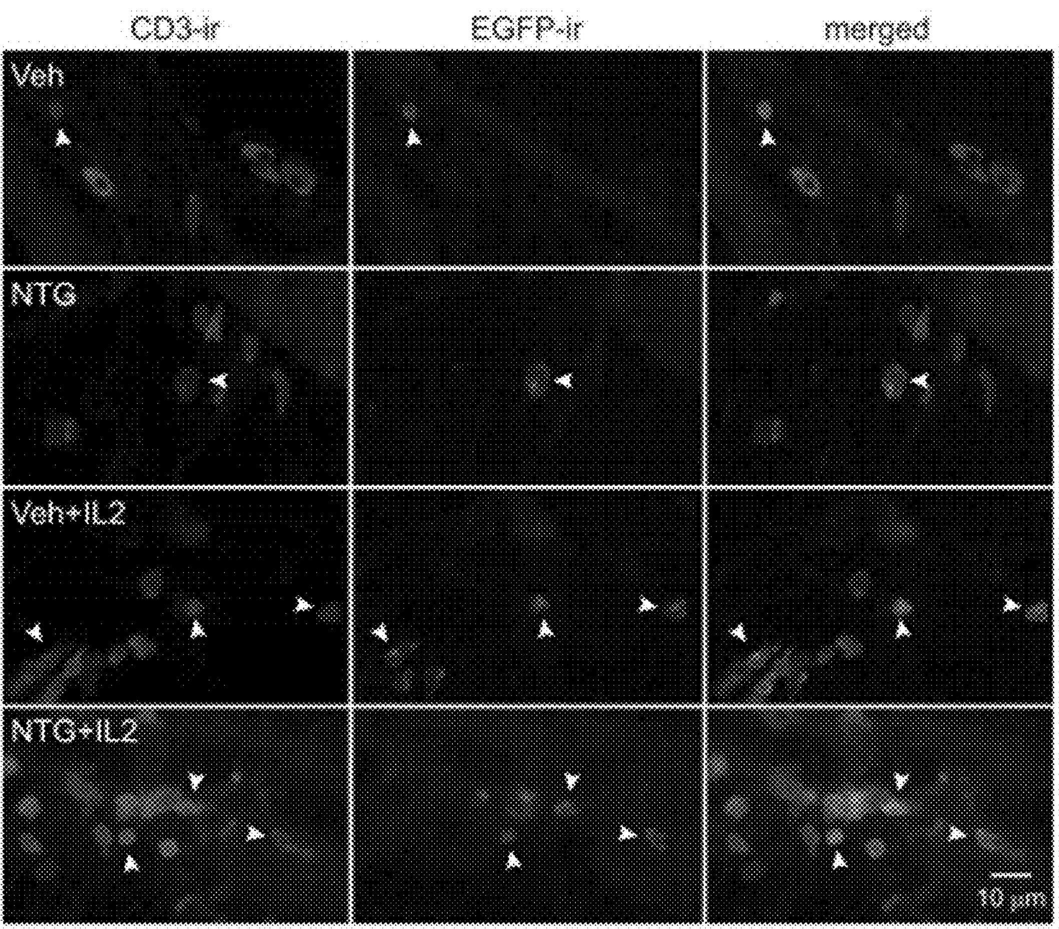
FIG. 5A-5F show ld-IL2 treatment increases the number of Treg cells in dura, TG and DRG.
Figure 5B:
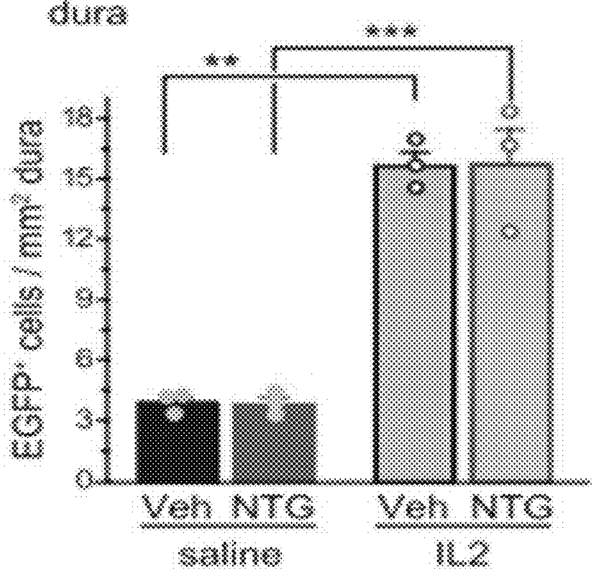
Figure 5C:
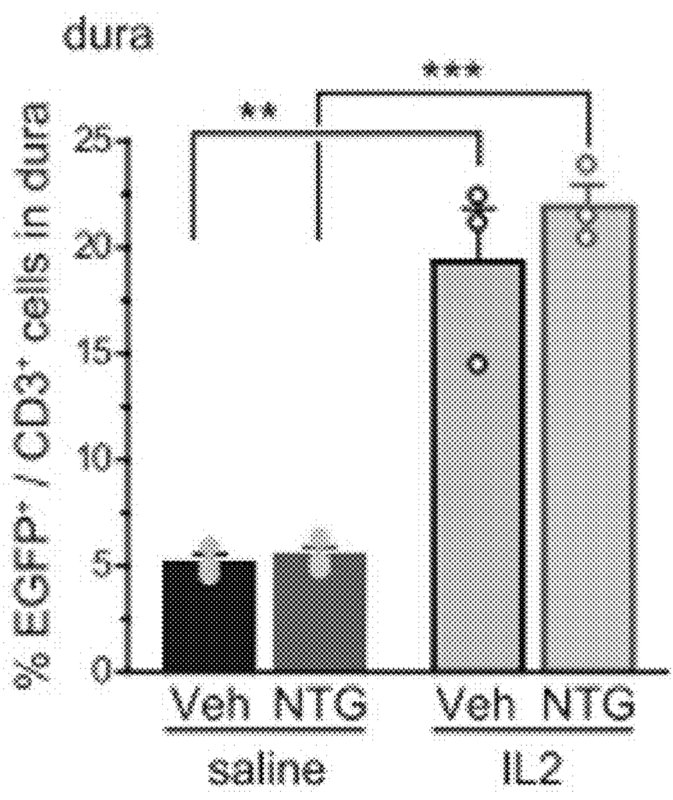
Figure 5D:
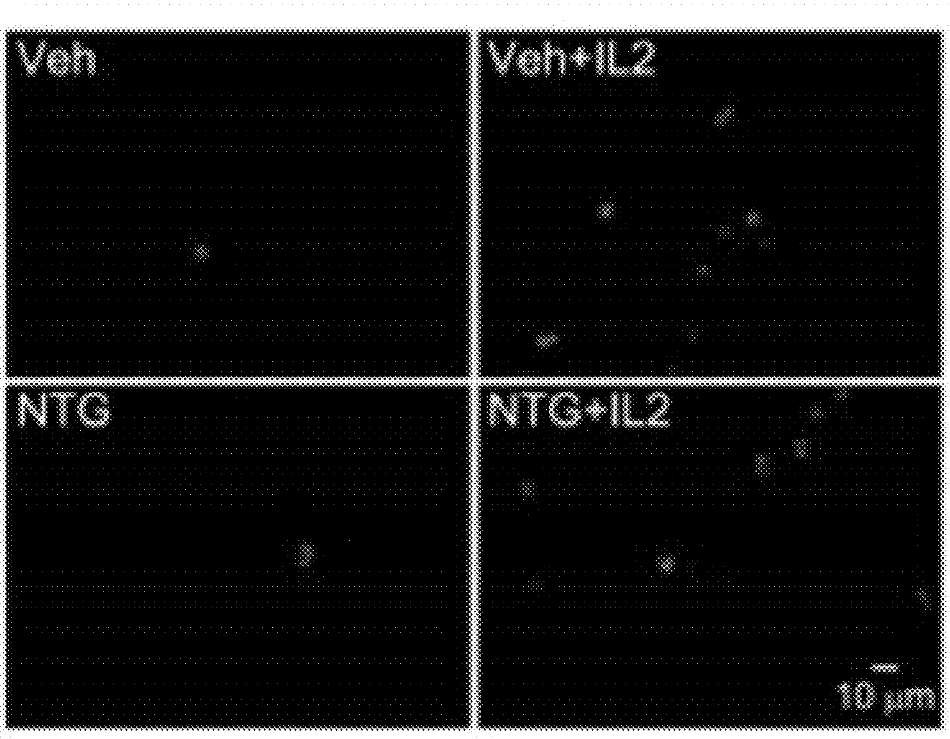
Figures 5E, 5F:
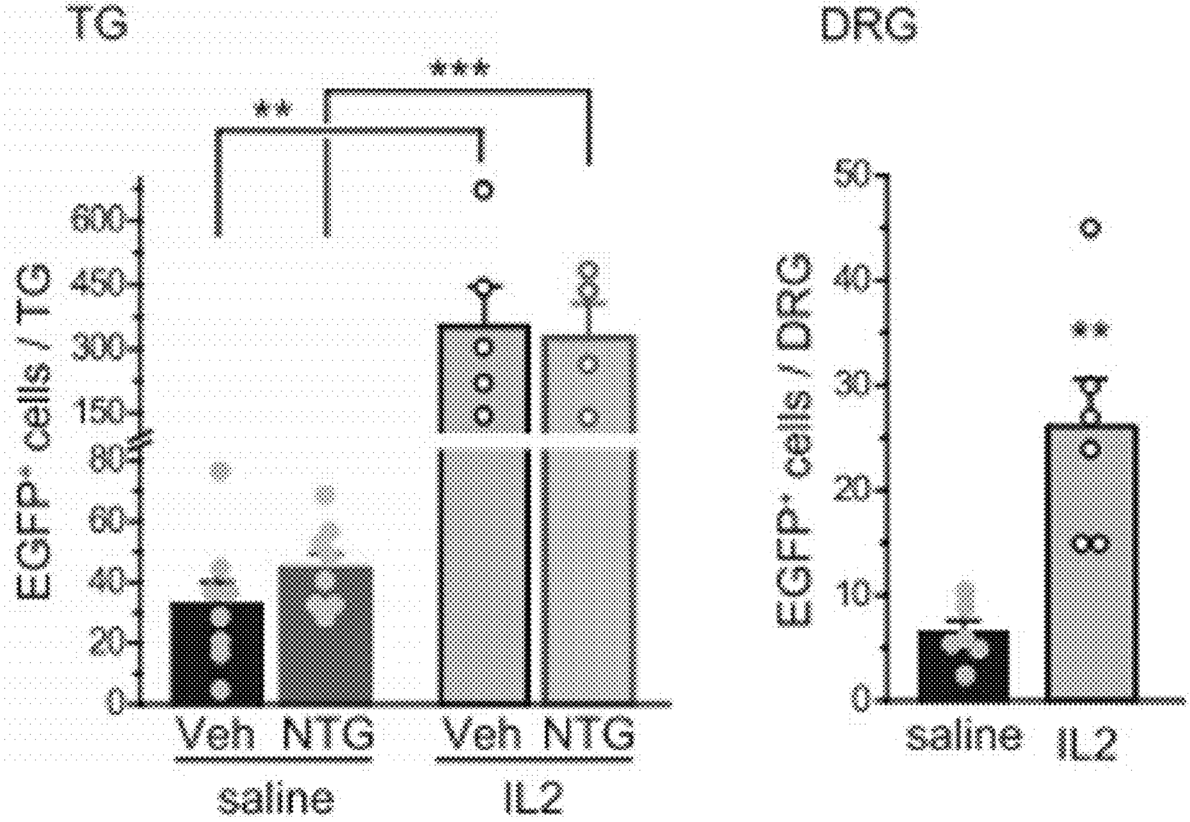

Does ld-IL2 increase the number of Treg cells in dura and TG? After 15 days of ld-IL2 treatment, there was a 4-fold increase in the density of EGFP+ Treg cells in the dura surrounding the MMA in male DEREG mice (FIGS. 5A and 5B), whereas the density of CD3+ T cells was not altered (~80 cells/mm2, similar to those of FIG. 1C). Consequently, ld-IL2 increased the frequency of Treg cells among CD3+ cells from 5% to 20% (FIG. 5C). The number of EGFP+ Treg cells increased 9-fold in the TG after ld-IL2 (FIGS. 5D and 5E), much higher than NTG-induced 2-fold increase in total CD3+ cells (FIG. 1D). Ld-IL2 treatment also resulted in a 4-fold increase in the number of EGFP+ Treg cells in DRG (FIG. 5F). These data suggest that ld-IL2 pretreatment inhibits chronic migraine-related behaviors through increasing the proportion of Treg cells among total T cells in dura, TG, and DRG.

Figure 6A:
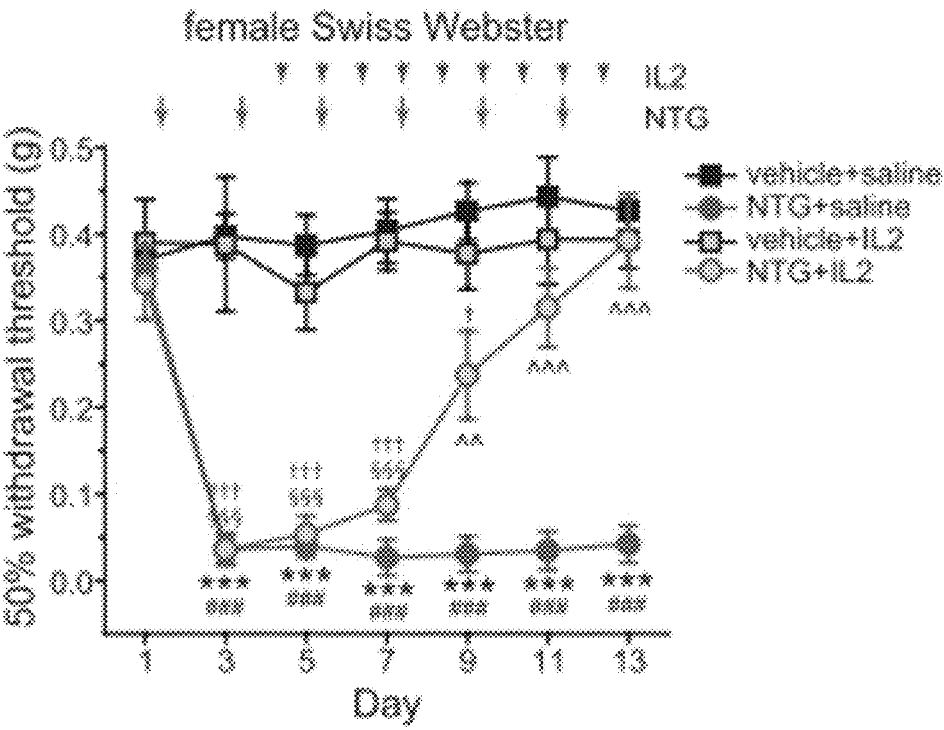

(iii) NTG-Induced Persistent Skin Hypersensitivity is Completely Reversed by Id-IL2 Treatment Next, it was tested whether ld-IL2 can reverse the established facial skin hypersensitivity resulting from repeated exposure to NTG in mice. Previous studies indicate that repeated enhancing of NO signaling results in a persistent facial mechanical hypersensitivity that can be blocked by the migraine preventive drug propranolol. In female Swiss Webster mice, the mechanical threshold at the periorbital region was already substantially reduced 2 days after the first NTG injection (FIG. 6A, NTG+saline group, day 1 vs day 3). The facial mechanical hypersensitivity was sustained during the subsequent NTG injections (FIG. 6A, NTG+saline group, day 3-13). ld-IL2 treatment was started after mice received 2 NTG injections (FIG. 6A). Baseline facial mechanical threshold was not altered by daily ld-IL2 (FIG. 6A, vehicle+saline vs vehicle+IL2). Conversely, NTG-induced mechanical hypersensitivity started to reverse after 5 days of ld-IL2 treatment (FIG. 6A, day 9, NTG+saline vs NTG+IL2). After 7 to 9 days of IL2 injections, the facial mechanical threshold of mice in the NTG+IL2 group was not different from those in the vehicle+saline or vehicle+IL2 groups (FIG. 6A, day 11-13), indicating that ld-IL2 can completely reverse the established persistent facial mechanical hypersensitivity resulting from repeated NTG injections.

Figure 6B:
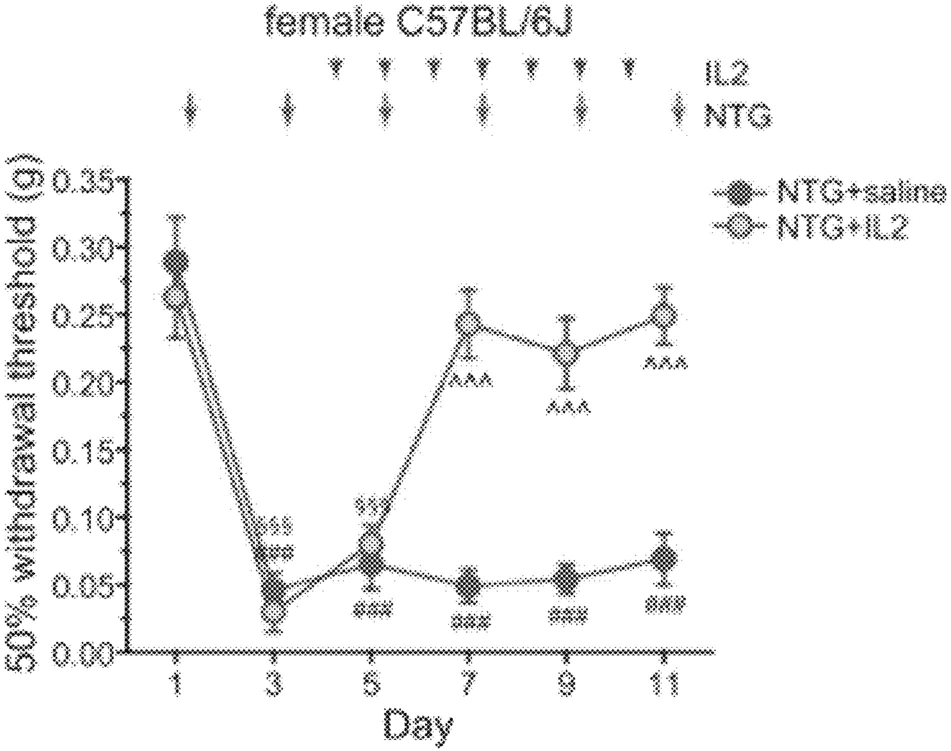

The experiment was repeated in female C57BL/6J mice. The development and maintenance of NTG-induced sensitization was similar to that seen in Swiss Webster females (FIG. 6B, NTG+saline group), and 3 injections of ld-IL2 was sufficient to completely reverse the effect of repeated NTG (FIG. 6B, NTG+IL2 group). Moreover, continuous ld-IL2 treatment prevented subsequent NTG administrations from inducing behavioral sensitization (FIG. 6B, day 7-11). It was also tested whether ld-IL2 blocks NTG-induced acute reduction of facial mechanical threshold, which models the sensory hypersensitivity during a migraine episode in humans. The facial mechanical threshold of naïve C57BL/6J mice was significantly reduced 3 hours after systemic injection of NTG (10 mg/kg, i.p., FIG. 6C day 1). After NTG-induced persistent facial skin hypersensitivity was completely reversed by ld-IL2 (day 11 in FIG. 6B), a subsequent NTG injection did not cause an acute reduction of facial mechanical threshold 3 hours later (FIG. 6C, day 11), suggesting that ld-IL2 prevents the onset of migraine episodes triggered by NO signaling.

Next, it was tested how long the effect of ld-IL2 lasts after the cessation of treatment and how NTG-induced facial hypersensitivity responds to the second round of ld-IL2 treatment. In male C57BL/6J mice, facial mechanical hypersensitivity was sustained by repeated NTG injections for at least 4 weeks (FIG. 6D, NTG 1 saline) and was completely reversed by 7 daily ld-IL2 treatments (FIG. 6D, day 4-10). After cessation of IL2, it took 2 NTG injections (day 11-13) to lower the mechanical threshold to the level comparable to that of the NTG+saline group (FIG. 6D, day 15). A second round of the daily ld-IL2 treatment was then started (FIG. 6D, day 19-22). Notably, fewer ld-IL2 injections (4 vs 7 in the first session) were required to completely reverse NTG-induced mechanical hypersensitivity. The slope of reversal was also compared (change of threshold per day) between day 5 to 11 and day 19 to 23. The slope of ld-IL2-induced reversal was significantly steeper in the second session (10.3±1.3, day 19-23) than the first (5.3±0.9, day 5-11, $P<0.01$, two-tailed t test). Upon cessation of the second ld-IL2 treatment, it took 3 NTG injections (day 23-27) to reduce the withdrawal threshold to the level similar to that of the NTG 1 saline group (FIG. 6B, day 29). Taken together, it was concluded that daily ld-IL2 can completely reverse the established persistent facial skin hypersensitivity resulting from repeated NTG administration, and the effect of IL2 occurs faster and lasts longer in mice with previous ld-IL2 treatment.

(iv) Treg Cells Mediate the Therapeutic Effect of Ld-IL2

Figures 7A, 7B, 7C, 7D:
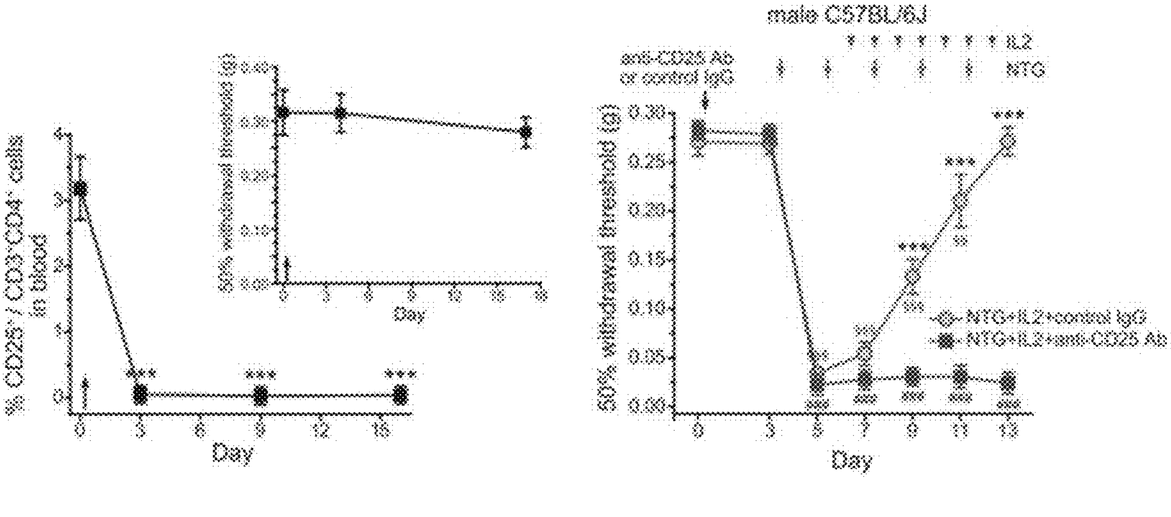

To identify the cellular target of ld-IL2, mice were treated with an antibody against CD25, the IL2 receptor □ chain that is highly expressed in Treg cells. A single injection was sufficient to deplete 99% of Treg cells for 2 weeks without altering the facial mechanical thresholds at basal level or after NTG administration (FIG. 7A). By contrast, the effect of ld-IL2 was completely abolished in Treg-depleted mice (FIG. 7B). NTG-induced facial skin hypersensitivity persisted in CD25 antibody-treated mice throughout the course of ld-IL2 treatment (FIG. 7B, day 7-13), suggesting that endogenous Treg cells mediate the therapeutic effect of ld-IL2.

In addition to Treg cells, CD25 antibody may affect activated T cells in NTG-treated mice. Therefore, it was examined whether adoptive transfer of Treg cells reverses NTG-induced skin hypersensitivity. Naïve C57BL/6J donor mice were treated with ld-IL2 for 12 days, as previous work shows that Treg cells from IL2-treated mice exhibit stronger suppressive activity compared with those from saline-treated mice, it was then enriched CD25+CD4+ Treg cells from IL2-treated mice and adoptively transferred the cells to male C57BL/6J mice that had received 2 NTG injections and exhibited profound facial skin hypersensitivity to mechanical stimuli (FIG. 7C, day 4). The day before Treg transfer, the withdrawal threshold to von Frey filaments was about 14% of the baseline value (FIG. 7C, day 3). One day after the Treg transfer, the threshold was already increased to 70% of the baseline value (FIG. 7C, day 5). The effect of transferred Treg lasted for more than 15 days (FIG. 7C, day 5-21), so that the subsequent 7 NTG injections (day 5-17) completely failed to induce either acute (FIG. 7D) or persistent (FIG. 7C, day 7-19) mechanical hypersensitivity on facial skin. The frequency of CD25+ Treg in the peripheral blood increased to 173±33% of the baseline level on day 6 (n=4 mice, P<0.05, one-sample t test), remained at 146±39% on day 18, and returned to baseline level (109±41%) by day 26. In control mice that received adoptive transfer of CD25+ CD4+ T cells from IL2-treated mice, repeated NTG injections induced persistent facial skin mechanical hypersensitivity throughout the experiment (FIG. 7C). Similar to ld-IL2, Treg transfer did not alter baseline nociceptive responses to heat, cold, or mechanical stimuli on facial skin or on hindpaw (FIGS. 7E-7I). This is consistent with the working model that ld-IL2 reverses the effects of repeated NTG administration through targeting endogenous Treg cells.

To verify the purity of the transferred Treg cells, flow cytometry analysis was conducted on the enriched CD25+ CD4+ Treg cells from DEREG mouse splenocytes. The preparations consisted of 92±4% live cells, 97±1% CD4+ cells among live cells, 87±0.4% CD25+ cells among CD4+ cells and 90±1% EGFP+ cells among CD25+CD4+ cells (n=3 preparations, 2 mice per preparation), validating that the transferred cells were enriched in Treg. Treg cells from IL2-treated DEREG mice were also adoptively transferred to C57BL/6J recipient mice and used the EGFP signal to determine the tissue distribution of transferred Treg cells. EGFP+ cells were present in the dura and TG 1 day after the adoptive transfer, and the level remained stable for at least 5 days (FIG. 8). By contrast, the cervical/medullary dorsal horn TCC of recipient mice contained few, if any, EGFP+ cells (0-2 cells/mouse) during this period, indicating that the transferred Tregs are located outside the brain while exerting their antimigraine effects.

Figure 9A:
FIG. 9A-9G show ld-IL2 treatment reverses the facial skin hypersensitivity in a mouse model of mTBI-induced acute and persistent PTH.

(v) Ld-IL2 Treatment Inhibits Mild Traumatic Brain Injury (mTBI)-Induced Facial Mechanical Hypersensitivity and Hyperalgesia Priming Post-traumatic headache is a debilitating secondary headache disorder and is the most common medical consequence of mTBI (Yilmaz T, et al., Emerg Med J 2017; 34:800-5. Acute PTH occurs within 7 days of the injury. Persistent PTH lasts longer than 3 months to years after the trauma and often takes on a pattern of daily occurrence in the most severe cases. It was asked whether ld-IL2 can prevent and/or reverse PTH-related behaviors in a mouse model (FIG. 9A). In both male and female Swiss Webster mice, mTBI resulted in a significant reduction of the facial mechanical threshold (FIG. 9B, mTBI+saline groups, 3-28 days), which is mechanistically related to acute PTH. There was no motor deficit as measured by rotarod, open-field, and adhesive removal tests between 6 and 12 days after mTBI, when facial mechanical hypersensitivity reached the plateau (FIG. 10). After the mechanical thresholds returned to basal level 35 days after mTBI, mice were treated with low-dose NTG (0.1 mg/kg, i.p.) daily for 4 to 6 days to mimic high frequency persistent PTH and measured the facial mechanical thresholds 1 day after the last NTG treatment. Only mice that experienced mTBI developed facial mechanical hypersensitivity to repeated low-dose NTG (FIG. 9C, mTBI+saline groups), which is mechanistically related to mTBI-induced hyperalgesia priming during persistent PTH.

Figure 9B:
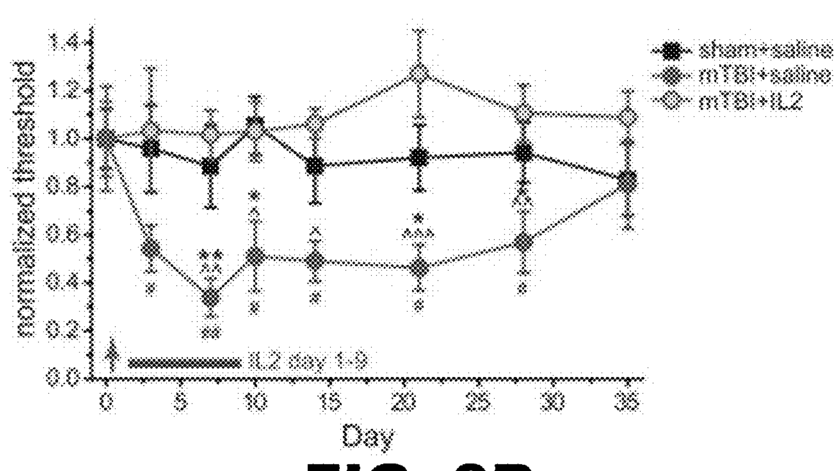
Figure 9C:
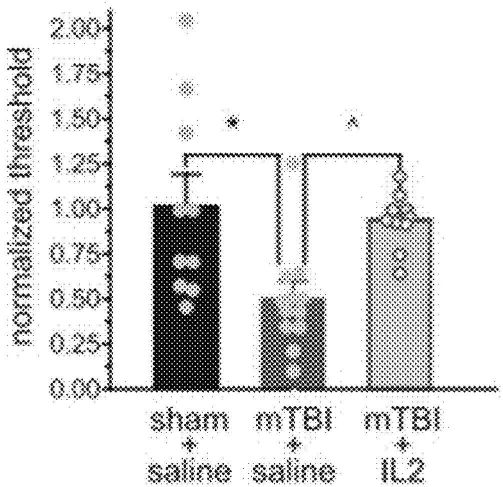
Figure 9D:
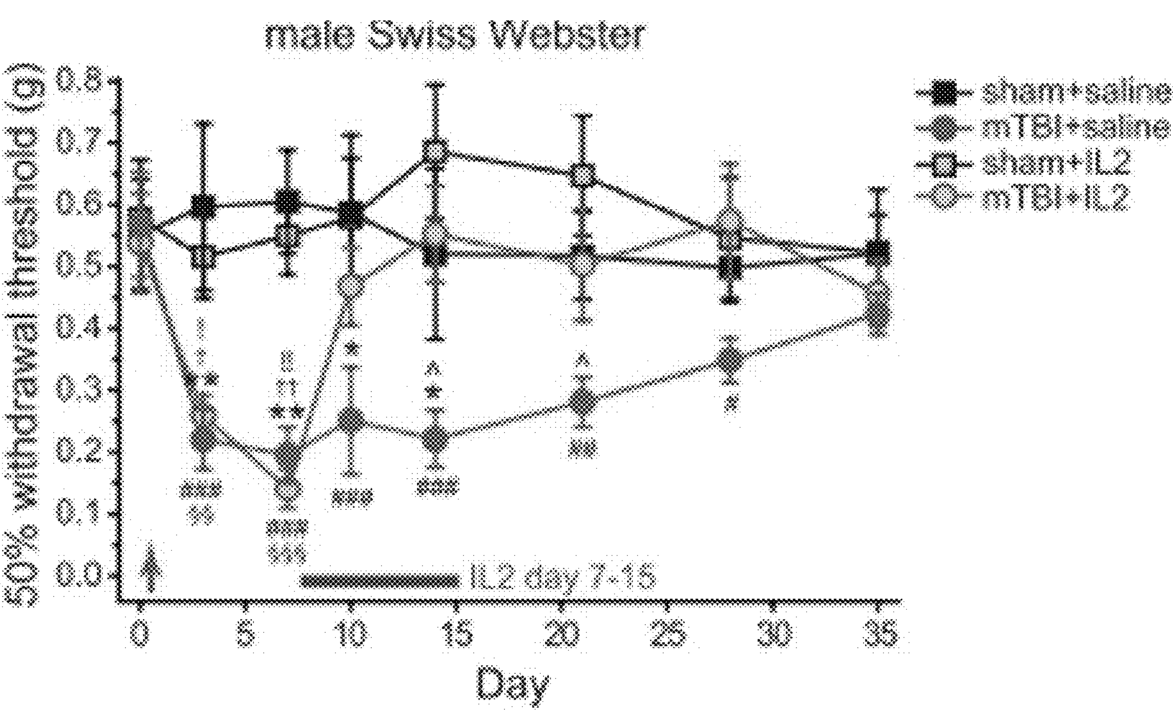
Figure 9E:
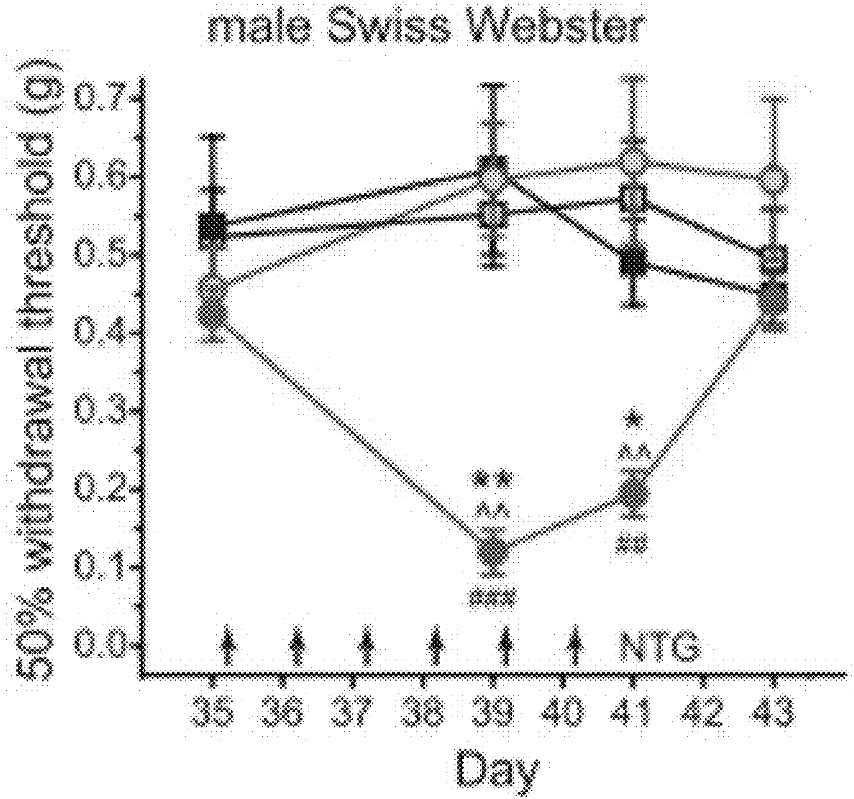
Figures 9F, 9G:
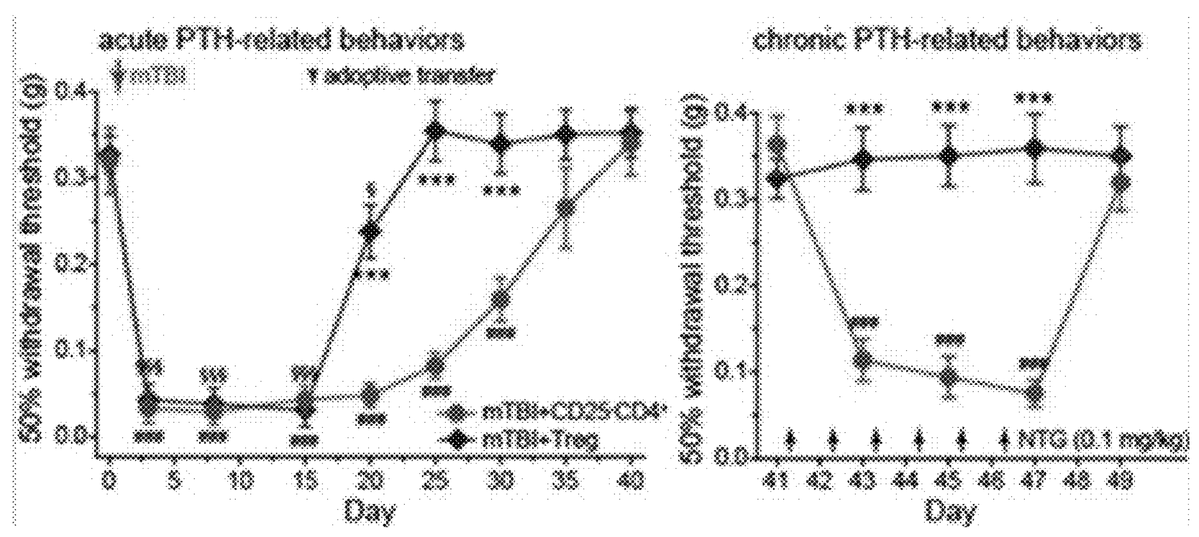
Figures 10A, 10B, 10C, 10D, 10E, 10F, 10G:
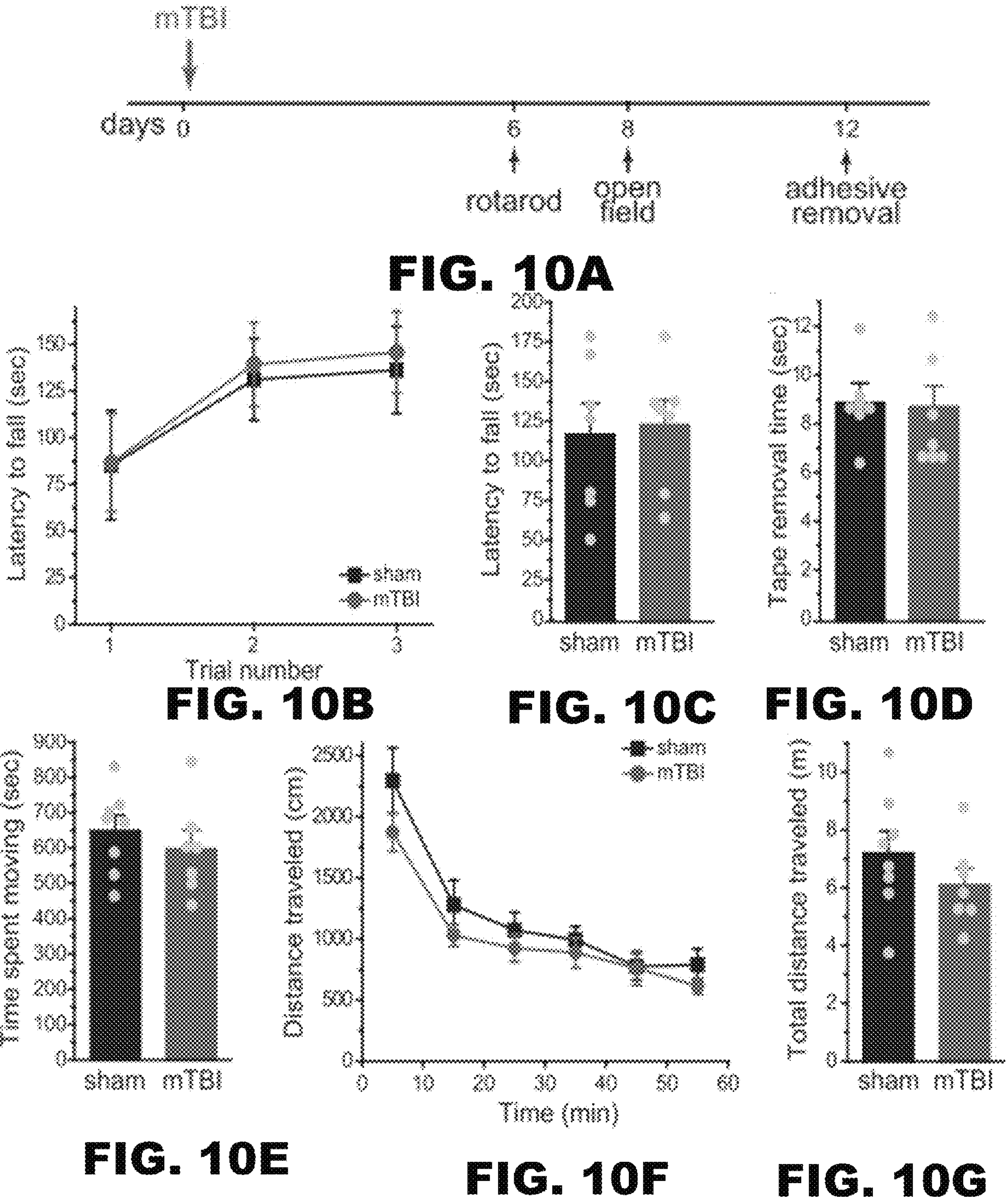
FIG. 10A-10K show mild traumatic brain injury does not cause motor impairment.
Figure 10H:
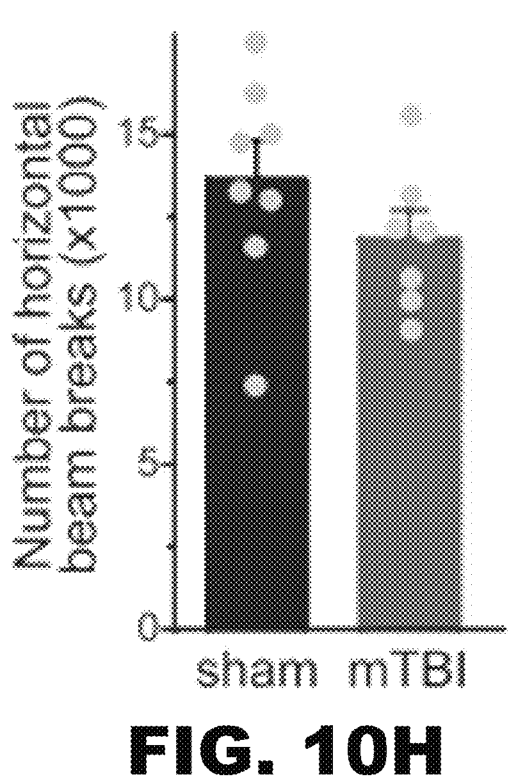
Figure 10I:
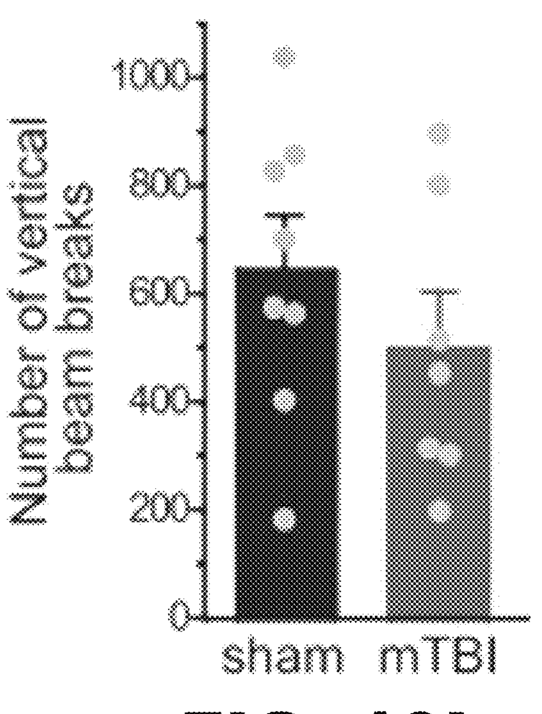
Figure 10J:
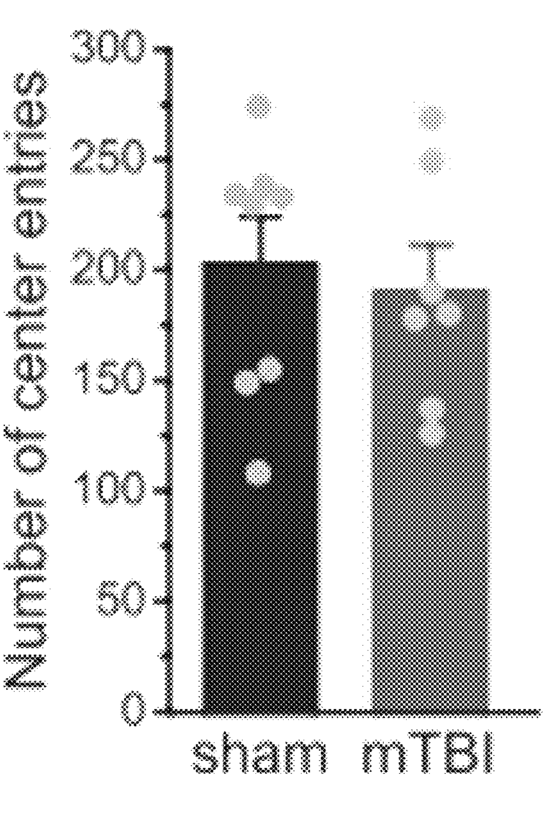
Figure 10K:
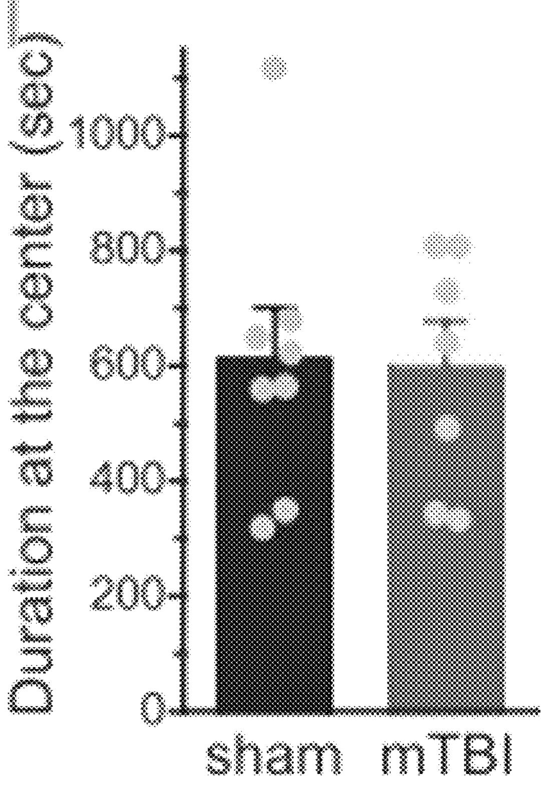
Figure 11A:
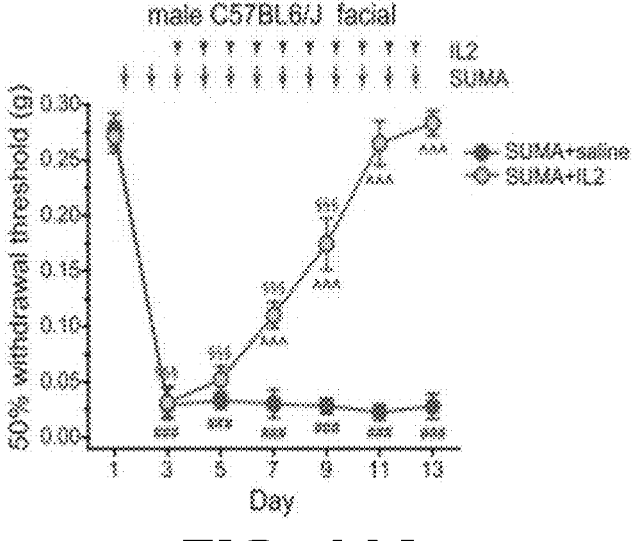
FIG. 11A-11D show ld-IL2 treatment reverses the skin hypersensitivity in a mouse model of MOH.
Figure 11B:
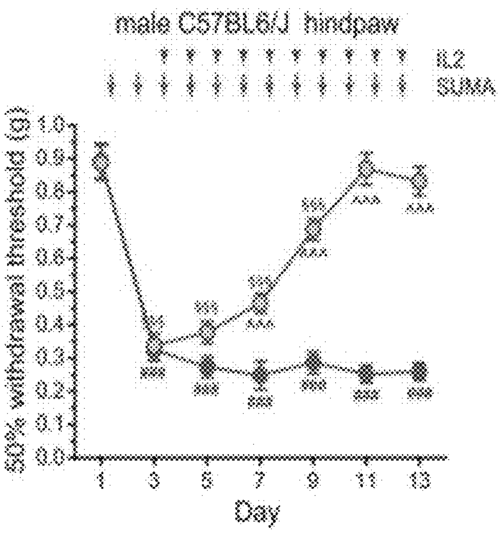
Figure 11C:
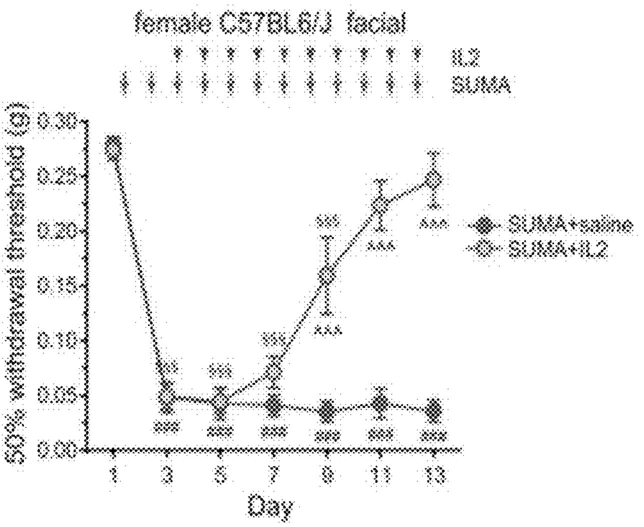
Figure 11D:
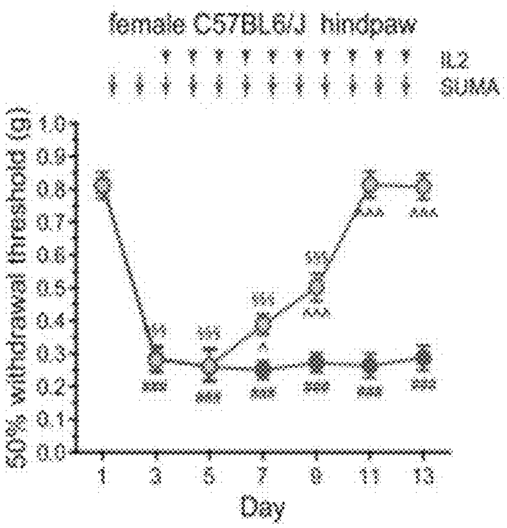

First, female Swiss Webster mice were treated with daily ld-IL2, starting 1 day after mTBI for 9 days (FIG. 4A). This completely prevented the development of mTBI-induced acute facial mechanical hypersensitivity as well as the hyperalgesia priming revealed by repeated low-dose NTG (FIGS. 9B and 9C, mTBI 1 IL2 groups). Next, male Swiss Webster mice were treated with daily ld-IL2 for 9 days, starting on post-mTBI day 7, when the facial mechanical threshold decreased to about 26% of the baseline value (FIG. 9D). The threshold returned to 87% of the baseline value after 3 days of ld-IL2 (FIG. 9D, day 10, mTBI+IL2 group), and mTBI-induced facial skin hypersensitivity was fully reversed by the end of ld-IL2 treatment (FIG. 9D, day 15). Daily ld-IL2 did not change the facial mechanical sensitivity of sham mice (FIG. 9D, sham+saline vs sham+IL2 groups). Importantly, 3 weeks after the cessation of Id-IL2, repeated low-dose NTG failed to establish persistent facial mechanical hypersensitivity in mice that experienced mTBI (FIG. 9E, mTBI+saline vs mTBI+IL2 groups). Collectively, these results indicate that ld-IL2 treatment after mTBI not only reverses injury-induced facial skin hypersensitivity but also prevents the development of hyperalgesia priming related to persistent PTH. FIGS. 9F and 9G show that adoptive transfer of Treg cells 2 weeks after mild traumatic brain injury (mTBI) not only accelerated the resolution of acute PTH-related behaviors but also completely prevented the development of chronic-PTH related behavior. Collectively, these data support Treg as a cellular target for treating both acute and chronic PTH.

Figure 12:
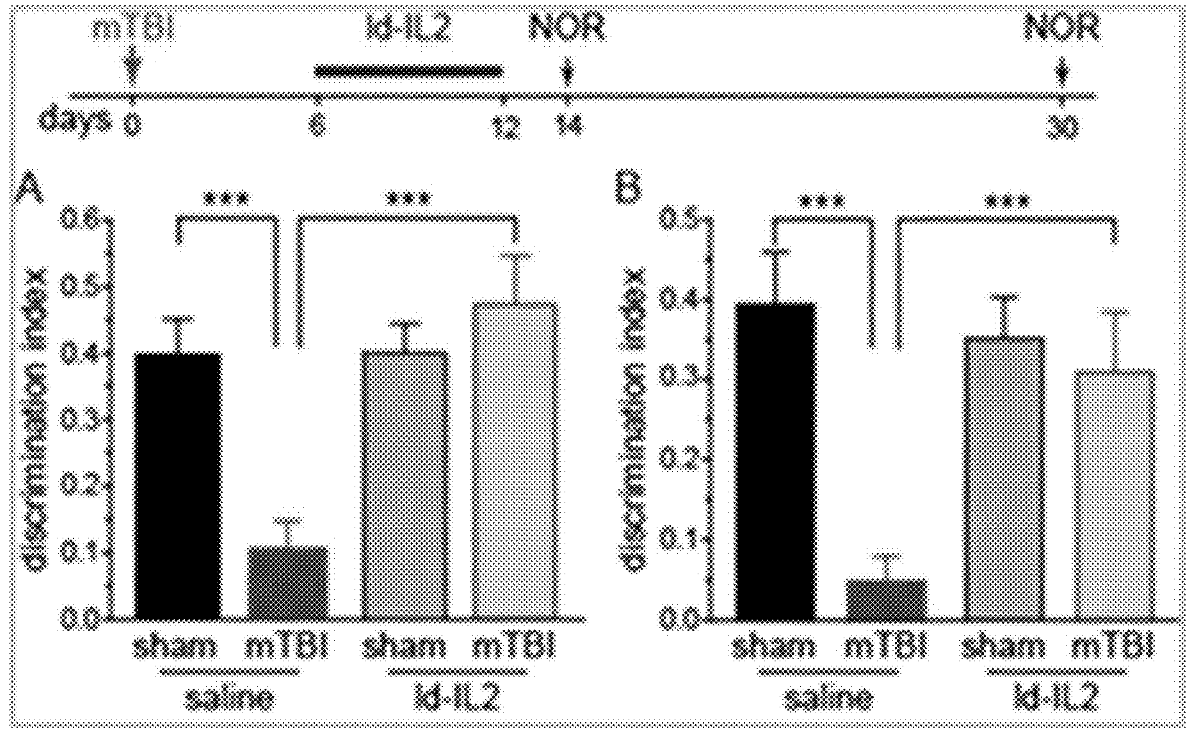
FIG. 12 shows ld-IL2 treatment prevents mTBI-induced memory deficit. Mice received ld-IL2 between day 6 and 12 after sham or mTBI. NOR assay was conducted on day 14 and 30 post-mTBI (n=7 CD1 males/group). ***p<0.001, two-way ANOVA with post hoc Bonferroni test.

A large proportion of individuals with mTBI continue to demonstrate measurable cognitive impairment long after the initial injury. The novel object recognition (NOR) assay was used to test the effect of mTBI and ld-IL2 treatment on cognition. On the training day, mice were allowed to explore two identical objects in an arena for 10 minutes. The next day, mice were allowed to explore the same space in the presence of the familiar object and a novel object to test long-term recognition memory. The control mice spent longer time exploring the novel object than the familiar one, hence having a high discrimination index (FIG. 12, sham+saline). After mTBI, mice spent similar amounts of time exploring the familiar and the novel object, indicating a deficit in recognition memory (FIG. 12, mTBI+saline). Mice that received ld-IL2 between day 6 and 12 post-mTBI did not exhibit NOR deficit (FIG. 12, mTBI+IL2). Remarkably, the effect of ld-IL2 on memory deficit lasted for at least 20 days after the cessation of treatment.

(vi) Ld-IL2 Treatment Reverses Cutaneous Mechanical Hypersensitivity in a Mouse Model of Medication Overuse Headache Medication overuse headache is the most common secondary headache disorder, resulting from chronic and excessive use of medication to treat headache, for example, sumatriptan. In both male and female C57BL/6J mice, daily administration of sumatriptan (0.6 mg/kg, i.p.) resulted in persistent facial and hindpaw mechanical hypersensitivity (FIGS. 11A-11D, SUMA+saline groups), consistent with previous reports. Ld-IL2 treatment was initiated after mice received 2 sumatriptan injections, after the establishment of mechanical hypersensitivity (FIGS. 11A-11D, day 3). In both male and female mice, sumatriptan induced cutaneous hypersensitivity was significantly attenuated after 4 to 6 ld-IL2 injections (FIG. 11, day 7-9) and was completely reversed after 8 days of IL2 treatment (FIG. 11, day 11). Moreover, with the continuous ld-IL2 treatment, neither male nor female mice developed cutaneous hypersensitivity in response to subsequent sumatriptan injections (FIG. 11, day 13). Therefore, it was concluded that ld-IL2 treatment not only reverses sumatriptan induced behavioral sensitization but also prevents the recurrence of sensitization by subsequent sumatriptan administrations.

Discussion

Recent years have seen significant advances in elucidating the mechanisms and in developing new therapy for chronic migraine and other headache disorders. Despite these exciting progresses, many patients remain either unresponsive to available treatments or intolerant to their side effects. Although numerous studies indicate that the activation of many proinflammatory immune cells contributes to the pathophysiology of migraine and PTH, the involvement of the immunosuppressive Treg cell in the chronification of headache disorders remains unknown. Many preclinical studies have identified ld-IL2 as a safe and effective treatment for multiple autoimmune and neurodegenerative diseases, but the potential of ld-IL2 as a therapy for headache disorders has not been explored. In this Example, multiple preclinical models and behavioral endpoints in male and female, inbred and outbred strains of mice were used to address these knowledge gaps. For the first time it was reported that repeated NTG administration significantly reduced the ratio of Treg cells among total T cells in TG, suggesting that chronic migraine is associated with a deficiency in Treg-mediated immune homeostasis in TG. Next, the therapeutic use of ld-IL2 in mouse models of chronic migraine, PTH, and MOH was tested. Remarkably, in all these models, ld-IL2 treatment completely reversed the established facial skin hypersensitivity, which reflects the central sensitization under the chronic disease states. Continuous ld-IL2 treatment prevented the development of NTG- and sumatriptan-induced mechanical hypersensitivity related to chronic migraine and MOH, respectively. For behaviors related to mTBI-induced acute and persistent PTH, the therapeutic effect of ld-IL2 persisted after cessation of the treatment. The clinical significance of these findings is that it provides the first proof-of-concept that ld-IL2 may constitute an innovative therapeutic strategy for the prevention and reversal of chronic migraine, PTH, and MOH.

NTG administration is a well-established experimental model of migraine. In migraineurs, NTG triggers migraine-like headache as well as cutaneous allodynia, and both are responsive to triptan treatment. In rodents, both NTG-induced acute cutaneous allodynia and central sensitization can be blocked by sumatriptan and antagonists to calcitonin gene-related peptide (CGRP) receptor, suggesting that NTG-induced changes in rodents reflect the spontaneous migraine with cutaneous allodynia in some patients. Repeated administration of NTG and other NO donors in rodents elicits persistent cutaneous allodynia that can be blocked by migraine prophylactics topiramate and propranolol, validating that these behavioral changes model symptoms of chronic migraine in humans. In this Example, it was found that repeated NTG administration resulted in facial cold and mechanical hypersensitivity as well as hindpaw mechanical hypersensitivity, all of which were prevented by pretreatment with ld-IL2. Starting ld-IL2 treatment after mice received repeated NTG administration completely reversed the established persistent facial mechanical hypersensitivity, regardless of mouse strain and sex. Continuous ld-IL2 treatment prevented subsequent NTG injections from re-establishing either acute or persistent cutaneous hypersensitivity. Collectively, these data predict that ld-IL2 treatment not only blocks trigger-induced migraine episodes, thereby preventing migraine chronification, but also induces the remission of chronic migraine in both males and females. Notably, a recent study reports that neither sumatriptan nor CGRP receptor antagonist olcegepant prevents the persistent cephalic mechanical hypersensitivity induced by repeated administration of NO donor isosorbide dinitrate (Dallel R, et al., Cephalalgia 2018:38:776-85), raising the possibility that ld-IL2 may be effective in reversing chronic migraine that is not responsive to drugs targeting CGRP signaling.

We did not attempt to determine the therapeutic window of ldIL2 in mice because the dose of IL2 required to activate/expand mouse and human Treg cells is very different, and numerous clinical trials have already established the appropriate dose of ld-IL2 in humans. The daily dose of IL2 used in this Example was observed to preferentially increased the frequency of Treg cells in the blood, LNs, and spleen without altering the frequencies of CD4+ and CD3+ T cells. Moreover, ld-IL2 treatment increased the number of Treg cells in dura and TG by 4 to 9 folds, much higher than that seen in the blood, LNs, or spleen. Results from Treg depletion and adoptive transfer experiments further validated Treg cell as the cellular target of ld-IL2. Depletion of endogenous Treg cells with anti-CD25 antibody did not alter the magnitude of NTG-induced mechanical hypersensitivity, likely due to the high dose of NTG used in our study. Whether Treg depletion alters the time course of NTG-induced behaviors and/or enhances the effects of lower dose of NTG merits further investigation.

In this Example, adoptive transfer of Treg cells from IL2-treated mice was performed. Notably, many exogenous Treg cells were present in the dura and TG 1 day after the adoptive transfer, whereas few Treg cells could be detected in the cervical/medullary dorsal horn even 5 days after the transfer. Together, these results implicate dura and/or TG as sites of action for the therapeutic effect of ld-IL2 and Treg transfer, despite the fact that systemic NTG administration activates multiple pathways at both central and peripheral levels. This is consistent with the recent studies indicating that both antiCGRP antibodies and botulinum toxins act peripherally to reduce the frequency of migraine attacks.

In rodent models of nerve injury and experimental autoimmune encephalomyelitis, mechanical allodynia was exacerbated by the depletion of Treg cells and was attenuated by the increase in Treg cell number. This Example expanded the therapeutic value of ld-IL2 and Treg cells to chronic migraine and other headache disorders. Importantly, neither daily ld-IL2 treatment nor Treg transfer alters basal nociceptive responses, and the second round of ld-IL2 treatment reversed NTG-induced hypersensitivity faster and the effect lasted longer than the first round treatment. These data suggest that there is minimum risk of developing drug tolerance and/or MOH associated with ld-IL2 treatment. In fact, ld-IL2 completely reversed the facial as well as hindpaw hypersensitivity induced by daily injections of sumatriptan in both male and female mice. It is possible that ld-IL2 can reverse MOH resulting from repeated use of sumatriptan as well as other antimigraine drugs, as a recent study shows that chronic exposure of rats to 2 acute headache medications with completely different mechanisms of action induced highly similar transcriptome changes in TG.

In rodent models of mTBI-induced PTH, the development of both acute and persistent PTH-related behaviors can be prevented by the repeated administration of anti-CGRP antibodies, starting immediately or 2 hours after mTBI. Discontinuing the anti-CGRP treatment after the resolution of mTBI induced acute allodynia partially inhibits the development of hyperalgesia priming and administration of anti-CGRP antibody after the resolution of acute allodynia fails to block the development of cutaneous allodynia in response to bright light stress. In our model of mTBI-induced PTH, starting ld-IL2 treatment 1 day after mTBI completely prevented the development of mTBI-induced acute facial mechanical hypersensitivity as well as the hyperalgesia priming revealed by repeated low-dose NTG. Notably, starting the 9-day ld-IL2 treatment after the acute hypersensitivity was fully established (7 days after mTBI) could still completely prevent the development of hyperalgesia priming in addition to facilitating the resolution of acute mechanical hypersensitivity. In both cases, 9 days of ld-IL2 treatment was sufficient to protect both male and female mice from developing mTBI-induced hyperalgesia priming for at least 30 days. These results illustrate the potential of ld-IL2 as a novel therapy for mTBI induced acute and persistent PTH, with a wide therapeutic time window and long-lasting beneficial effect after the cessation of the treatment. In addition to peripheral CGRP signaling, meningeal mast cell is also involved in the development of mTBI-induced hyperalgesia priming.

There is abundant evidence from many clinical trials that both ld-IL2 treatment and Treg cell transfer are well tolerated in patients and show indications of efficacy against multiple autoimmune diseases. The promising results for this Example strongly support further clinical assessment of ld-IL2 treatment for multiple headache disorders including chronic migraine, PTH, and MOH.

Example 2: Low-Dose Interleukin-2 Attenuates Nerve Injury-Induced Punctate and Dynamic Allodynia in a Mouse Model Nerve injury-induced mechanical hyper-sensitivity, in particular stroking-induced dynamic allodynia, is highly debilitating and difficult to treat. Previous studies indicate that the immunosuppressive regulatory T (Treg) cells modulate the magnitude and the resolution of mechanical allodynia evoked by punctate stimuli (von Frey filaments) in mouse models of sciatic nerve injury. However, whether enhancing Treg number and/or function attenuates dynamic allodynia is not known. Many preclinical and clinical studies have identified low-dose interleukin-2 (ld-IL2) as a safe and effective treatment for multiple autoimmune and neurodegenerative diseases through enhancing Treg-mediated immunosuppression, but whether ld-IL2 ameliorates nerve injury-induced mechanical allodynia has not been investigated. In the present Example, these questions were addressed by using ld-IL2 to expand and activate endogenous Treg cells in a mouse model of spared nerve injury (SNI). This not only attenuated SNI-induced punctate allodynia, but also reversed the dynamic allodynia without affecting basal responses to punctate or brush stimuli. The therapeutic effect of ld-IL2 was recapitulated by the adoptive transfer of Treg cells, independent of mouse sex and/or strain. Collectively, the present Example identifies Treg cell as a promising target for treating both nerve injury-induced punctate and dynamic allodynia. These results support the potential of ld-IL2 as a treatment for both punctate and dynamic mechanical allodynia in the setting of nerve injury.

About 7-10% of the general population suffer from neuropathic pain that results from damage to the somatosensory nervous system. Mechanical hyper-sensitivity, especially the dynamic allodynia evoked by stroking stimuli (brush or gentle touch), is one of the most debilitating and prevalent symptoms of neuropathic pain, and is often resistant to current treatments. In animal models of neuropathic pain, morphine attenuates punctate allodynia evoked by von Frey filaments at early (<2 weeks post-injury) but not late stage; whereas the dynamic allodynia is resistant to morphine treatment at all stages. Likewise, current pharmacotherapy only achieve less than 50% reduction of pain severity in about 30% neuropathic pain patients.

Regulatory T (Treg) cells are a specialized subpopulation of CD4+ T cells that express high-level of transcription factor Foxp3 and the high-affinity interleukin-2 (IL2) receptor CD25. They employ multiple mechanisms to suppress the activation and proliferation of all other immune cells to maintain immune homeostasis [8]. In mouse models of sciatic nerve injury, the number of Treg cells is reduced in the spleen but is increased in the injured nerves, the ipsilateral draining lymph nodes, dorsal root ganglia (DRG), and the dorsal horn of the spinal cord. Nerve injury-induced cutaneous punctate mechanical allodynia is exacerbated by the depletion of endogenous Treg cells, and is attenuated by the increase in Treg cell number. However, whether enhancing Treg number and/or function ameliorates the morphine-resistant dynamic allodynia has not been tested.

Results from many preclinical and clinical studies have supported low-dose interleukin-2 (ld-IL2) treatment as a safe and effective treatment for multiple autoimmune and neurodegenerative diseases through enhancing Treg-mediated immunosuppression. In Example 1, it was shown that ld-IL2 effectively reverses behavioral sensitization in several mouse models of chronic headache disorders without altering basal nociceptive responses or inducing tolerance. Here, it was investigated whether ld-IL2 treatment is effective for peripheral nerve injury-induced punctate and dynamic allodynia. In the mouse model of spared nerve injury (SNI), ld-IL2 treatment attenuated SNI-induced punctate allodynia as well as the dynamic allodynia without affecting basal responses to punctate or brush stimuli. The effects of ld-IL2 were recapitulated by the adoptive transfer of Treg cells, independent of mouse sex and/or strain. Collectively, the present study supports Treg cell as a promising target for treating both nerve injury-induced punctate and dynamic allodynia and ld-IL2 as a potential treatment option.

Methods

Mice. All procedures were carried out in strict accordance with the recommendations in the Guide for the Care and Use of Laboratory Animals of the National Institutes of Health and were approved by the Institutional Animal Care and Use Committee at Washington University in St. Louis. All efforts were made to minimize the number of mice used and their suffering. To avoid social isolation stress, all mice were group housed (2-5 per cage, same sex) in the animal facility of Washington University in St. Louis on a 12-hour light-dark cycle with constant temperature (23-24° C.), humidity (45-50%), and food and water ad libitum. All experiments were performed during the light phase (9 am to 4 pm). Female Swiss Webster mice (Charles River, O'Fallon, MO) and male C57BL/6J mice (Jackson Laboratory, 8-14 weeks old) were used in the behavioral experiments.

Mouse model of SNI. Mice were anesthetized with 3-4% isoflurane in an induction chamber until losing the righting reflex. Anesthesia was maintained by 1.5-2% isoflurane through a nose cone. After skin and muscle incision to expose the right sciatic nerve in the thigh region, we tightly ligated two branches (sural and common peroneal nerves) with 7-0 silk suture (Braintree Scientific, Braintree, MA) and transected ~2 mm of the nerve distal to the ligature [1]. The third branch of the sciatic nerve (tibial nerve) was left intact, and caution was taken not to stretch or contact the spared nerve. In sham mice the right sciatic nerve and its branches were exposed but were not touched. After the surgery, the overlying muscle and skin layers were closed separately with 6-0 vicryl suture and interrupted nylon suture for the skin incision, respectively.

Behavioral tests. Mice were extensively handled by the experimenters for 2 weeks and were well-habituated to the test room and the test apparatus before each experiment. The experimenters were blinded to the treatments mice received during data collection and analysis.

Response to punctate mechanical stimuli on the hindpaw. Mice were habituated in individual clear plexiglass boxes (11×11×15 cm) for 1-2 hours. A series of calibrated von Frey filaments were used to apply mechanical stimuli to the medial plantar surface of the hindpaw (the tibial nerve territory). We used the up-down paradigm to determine the 50% withdrawal threshold.

Response to dynamic mechanical stimuli on the hindpaw. Mice were habituated in individual clear plexiglass boxes (11×11×15 cm) for 1-2 hours. The medial plantar surface of the hindpaw (tibial nerve territory) was stimulated by light stroking with a blunt paintbrush (5/0, Princeton Art & Brush Co., Princeton, NJ) from heel to toe at ~2 cm/second. The behavior was scored as described previously. Score 0 indicates no evoked movement or lifting the stimulated paw for less than 1 second. Score 1 indicates a sustained lifting (more than 2 seconds) of the stimulated paw toward the body or a single gentle flinching of the stimulated paw. Score 2 indicates a strong lateral lift of the stimulated paw above the level of the body or a startle-like jump. Score 3 indicates multiple flinching or licking of the stimulated paw. Each paw was tested 3 times, with minimal interval of 3 minutes. The scores of 3 tests were averaged to indicate the response to dynamic mechanical stimuli.

Ld-IL2 treatment. Recombinant mouse IL2 (carrier-free, Biolegend, San Diego, CA) was freshly diluted from the stock (0.5-1 mg/ml aliquots at −80° C.) every day. Each mouse received daily intraperitoneal (i.p.) injection of 1 μg IL2 in 100 μl saline at various durations. The control mice received daily i.p. injections of 100 μl saline. Note that on the days that the mouse behaviors were tested, IL2 was always injected after completing the behavioral tests.

Isolation and adoptive transfer of Treg cells and CD25□CD4+ T cells. Adult C57BL/6J mice (8-12 weeks old) received daily injections of IL2 for 12 days. CD25+ CD4+ Treg cells and CD25□CD4+ cells were isolated from splenocytes through CD4+ T cell negative selection followed by a CD25+ T cell positive selection using EasySep mouse CD4+ T cell pre-enrichment and CD25 positive selection kits (18783, Stem Cell Technologies, Cambridge, MA). Male C57BL/6J mice (8-14 weeks old) received 1×106 Treg or CD25□CD4+ cells via the tail vein 23 days post-SNI surgery.

Statistical analysis. For behavioral experiments, power analysis was conducted to estimate sample size with >80% power to show an effect size of 0.8, alpha (two-sided) of 0.05, and a simple covariance structure for repeated measures.

All data were reported as mean±standard error of the mean. The Shapiro-Wilk test was used to check data normality. Statistical significance between or within experimental groups was assessed by two-tailed t-test, ANOVA (analysis of variance, one-way or two-way, with or without repeated-measures [RM]) with multiple comparisons (Student-Newman-Keuls method, post hoc Dunnett's test or t-test with Bonferroni correction) where appropriate, using Origin (OriginLab, Northampton, MA) and Statistica (StatSoft, Tulsa, OK) softwares. Differences with $p<0.05$ were considered statistically significant. The statistical analysis for individual experiments was described in figure legends.

Results (i) Ld-IL2 Pretreatment Attenuates SNI-Induced Punctate Allodynia and Prevents the Development of SNI-Induced Dynamic Allodynia.

To model neuropathic pain, we ligated and transected two branches of the right sciatic nerve (sural and common peroneal nerves) in female Swiss Webster mice and measured the responses to punctate (von Frey filaments) and dynamic (paintbrush) mechanical stimuli on the medial plantar surface of the right hindpaw, the territory of the spared tibial nerve. SNI resulted in a significant decrease in mechanical threshold to punctate stimuli between 2 and 22 days post-SNI (FIG. 13A, SNI+saline group), consistent with the previous studies. The right paws also exhibited dynamic allodynia to brush stimuli that lasted at least till 31 days post-SNI (FIG. 13B, SNI+saline group), in line with the previous reports.

Figures 13A, 13B, 13C, 13D:
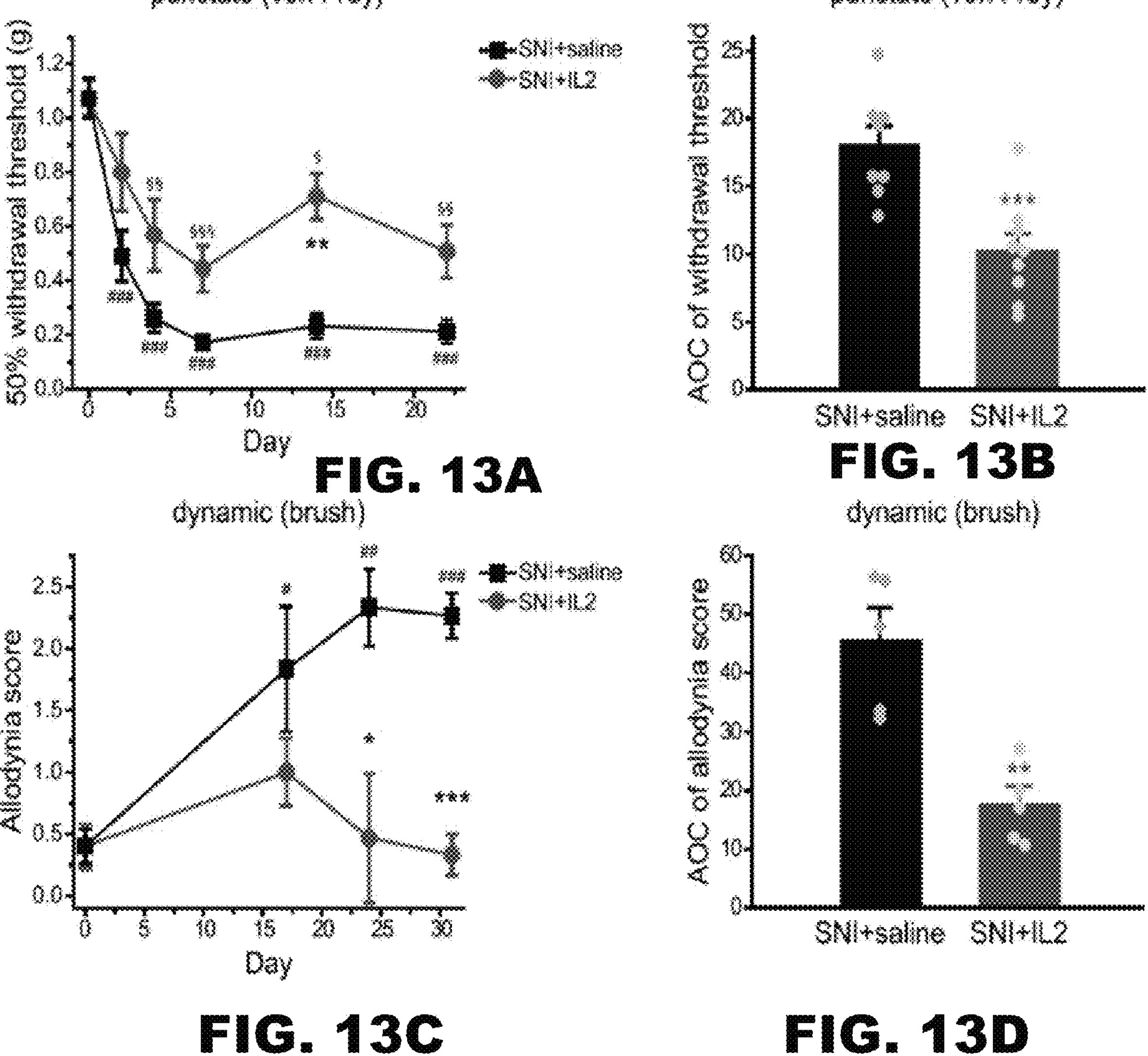
FIG. 13A-13D show pretreatment with ld-IL2 attenuates spared nerve injury (SNI)-induced punctate allodynia and prevents the development of SNI-induced dynamic allodynia.

Daily administration of ld-IL2 for up to 8 weeks has been shown to selectively boost Treg cells in patients with many self-reactive T cells. Here, female Swiss Webster mice were treated with daily ld-IL2 (1 μg/mouse/day, i.p.) or saline, starting 5 days before SNI and continuing till 21 days post-surgery. Basal punctate and dynamic mechanical sensitivity was not altered by 5 days of ld-IL2 injections (FIG. 13, SNI+saline versus SNI+IL2, Day 0). In saline-treated mice, the withdrawal threshold to von Frey filaments decreased to about 20% of the baseline value between 4-22 days post-SNI. In IL2-treated mice, SNI caused an average of 50% reduction of the withdrawal threshold (FIG. 13A). The integrated area over the time-effect curves (AOCs) calculated from day 0 baseline to day 22 post-SNI showed that ld-IL2 pretreatment significantly attenuated the magnitude of nerve injury-induced punctate allodynia (FIG. 13B). In addition to punctate allodynia, SNI induced dynamic allodynia to brush stimuli in saline-treated mice but not in mice that received ld-IL2 pretreatment (FIG. 13C). Both the time course and AOC of dynamic allodynia indicated that ld-IL2 pretreatment prevents the development of nerve injury-induced hyper-sensitivity to brush stimuli (FIGS. 13C-13D).

(ii) SNI-Induced Punctate and Dynamic Mechanical Allodynia are Reversed by Ld-IL2 Treatment.

Figures 14A, 14B, 14C, 14D, 14E, 14F:
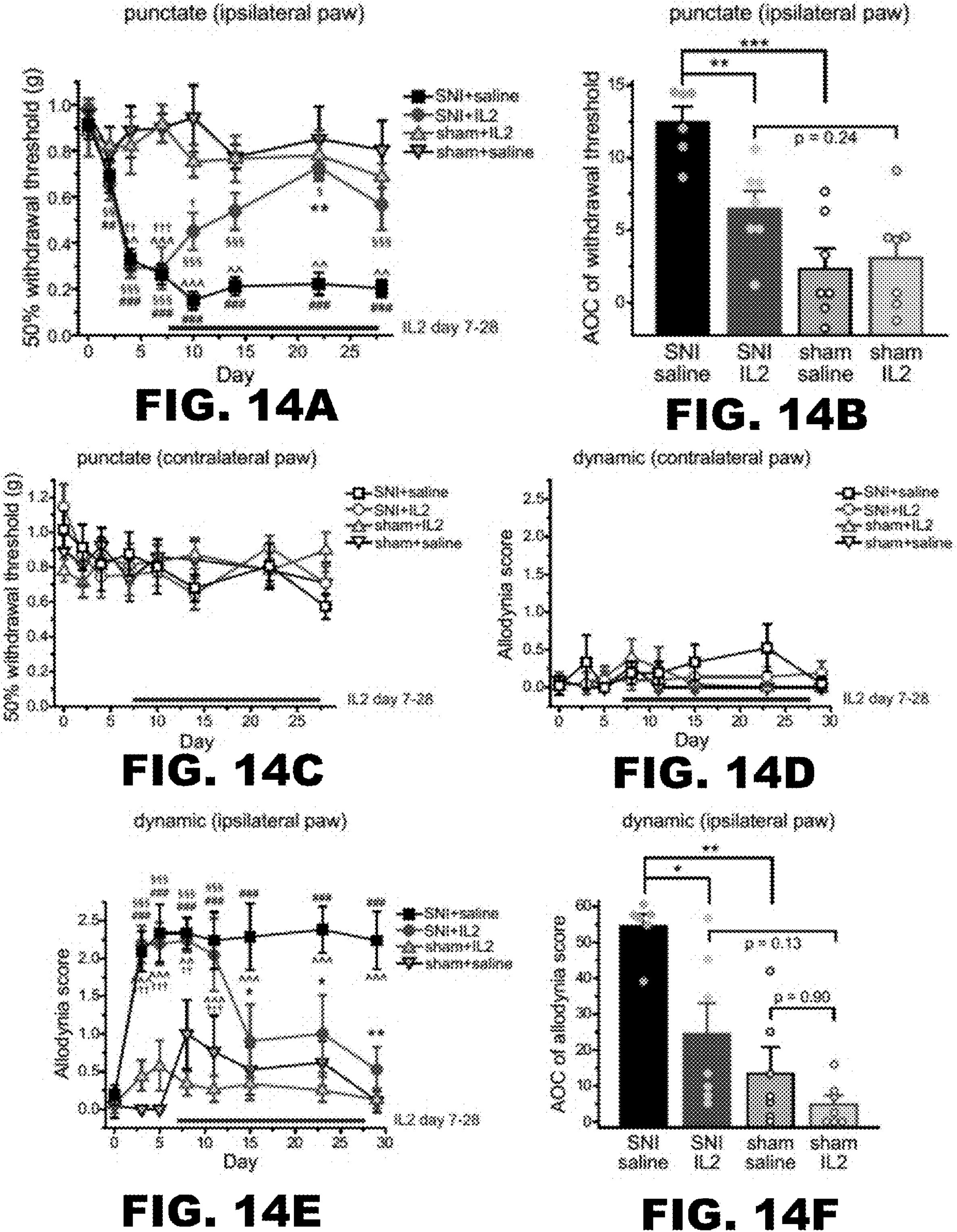
FIG. 14A-14F show SNI-induced punctate and dynamic mechanical allodynia are reversed by ld-IL2 treatment.

Further, it was tested whether delayed ld-IL2 treatment reverses SNI-induced punctate or dynamic allodynia. We started the 3-week ld-IL2 treatment 7 days post-SNI, at which time the punctate allodynia was well established on the ipsilateral (right) paws (FIG. 14A, SNI+saline and SNI+IL2 groups). SNI-induced punctate allodynia persisted for at least 28 days without treatment (FIG. 14A, SNI+saline group). The mechanical threshold started to reverse after 3 days of ld-IL2 treatment (FIG. 14A, SNI+IL2 group, day 10). After 7 days of IL2 treatment, the mechanical threshold of mice in the SNI+IL2 group was not different from that of mice in the sham+IL2 group (FIG. 14A, day 14-28). The integrated AOC of withdrawal threshold between day 10 and 28 post-SNI in the SNI+IL2 group was significantly lower than that of the SNI+saline group but was comparable to that of the sham+IL2 group (FIG. 14B). Notably, ld-IL2 treatment did not change the mechanical threshold of the contralateral (left) paw in mice underwent SNI surgery (FIG. 14C, SNI+IL2 group), nor did it affect the paw withdrawal threshold in mice that received sham surgery (FIG. 14A-14C, sham+saline versus sham+IL2 group).

Similar to punctate allodynia, the dynamic allodynia was fully established on the ipsilateral but not contralateral paws 3 days post-SNI and persisted for at least 29 days without treatment (FIG. 14D-14E, SNI+saline group). After 7 days of IL2 treatment, the dynamic allodynia was completely reversed and stayed at basal level with continuous IL2 treatment (FIG. 14E, day 15-29). The integrated AOC of dynamic allodynia score between day 10 and 28 post-SNI in the SNI+IL2 group was significantly lower than that of the SNI+saline group but was comparable to that of the sham+IL2 group (FIG. 14F). Ld-IL2 treatment did not change the responses to brush stimuli of the contralateral paw in mice underwent SNI surgery (FIG. 14D, SNI+IL2 group), or of the paws in mice that received sham surgery (FIG. 14D-14F, sham+saline versus sham+IL2 group). Taken together, it was concluded that delayed ld-IL2 treatment substantially attenuates SNI-induced punctate and dynamic allodynia without compromising the baseline responses to punctate or stroking stimuli.

(iii) Adoptive Transfer of Treg Cells Reverses the Morphine-Resistant Punctate and Dynamic Mechanical Allodynia.

Previous studies indicate that morphine attenuates nerve injury-induced punctate allodynia at early (<2 weeks post-injury) but not late stage; whereas nerve injury-induced dynamic allodynia does not respond to morphine treatment at all stages. Our data showed that ld-IL2 reverses the morphine-sensitive early punctate allodynia as well as the morphine-resistant dynamic allodynia (FIG. 14). Here, it was investigated whether enhancing Treg cell number/function is still beneficial in mice after both punctate and dynamic allodynia become morphine-resistant. First, C57BL/6J donor mice were treated with ld-IL2 for 12 days, as Treg cells from IL2-treated mice have been shown to exhibit stronger suppressive activity compared with those from saline-treated mice [16, 20]. Next, CD25+CD4+ Treg cells were enriched from IL2-treated mice and adoptively transferred the cells (1×106 cells/mouse) to male C57BL/6J mice 23 days post-SNI, at which time both punctate and dynamic allodynia become morphine-resistant. In the previous study, it was verified that the transferred cells contain 84% CD25+CD4+ cells and 76% Foxp3+CD25+CD4+ cells. The control group received adoptive transfer of CD25−CD4+ cells (1×106 cells/mouse) enriched from IL2-treated mice.

Before the adoptive transfer, all mice exhibited profound punctate allodynia on the paws ipsilateral to the SNI surgery (FIG. 15A). In control mice that received CD25−CD4+ cells, the punctate allodynia persisted throughout the experiment (FIG. 15A, SNI+CD25−CD4+ group, 26-46 days post-SNI). In mice that received Treg cells, the mechanical threshold was completely reversed 3 days after the transfer (FIG. 15A, SNI+ Treg group, day 26). The effect of transferred Treg cells lasted for 12 days (FIG. 15A, SNI+ Treg group, day 26-38), and the punctate allodynia recurred 23 days after Treg transfer (FIG. 15A, SNI+ Treg group, day 46). The integrated AOC of withdrawal threshold between day 26 and 45 post-SNI showed that transfer of Treg cells significantly attenuated the magnitude of nerve injury-induced punctate allodynia (FIG. 15B). Similar to the ld-IL2 treatment, Treg cell transfer did not change the responses to punctate or dynamic mechanical stimuli thresholds of the contralateral paws in mice underwent SNI surgery (FIG. 15C-15D).

SNI also resulted in significant dynamic allodynia on the ipsilateral paws of all mice (FIG. 15E). In control mice that received CD25−CD4+ cells, the dynamic allodynia persisted throughout the experiment (FIG. 15C, SNI+CD25−CD4+ group, 27-39 days post-SNI). In mice that received Treg cells, the dynamic allodynia was partially reversed 4 days after the transfer (FIG. 15C, SNI+ Treg group, day 27), and was completely reversed 2 days later (FIG. 15C, SNI+ Treg group, day 29). The effect of Treg transfer lasted for 9 days (FIG. 15C, SNI+ Treg group, day 27-35), and the dynamic allodynia recurred 16 days after Treg transfer (FIG. 15C, SNI+ Treg group, day 39). The integrated AOC of dynamic allodynia score between day 27 and 39 post-SNI in the SNI+ Treg group was significantly lower than that of the control group (FIG. 15F). Collectively, these results suggest that enhancing Treg cell number/function can reverse the morphine-resistant punctate and dynamic allodynia long after the nerve injury.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All references, patents and patent applications disclosed herein are incorporated by reference with respect to the subject matter for which each is cited, which in some cases may encompass the entirety of the document.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

What is claimed is:

1. A method of treating a headache in a subject in need thereof, the method comprising, systemically administering a composition comprising Interleukin-2 (IL-2) at a dose of about 0.05 MIU/$m^2$/day to less than 3.5 MIU/$m^2$/day that increases the amount of Treg cells in the subject daily for at least 6 days, wherein at least one symptom of the headache is reduced.

2. The method of claim 1, wherein the headache is a migraine, tension-type headache, cluster headache, medication-overuse headache, or trauma induced acute or chronic headache.

3. The method of claim 1, wherein IL-2 is administered at a dose of about 0.05 MIU/$m^2$/day to about 2 MIU/$m^2$/day.

4. The method of claim 1, wherein IL-2 is administered at a dose of about 2 MIU/$m^2$/day.

5. The method of claim 1, wherein the IL-2 is administered repeatedly.

6. The method of claim 1, wherein the IL-2 is administered daily for more than 7 days.

7. The method of claim 1, wherein the IL-2 is administered once per day for 4 to 5 consecutive days.

8. The method of claim 1, wherein the IL-2 administration is followed by a maintenance dose after 1 to 4 weeks.

9. The method of claim 1, wherein IL-2 is administered by subcutaneous route.

* * * * *